US012644123B2

(12) United States Patent
Dequeant et al.

(10) Patent No.: US 12,644,123 B2
(45) Date of Patent: Jun. 2, 2026

(54) MODULATING EXPRESSION OF ALAS1 (5'-AMINOLEVULINATE SYNTHASE 1) GENE

(71) Applicant: CRISPR Therapeutics AG, Zug (CH)

(72) Inventors: Mary-Lee Dequeant, South Boston, MA (US); Heidi Heath, South Boston, MA (US); Rachel Yuen, South Boston, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 0 days.

(21) Appl. No.: 18/778,981

(22) Filed: Jul. 21, 2024

(65) Prior Publication Data

US 2025/0027087 A1     Jan. 23, 2025

Related U.S. Application Data

(60) Provisional application No. 63/624,610, filed on Jan. 24, 2024, provisional application No. 63/598,408, filed on Nov. 13, 2023, provisional application No. 63/515,045, filed on Jul. 21, 2023.

(51) Int. Cl.
| | |
|---|---|
| *C12N 15/88* | (2006.01) |
| *C12N 9/22* | (2006.01) |
| *C12N 15/113* | (2010.01) |

(52) U.S. Cl.
CPC ............ *C12N 15/1137* (2013.01); *C12N 9/22* (2013.01); *C12N 15/88* (2013.01); *C12Y 203/01037* (2013.01); *C12N 2310/20* (2017.05); *C12N 2310/315* (2013.01); *C12N 2310/321* (2013.01)

(58) Field of Classification Search
CPC .... C12N 9/22; C12N 15/102; C12N 15/1082; C12N 15/70; C12N 15/01; C12N 2310/141; C12Y 203/01037
USPC ....................................................... 424/94.6
See application file for complete search history.

(56) References Cited

U.S. PATENT DOCUMENTS

| | | | |
|---|---|---|---|
| 5,173,414 | A | 12/1992 | Lebkowski et al. |
| 5,658,776 | A | 8/1997 | Flotte et al. |
| 5,786,211 | A | 7/1998 | Johnson |
| 5,871,982 | A | 2/1999 | Wilson et al. |
| 6,140,081 | A | 10/2000 | Barbas |
| 6,258,595 | B1 | 7/2001 | Gao et al. |
| 6,453,242 | B1 | 9/2002 | Eisenberg et al. |
| 6,534,261 | B1 | 3/2003 | Cox et al. |
| 7,427,396 | B2 | 9/2008 | Arbetman et al. |
| 7,588,772 | B2 | 9/2009 | Kay et al. |
| 7,888,121 | B2 | 2/2011 | Urnov et al. |
| 7,972,854 | B2 | 7/2011 | Miller et al. |
| 9,193,769 | B2 | 11/2015 | Chiorini et al. |
| 9,238,800 | B2 | 1/2016 | Bossis et al. |
| 10,968,452 | B2 * | 4/2021 | Hinkle et al. |
| 12,133,884 | B2 * | 11/2024 | Bryson et al. |
| 2011/0145940 | A1 | 6/2011 | Voytas et al. |
| 2016/0017005 | A1 | 1/2016 | Asokan et al. |
| 2021/0355463 | A1 | 11/2021 | Cobaugh |

FOREIGN PATENT DOCUMENTS

| | | |
|---|---|---|
| WO | WO1995/013365 | 5/1995 |
| WO | WO1995/013392 | 5/1995 |
| WO | WO1996/017947 | 6/1996 |
| WO | WO1997/006243 | 2/1997 |
| WO | WO1997/008298 | 3/1997 |
| WO | WO1997/009441 | 3/1997 |
| WO | WO1997/021825 | 6/1997 |
| WO | WO1998/053058 | 11/1998 |
| WO | WO1998/053059 | 11/1998 |
| WO | WO1998/053060 | 11/1998 |
| WO | WO1999/011764 | 3/1999 |
| WO | WO2001/083692 | 11/2001 |
| WO | WO2002/016536 | 2/2002 |
| WO | WO2003/016496 | 2/2003 |
| WO | WO2008/016473 | 2/2008 |
| WO | WO2008/157688 | 12/2008 |
| WO | WO2009/149253 | 12/2009 |
| WO | WO2011/015347 | 2/2011 |
| WO | WO2013/052523 | 4/2013 |
| WO | WO2013/059475 | 4/2013 |
| WO | WO2013/151666 | 10/2013 |
| WO | WO2015/121501 | 8/2015 |
| WO | WO2015/188933 | 12/2015 |
| WO | WO2016/061487 | 4/2016 |
| WO | WO2016/193226 | 12/2016 |
| WO | WO2017/048843 | 3/2017 |
| WO | WO2017/053297 | 3/2017 |
| WO | WO2017/066781 | 4/2017 |
| WO | WO2017/066782 | 4/2017 |
| WO | WO2017/066789 | 4/2017 |

(Continued)

OTHER PUBLICATIONS

Anderson, "Acute hepatic porphyrias: current diagnosis & management," Molecular genetics and metabolism 2019, 128(3), 219-227.
Carter, "Adeno-associated virus vectors," Current opinion in biotechnology 1992, 3(5), 533-539.
Chan et al., "Preclinical development of a subcutaneous ALAS1 RNAi therapeutic for treatment of hepatic porphyrias using circulating RNA quantification," Molecular Therapy-Nucleic Acids 2015, 4, in 9 pages.
Chen et al., "Characterization of the hepatic transcriptome following phenobarbital induction in mice with AIP," Molecular genetics and metabolism 2019, 128(3), 382-390.
Clark et al., "A stable cell line carrying adenovirus-inducible rep and cap genes allows for infectivity titration of adeno-associated virus vectors," Gene Therapy 1996, 3(12), 1124-1132.
Deverman et al., "Cre-dependent selection yields AAV variants for widespread gene transfer to the adult brain," Nature biotechnology 2016, 34(2), 204-209.

(Continued)

*Primary Examiner* — Tekchand Saidha
*Assistant Examiner* — Mohammad Y Meah
(74) *Attorney, Agent, or Firm* — Dickinson Wright PLLC

(57) ABSTRACT

The present disclosure relates to methods, compositions and kits for treating conditions that are related to the modulation of expression of 5'-Aminolevulinate Synthase 1 (ALAS1) by gene editing.

8 Claims, 9 Drawing Sheets

Specification includes a Sequence Listing.

(56)             References Cited

FOREIGN PATENT DOCUMENTS

| WO | WO2017/066791 | 4/2017 |
|----|---------------|--------|
| WO | WO2017/066793 | 4/2017 |
| WO | WO2017/066797 | 4/2017 |
| WO | WO2017/070632 | 4/2017 |
| WO | WO2018/027078 | 2/2018 |
| WO | WO2018/075827 | 4/2018 |
| WO | WO2019/108559 | 6/2019 |
| WO | WO2019/217942 | 11/2019 |
| WO | WO2020/191153 | 9/2020 |
| WO | WO2020/191171 | 9/2020 |
| WO | WO2020/191233 | 9/2020 |
| WO | WO2020/191234 | 9/2020 |
| WO | WO2020/191239 | 9/2020 |
| WO | WO2020/191241 | 9/2020 |
| WO | WO2020/191242 | 9/2020 |
| WO | WO2020/191243 | 9/2020 |
| WO | WO2020/191245 | 9/2020 |
| WO | WO2020/191246 | 9/2020 |
| WO | WO2020/191248 | 9/2020 |
| WO | WO2020/191249 | 9/2020 |
| WO | WO2022/067130 | 3/2022 |
| WO | WO2022/150790 | 7/2022 |
| WO | WO2023/015309 | 2/2023 |

OTHER PUBLICATIONS

Gaudelli et al., "Programmable base editing of A• T to G• C in genomic DNA without DNA cleavage," Nature 2017, 551(7681), 464-471.

Grimm et al., "In vitro and in vivo gene therapy vector evolution via multispecies interbreeding and retargeting of adeno-associated viruses," Journal of virology 2008, 82(12), 5887-5911.

Hermonat & Muzyczka, "Use of adeno-associated virus as a mammalian DNA cloning vector: transduction of neomycin resistance into mammalian tissue culture cells," Proceedings of the National Academy of Sciences 1984, 81(20), 6466-6470.

Invitation to Pay Additional Fees and, Where Applicable, Protest Fee dated Nov. 20, 2024 in PCT Patent Application No. PCT/182024/057065.

Komor et al., "Programmable editing of a target base in genomic DNA without double-stranded DNA cleavage," Nature 2016, 533(7603), 420-424.

Kothadia, et al., "Acute Hepatic Porphyria," National Library of Medicine 2024, in 8 pages. https://www.ncbi.nlm.nih.gov/books/NBK537178/.

Lebkowski et al., "Adeno-associated virus: a vector system for efficient introduction and integration of DNA into a variety of mammalian cell types," Molecular and cellular biology 1988, in 9 pages.

Lian et al., "Alas1 is essential for neutrophil maturation in zebrafish," haematologica 2018, 103(11), in 11 pages.

Mclaughlin et al., "Adeno-associated virus general transduction vectors: analysis of proviral structures," Journal of virology 1988, 62(6), 1963-1973.

Muzyczka, "Use of adeno-associated virus as a general transduction vector for mammalian cells," Viral expression 1992, vectors, 97-129.

National Institutes of Health, "Porphyria," nih.gov 2024, in 10 pages. https://www.niddk.nih.gov/health-information/liver-disease/porphyria.

Paul et al., "Increased viral titer through concentration of viral harvests from retroviral packaging lines," Human gene therapy 1993, 4(5), 609-615.

Perrin et al., "An experimental rabies vaccine produced with a new BHK-21 suspension cell culture process: use of serum-free medium and perfusion-reactor system," Vaccine 1995, 13(13), 1244-1250.

Pulicherla et al., "Engineering liver-detargeted AAV9 vectors for cardiac and musculoskeletal gene transfer," Molecular Therapy 2011, 19(6), 1070-1078.

Saitoh et al., "5-aminolevulinic acid (ALA) deficiency causes impaired glucose tolerance and insulin resistance coincident with an attenuation of mitochondrial function in aged mice," PLoS One 2018, 13(1), in 20 pages.

Samulski et al., "Helper-free stocks of recombinant adeno-associated viruses: normal integration does not require viral gene expression," Journal of virology 1989, 63(9), 3822-3828.

Sardh & Harper, "RNAi therapy with givosiran significantly reduces attack rates in acute intermittent porphyria," Journal of Internal Medicine 2022, 291(5), 593-610.

Sato et al., "Different kinetics for the hepatic uptake of lipid nanoparticles between the apolipoprotein E/low density lipoprotein receptor and the N-acetyl-d-galactosamine/asialoglycoprotein receptor pathway," Journal of Controlled Release 2020, 322, 217-226.

Tratschin et al., "A human parvovirus, adeno-associated virus, as a eucaryotic vector: transient expression and encapsidation of the procaryotic gene for chloramphenicol acetyltransferase," Molecular and cellular 1984, biology, in 10 pages.

Tratschin et al., "Adeno-associated virus vector for high-frequency integration, expression, and rescue of genes in mammalian cells," Molecular and cellular biology 1985, 5(11), 3251-3260.

Van Wijk et al., "Heterozygous disruption of ALAS1 in mice causes an accelerated age-dependent reduction in free heme, but not total heme, in skeletal muscle and liver," Archives of Biochemistry and Biophysics 2021, 697, in 8 pages.

Verma & Eckstein, "Modified oligonucleotides: synthesis and strategy for users," Annual review of biochemistry 1998, 67(1), 99-134.

Yasuda et al., "Homozygous hydroxymethylbilane synthase knock-in mice provide pathogenic insights into the severe neurological impairments present in human homozygous dominant acute intermittent porphyria," Human molecular genetics 2019, 28(11), 1755-1767.

Yasuda et al., "RNAi-mediated silencing of hepatic Alas1 effectively prevents and treats the induced acute attacks in acute intermittent porphyria mice," Proceedings of the National Academy of Sciences 2014, 111(21), 7777-7782.

International Search Report and Written Opinion dated Jan. 14, 2025 in PCT Application No. PCT/IB2024/057065.

* cited by examiner

Editing of ALAS1 in Human Hepatocytes

Donor 1
Donor 2
Donor 3
Donor 4
Donor 5
Donor 6

Total Efficiency (%)

LNP Dose (ng/ul)

↑ALAS1 upregulated

ALA and PBG cannot be broken down by HMBS and builds up to toxic levels in liver causing acute attacks ALA and PBG circulate outside the liver, causing additional toxicity (i.e., respiratory, CNS symptoms)

Editing and Protein Dose Curve in Human Hepatocytes

Editing and Protein Dose Curve in NHP Hepatocytes

SEQUENCE LISTING

Sequence total quantity: 112
SEQ ID NO: 1              moltype = DNA   length = 20
FEATURE                   Location/Qualifiers
source                    1..20
                          mol_type = other DNA
                          organism = synthetic construct
SEQUENCE: 1
gccccaactt ccatcatctt                                                    20

SEQ ID NO: 2              moltype = DNA   length = 20
FEATURE                   Location/Qualifiers
source                    1..20
                          mol_type = other DNA
                          organism = synthetic construct
SEQUENCE: 2
gatggcacac agcttccgtc                                                    20

SEQ ID NO: 3              moltype = DNA   length = 20
FEATURE                   Location/Qualifiers
source                    1..20
                          mol_type = other DNA
                          organism = synthetic construct
SEQUENCE: 3
taactgcccc acacacccgt                                                    20

SEQ ID NO: 4              moltype = DNA   length = 20
FEATURE                   Location/Qualifiers
source                    1..20
                          mol_type = other DNA
                          organism = synthetic construct
SEQUENCE: 4
attcttatcc cgagtccccc                                                    20

SEQ ID NO: 5              moltype = DNA   length = 20
FEATURE                   Location/Qualifiers
source                    1..20
                          mol_type = other DNA
                          organism = synthetic construct
SEQUENCE: 5
agaagatgag acactctttc                                                    20

SEQ ID NO: 6              moltype = DNA   length = 20
FEATURE                   Location/Qualifiers
source                    1..20
                          mol_type = other DNA
                          organism = synthetic construct
SEQUENCE: 6
ttttcacact aaccacactg                                                    20

SEQ ID NO: 7              moltype = DNA   length = 20
FEATURE                   Location/Qualifiers
source                    1..20
                          mol_type = other DNA
                          organism = synthetic construct
SEQUENCE: 7
gttttcacac taaccacact                                                    20

SEQ ID NO: 8              moltype = DNA   length = 20
FEATURE                   Location/Qualifiers
source                    1..20
                          mol_type = other DNA
                          organism = synthetic construct
SEQUENCE: 8
gctgaggttt cagcaacctc                                                    20

SEQ ID NO: 9              moltype = DNA   length = 20
FEATURE                   Location/Qualifiers
source                    1..20
                          mol_type = other DNA
                          organism = synthetic construct
SEQUENCE: 9
tttgcttttg catgatgtcc                                                    20

SEQ ID NO: 10             moltype = DNA   length = 20
FEATURE                   Location/Qualifiers
source                    1..20
                          mol_type = other DNA
                          organism = synthetic construct

```
SEQUENCE: 10
aggaatgagt cgccacccac                                                        20

SEQ ID NO: 11          moltype = DNA   length = 20
FEATURE                Location/Qualifiers
source                 1..20
                       mol_type = other DNA
                       organism = synthetic construct
SEQUENCE: 11
gtcgccaccc acgggtgtgt                                                        20

SEQ ID NO: 12          moltype = DNA   length = 20
FEATURE                Location/Qualifiers
source                 1..20
                       mol_type = other DNA
                       organism = synthetic construct
SEQUENCE: 12
ataactgccc cacacacccg                                                        20

SEQ ID NO: 13          moltype = DNA   length = 20
FEATURE                Location/Qualifiers
source                 1..20
                       mol_type = other DNA
                       organism = synthetic construct
SEQUENCE: 13
agtcgccacc cacgggtgtg                                                        20

SEQ ID NO: 14          moltype = DNA   length = 20
FEATURE                Location/Qualifiers
source                 1..20
                       mol_type = other DNA
                       organism = synthetic construct
SEQUENCE: 14
gctgatgtgg acagggttcg                                                        20

SEQ ID NO: 15          moltype = DNA   length = 20
FEATURE                Location/Qualifiers
source                 1..20
                       mol_type = other DNA
                       organism = synthetic construct
SEQUENCE: 15
cgtcttccgc aaggccagtc                                                        20

SEQ ID NO: 16          moltype = DNA   length = 20
FEATURE                Location/Qualifiers
source                 1..20
                       mol_type = other DNA
                       organism = synthetic construct
SEQUENCE: 16
aagagtgtct catcttcttc                                                        20

SEQ ID NO: 17          moltype = DNA   length = 20
FEATURE                Location/Qualifiers
source                 1..20
                       mol_type = other DNA
                       organism = synthetic construct
SEQUENCE: 17
catcggtttt cacattaacc                                                        20

SEQ ID NO: 18          moltype = DNA   length = 20
FEATURE                Location/Qualifiers
source                 1..20
                       mol_type = other DNA
                       organism = synthetic construct
SEQUENCE: 18
tcggcttgga tcctctccat                                                        20

SEQ ID NO: 19          moltype = DNA   length = 20
FEATURE                Location/Qualifiers
source                 1..20
                       mol_type = other DNA
                       organism = synthetic construct
SEQUENCE: 19
aagttcttca gcagtcggct                                                        20

SEQ ID NO: 20          moltype = DNA   length = 20
FEATURE                Location/Qualifiers
source                 1..20
                       mol_type = other DNA
```

-continued

```
                              organism = synthetic construct
SEQUENCE: 20
tccgtgtagt catccgccat                                                    20

SEQ ID NO: 21          moltype = DNA  length = 20
FEATURE                Location/Qualifiers
source                 1..20
                       mol_type = other DNA
                       organism = synthetic construct
SEQUENCE: 21
cccgatggcg gatgactaca                                                    20

SEQ ID NO: 22          moltype = DNA  length = 20
FEATURE                Location/Qualifiers
source                 1..20
                       mol_type = other DNA
                       organism = synthetic construct
SEQUENCE: 22
ccgtgtagtc atccgccatc                                                    20

SEQ ID NO: 23          moltype = DNA  length = 20
FEATURE                Location/Qualifiers
source                 1..20
                       mol_type = other DNA
                       organism = synthetic construct
SEQUENCE: 23
ccaaaaagca ggtgtcggtc                                                    20

SEQ ID NO: 24          moltype = DNA  length = 20
FEATURE                Location/Qualifiers
source                 1..20
                       mol_type = other DNA
                       organism = synthetic construct
SEQUENCE: 24
agtcgacacc cacgggtgtg                                                    20

SEQ ID NO: 25          moltype = RNA  length = 20
FEATURE                Location/Qualifiers
source                 1..20
                       mol_type = other RNA
                       organism = synthetic construct
SEQUENCE: 25
gccccaactt ccatcatctt                                                    20

SEQ ID NO: 26          moltype = RNA  length = 20
FEATURE                Location/Qualifiers
source                 1..20
                       mol_type = other RNA
                       organism = synthetic construct
SEQUENCE: 26
gatggcacac agcttccgtc                                                    20

SEQ ID NO: 27          moltype = RNA  length = 20
FEATURE                Location/Qualifiers
source                 1..20
                       mol_type = other RNA
                       organism = synthetic construct
SEQUENCE: 27
taactgcccc acacacccgt                                                    20

SEQ ID NO: 28          moltype = RNA  length = 20
FEATURE                Location/Qualifiers
source                 1..20
                       mol_type = other RNA
                       organism = synthetic construct
SEQUENCE: 28
attcttatcc cgagtccccc                                                    20

SEQ ID NO: 29          moltype = RNA  length = 20
FEATURE                Location/Qualifiers
source                 1..20
                       mol_type = other RNA
                       organism = synthetic construct
SEQUENCE: 29
agaagatgag acactctttc                                                    20

SEQ ID NO: 30          moltype = RNA  length = 20
FEATURE                Location/Qualifiers
source                 1..20
```

-continued

```
                              mol_type = other RNA
                              organism = synthetic construct
SEQUENCE: 30
ttttcacact aaccacactg                                          20

SEQ ID NO: 31          moltype = RNA   length = 20
FEATURE                Location/Qualifiers
source                 1..20
                       mol_type = other RNA
                       organism = synthetic construct
SEQUENCE: 31
gttttcacac taaccacact                                          20

SEQ ID NO: 32          moltype = RNA   length = 20
FEATURE                Location/Qualifiers
source                 1..20
                       mol_type = other RNA
                       organism = synthetic construct
SEQUENCE: 32
gctgaggttt cagcaacctc                                          20

SEQ ID NO: 33          moltype = RNA   length = 20
FEATURE                Location/Qualifiers
source                 1..20
                       mol_type = other RNA
                       organism = synthetic construct
SEQUENCE: 33
tttgcttttg catgatgtcc                                          20

SEQ ID NO: 34          moltype = RNA   length = 20
FEATURE                Location/Qualifiers
source                 1..20
                       mol_type = other RNA
                       organism = synthetic construct
SEQUENCE: 34
aggaatgagt cgccacccac                                          20

SEQ ID NO: 35          moltype = RNA   length = 20
FEATURE                Location/Qualifiers
source                 1..20
                       mol_type = other RNA
                       organism = synthetic construct
SEQUENCE: 35
gtcgccaccc acgggtgtgt                                          20

SEQ ID NO: 36          moltype = RNA   length = 20
FEATURE                Location/Qualifiers
source                 1..20
                       mol_type = other RNA
                       organism = synthetic construct
SEQUENCE: 36
ataactgccc cacacacccg                                          20

SEQ ID NO: 37          moltype = RNA   length = 20
FEATURE                Location/Qualifiers
source                 1..20
                       mol_type = other RNA
                       organism = synthetic construct
SEQUENCE: 37
agtcgccacc cacgggtgtg                                          20

SEQ ID NO: 38          moltype = RNA   length = 20
FEATURE                Location/Qualifiers
source                 1..20
                       mol_type = other RNA
                       organism = synthetic construct
SEQUENCE: 38
gctgatgtgg acagggttcg                                          20

SEQ ID NO: 39          moltype = RNA   length = 20
FEATURE                Location/Qualifiers
source                 1..20
                       mol_type = other RNA
                       organism = synthetic construct
SEQUENCE: 39
cgtcttccgc aaggccagtc                                          20

SEQ ID NO: 40          moltype = RNA   length = 20
FEATURE                Location/Qualifiers
```

-continued

```
source                    1..20
                          mol_type = other RNA
                          organism = synthetic construct
SEQUENCE: 40
aagagtgtct catcttcttc                                              20

SEQ ID NO: 41             moltype = RNA   length = 20
FEATURE                   Location/Qualifiers
source                    1..20
                          mol_type = other RNA
                          organism = synthetic construct
SEQUENCE: 41
catcggtttt cacattaacc                                              20

SEQ ID NO: 42             moltype = RNA   length = 20
FEATURE                   Location/Qualifiers
source                    1..20
                          mol_type = other RNA
                          organism = synthetic construct
SEQUENCE: 42
tcggcttgga tcctctccat                                              20

SEQ ID NO: 43             moltype = RNA   length = 20
FEATURE                   Location/Qualifiers
source                    1..20
                          mol_type = other RNA
                          organism = synthetic construct
SEQUENCE: 43
aagttcttca gcagtcggct                                              20

SEQ ID NO: 44             moltype = RNA   length = 20
FEATURE                   Location/Qualifiers
source                    1..20
                          mol_type = other RNA
                          organism = synthetic construct
SEQUENCE: 44
tccgtgtagt catccgccat                                              20

SEQ ID NO: 45             moltype = RNA   length = 20
FEATURE                   Location/Qualifiers
source                    1..20
                          mol_type = other RNA
                          organism = synthetic construct
SEQUENCE: 45
cccgatggcg gatgactaca                                              20

SEQ ID NO: 46             moltype = RNA   length = 20
FEATURE                   Location/Qualifiers
source                    1..20
                          mol_type = other RNA
                          organism = synthetic construct
SEQUENCE: 46
ccgtgtagtc atccgccatc                                              20

SEQ ID NO: 47             moltype = RNA   length = 20
FEATURE                   Location/Qualifiers
source                    1..20
                          mol_type = other RNA
                          organism = synthetic construct
SEQUENCE: 47
ccaaaaagca ggtgtcggtc                                              20

SEQ ID NO: 48             moltype = RNA   length = 20
FEATURE                   Location/Qualifiers
source                    1..20
                          mol_type = other RNA
                          organism = synthetic construct
SEQUENCE: 48
agtcgacacc cacgggtgtg                                              20

SEQ ID NO: 49             moltype = RNA   length = 80
FEATURE                   Location/Qualifiers
misc_feature              1..80
                          note = Synthetic nucleotide
source                    1..80
                          mol_type = other RNA
                          organism = synthetic construct
SEQUENCE: 49
gttttagagc tagaaatagc aagttaaaat aaggctagtc cgttatcaac ttgaaaaagt   60
```

```
ggcaccgagt cggtgctttt                                              80

SEQ ID NO: 50           moltype = RNA  length = 4506
FEATURE                 Location/Qualifiers
misc_feature            1..4506
                        note = Synthetic
source                  1..4506
                        mol_type = other RNA
                        organism = synthetic construct
SEQUENCE: 50
agaggaaata agagagaaaa gaagagtaag aagaaatata agagccacca tggcccctaa   60
gaagaagaga aaagtcggaa ttcacggagt ccccgccgcc gacaaaaagt actccattgg  120
ccttgatatt ggaaccaact ccgtgggttg ggccgtgatc actgacgagt acaaggtgcc  180
gtccaagaag ttcaaggtgc tggggaacac tgaccggcac tcaattaaga agaacctgat  240
tggggcgctg ctgttcgact ccggagaaac cgcggaggct acccgcctga agcggactgc  300
ccggcggaga tacacgcgca ggaagaaccg gatttgctac ctccaagaaa tcttcagcaa  360
cgaaatggca aaggtggacg attccttctt ccatcgcctg gaagagagct tcctggtgga  420
agaggacaag aagcacgaaa gacacccgat tttcggcaac atcgtggatg aggtcgcata  480
ccacgaaaag taccccacca tctatcatct tcggaagaag ctggtcgact ccaccgataa  540
ggccgatctg cgcctgatct acttggcgct ggctcacatg attaagttca gaggacactt  600
tctgatagag ggcgacctca atcccgataa ctccgacgtg gataagctgt tcatccaact  660
ggtgcagacg tacaaccaac tgtttgaaga gaatccaatc aacgccagcg gggtggacgc  720
caaggccatc ctgtccgccc ggctgtcaaa gtccagacgc ctggagaatc tcatcgcgca  780
actccctggc gaaaaaagaa acggactctt cgggaatctg attgctctgt ccctgggggct  840
cactccgaac ttcaagtcga acttcgacct ggcggaggac gctaagctgc agctgtccaa  900
ggacacctac gatgacgatc tggataacct tctggccgac atcgggatc aatacgtgga  960
tctcttcctg gccgcaaaga acttgtcgga tgctattctg ctgagcgaca ttctgcgggt 1020
caatactgaa atcaccaagg cgccctgtc ggccagcatg atcaagcgct acgacgaaca 1080
ccaccaagac ctgactctgc tgaaggccct cgtgcgccag cagctgcctg aaaagtacaa 1140
ggagattttc ttcgaccagt ccaagaacgg atacgccgga tacattgacg gaggggccag 1200
ccaggaggaa ttttacaaat tcatcaagcc cattctcgag aaaatggacg gaaccgaaga 1260
gttgctcgtg aagctgaaca gagaggatc cctccggaag cagcggacct tcgacaacgg 1320
ttccatcccg caccaaatcc acctgggcga attgcacgcc atcctccggc ggcaggaaga 1380
tttctaccca ttcttgaagg acaatcgcga aaagatcgaa aagatcttga ctttccgcat 1440
cccgtactac gtgggccctc tggccgcgg caactcccgc ttcgcttgaa tgacacggaa 1500
gtccgaggaa accattacgc cctggaactt cgaggaagtg gtggacaagg gggcgtccgc 1560
ccagagcttc atcgaacgca tgaccaattt cgacaagaac ctcccgaacg aaaaagtgct 1620
gccaaagcac tcgctcctct acgaatactt caccgtgtac aacgagctga ctaaggtcaa 1680
atacgtgact gagggaatgc ggaagccggc cttcctgtcg ggagacagca agaaggccat 1740
agtggacttg cttttcaaga ctaaccggaa ggtcactgtg aagcaactca aggaggacta 1800
cttcaagaag atcgagtgtt tcgactcggt ggagatctcg ggtgtcgagg accgcttcaa 1860
cgcctccctg ggaacttacc acgatctgct gaagatcatc aaggacaagg acttcctcga 1920
taacgaagaa aatgaggaca tcctcgagga tatcgtgctg accctgacct tgttcgagga 1980
tagggagatg atcgaggagc ggctcaagac ctacgcccac ctgtttgacg acaaagtgat 2040
gaagcaactg aaacggcgga ggtataccgg ctggggtcgg ctgtcccgca agctgatcaa 2100
cgggatcagg gacaagcagt ccggaaagac catcctcgac ttccttaagt ccgacggatt 2160
cgcgaaccgc aacttcatgc aacttatcca cgacgactcg ctgacattca ggaagatat  2220
ccagaaggcc caggtgtccg gacaggggga ctcgcttcat gagcacatcg ctaacctggc 2280
cggatccccc gccataaaaa agggcattct gcagaccgtc aaagtggtgg atgagctggt 2340
caaggtcatg ggccggcata agccggaaaa catcgtcatc gagatggccc gcgagaacca 2400
gactacgcag aagggccaga agaactcccg ggagcggata agcggattg aagagggcat 2460
caaggagctc ggcagccaga ttctgaagga acatcccgtg gaaaacaccc agctgcaaaa 2520
cgaaaagctc tatttgtact atctgcaaaa cggacgcgat atgtacgtgg atcaggagct 2580
ggacattaac agactgagcg actatgacgt ggatcacatt gtgcctcaaa gcttcctcaa 2640
ggacgactca attgacaaca aggtcctgac cagaagcgac aagaacagag gaaagtcgga 2700
taatgtgccg tccgaagaag tggtcaagaa gatgaagaat tactggagac agctcctgaa 2760
tgcgaagctc attacccagc ggaagttcga taacctgacc aaggccgaaa ggggtggact 2820
gtccgaactc gacaaagctg gcttcatcaa gcgccaactg tcgaaaccga gcagatcac  2880
caagcgcgtc gcccagattc tggacagccg catgaacact aagtacgacg agaacgataa 2940
gctgatccgc gaagtgaagg tcatcaccct gaagtccaag ctcgtgtccg actttcggaa 3000
ggatttccag ttttacaagg tccgcgagat caacaactac catcacgccc acgacgcgta 3060
ccttaacgca gtcgtgggaa cggctcttat caagaagtac ccaaagctgg agtcggaatt 3120
tgtgtacgga gactacaaag tgtacgacgt gcgcaagatg atcgccaaat ctgagcaaga 3180
gatcgggaag gcaaccgcca aatacttctt ctactcaaac attatgaatt ttttcaaaac 3240
tgagattacc ctggctaacg gagaaattcg gaagcgcccc ctgattgaaa ccaacggaga 3300
aactggagaa attgtgtggg acaagggacg ggacttcgcc accgtccgca aggtcctctc 3360
aatgcccca gtcaacatcg tgaaaagac cgaagtgcaa accggcggct ctcaaagga  3420
gtccatcctg cctaagcgca cagcgacaa gctgattgac aggaagaagg actgggaccc 3480
gaagaagtac ggaggatttg attcccctac cgtggcctac tccgtgctcg tggtggcaa  3540
agtggaaaag gggaaatcca agaagctgaa gtcggtgaag gagcttttgg gtatcaccat 3600
catggaacgc tcctcgttcg aaaagaaccc aatcgatttc ctggaagcta agggttataa 3660
ggaagtgaaa aaggacctga ttatcaagct gcccaagtac tcactgttcg agctggaaaa 3720
cggtcggaaa aggatgctgg ccagcgccgg agaactccag aagggaaacg aactggcact 3780
gccgtccaaa tacgtcaact tcctctacct tgcatcccat tacgaaaaac tcaagggatc 3840
gccgaggac aacgagcaga agcagctttt cgtggagcaa cacaagcatt acttggacga 3900
gatcatcgag cagatttccg agttctcaaa gcgcgtgatc ctggccgacg caaatctgga 3960
caaggtcctg tccgcgtaca ataagcatcg ggacaagcct atccgcgaac aggccgagaa 4020
catcatccat ctgttcactc tgacaaacct gggcgcaccc gccgcgttca gtactttga  4080
caccaccatc gataggaagc gatacacctc aactaaggaa gtgttggacg cgaccccttat 4140
```

```
ccatcagtcg atcaccgggc tgtacgaaac acggatcgac ctcagccagt tgggaggcga    4200
caagcgccct gcggctacca agaaggccgg acaggccaag aagaagaaat gagcggccgc    4260
ttaattaagc tgccttctgc ggggcttgcc ttctggccat gcccttcttc tctcccttgc    4320
acctgtacct cttggtcttt gaataaagcc tgagtaggaa gtctagaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaa                                                                4506

SEQ ID NO: 51            moltype = RNA  length = 4444
FEATURE                  Location/Qualifiers
misc_feature             1..4444
                         note = Synthetic
source                   1..4444
                         mol_type = other RNA
                         organism = synthetic construct
SEQUENCE: 51
aggaaataag agagaaaaga agagtaagaa gaaatataag agccaccatg gcccccaaaga    60
agaagcggaa ggtcggtatc cacggagtcc cagcagccga caagaagtac agcatcggcc    120
tggacatcgg caccaactct gtgggctggg ccgtgatcac cgacgagtac aaggtgccca    180
gcaagaaatt caaggtgctg ggcaacaccg accggcacag catcaagaag aacctgatcg    240
gagccctgct gttcgacagc ggcgaaacag ccgaggccac ccggctgaag agaaccgcca    300
gaagaagata caccagacgg aagaaccgga tctgctatct gcaagagatc ttcagcaacg    360
agatggccaa ggtggacgac agcttcttcc acagactgga agagtccttc ctggtggaag    420
aggacaagaa gcacgagaga caccccatct cggcaacat cgtggacgag gtggcctacc    480
acgagaagta ccccaccatc taccacctga aaagaaact ggtggacagc accgacaagg    540
ccgacctgag actgatctac ctggccctga cccacatgat caagttcaga ggccacttcc    600
tgatcgaggg cgacctgaac cccgacaaca gcgacgtgga caagctgttc atccagctgg    660
tgcagaccta caaccagctg ttcgaggaaa accccatcaa cgccagcggc gtggacgcca    720
aggctatcct gtctgccaga ctgagcaaga gcagaaggct ggaaaatctg atcgcccagc    780
tgcccggcga gaagaagaac ggcctgttcg gcaacctgat tgccctgagc ctgggcctga    840
cccccaactt caagagcaac ttcgacctgg ccgaggatgc caaactgcag ctgagcaagg    900
acacctacga cgacgacctg gacaacctgc tggcccagat cggcgaccag tacgccgacc    960
tgttcctggc cgccaagaac ctgtctgacg ccatcctgct gagcgacatc ctgagagtga    1020
acaccgagat caccaaggcc cccctgagcg cctctatgat caagagatac gacgagcacc    1080
accaggacct gaccctgctg aaagctctcg tgcggcagca gctgcctgag aagtacaaag    1140
aaatcttctt cgaccagagc aagaacggct acgccggcta catcgatggc ggcgctagcc    1200
aggaagagtt ctacaagttc atcaagccca tcctggaaaa gatggacggc accgaggaac    1260
tgctcgtgaa gctgaacaga gaggacctgc tgagaaagca gagaaccttc gacaacggca    1320
gcatccccca ccagatccac ctgggagagc tgcacgctat cctggaaagg caggaagatt    1380
tttacccatt cctgaaggac aaccgggaaa agatcgagaa gatcctgacc ttcaggatcc    1440
cctactacgt gggcccctg gccagaggca acagcagatt cgcctggatg accagaaaga    1500
gcgaggaaac catcaccccc tggaacttcg aggaagtggt ggacaaggc gccagcgccc    1560
agagcttcat cgagagaatg acaaacttcg ataagaacct gcccaacgag aaggtgctgc    1620
ccaagcacag cctgctgtac gagtacttca ccgtgtacaa cgagctgacc aaagtgaaat    1680
acgtgaccga gggaatgaga aagcccgcct tcctgagcgg cgagcagaaa aaggccatcg    1740
tggacctgct gttcaagacc aacagaaaag tgaccgtgaa gcagctgaaa gaggactact    1800
tcaagaaaat cgagtgcttc gactccgtgg aaatctccgg cgtggaagat agattcaacg    1860
cctccctggg cacataccac gatctgctga aaattatcaa ggacaaggac ttcctggata    1920
acgaagagaa cgaggacatt ctggaagata tcgtgctgac cctgacactg tttgaggacc    1980
gcgagatgat cgaggaaagg ctgaaaacct acgctcacct gttcgacgac aaagtgatga    2040
agcagctgaa gagaaggcgg tacaccggct ggggcaggct gagcagaaag ctgatcaacg    2100
gcatcagaga caagcagagc ggcaagacaa tcctggattt cctgaagtcc gacggcttcg    2160
ccaaccggaa cttcatgcag ctgatccacg acgacagcct gacattcaaa gaggacatcc    2220
agaaagccca ggtgtccggc cagggcgact ctctgcacga gcatatcgct aacctggccg    2280
gcagccccgc tatcaagaag ggcatcctgc agacagtgaa ggtggtggac gagctcgta    2340
aagtgatggg cagacacaag cccgagaaca tcgtgatcga gatggctaga gagaaccaga    2400
ccacccagaa gggacagaag aactcccgcg agaggatgaa gagaatcgaa gagggcatca    2460
aagagctggg cagccagatc ctgaaagaac accccgtgga aaacacccag ctgcagaacg    2520
agaagctgta cctgtactac ctgcagaatg gccgggatat gtacgtggac caggaactgg    2580
acatcaacag actgtccgac tacgatgtgg accatatcgt gcctcagagc tttctgaagg    2640
acgactccat cgataacaaa gtgctgactc ggagcgacaa gaacagaggc aagagcgaca    2700
acgtgccctc cgaagaggtc gtgaagaaga tgaagaacta ctggcgacag ctgctgaacg    2760
ccaagctgat tacccagagg aagttcgata acctgaccaa ggccgagaga ggcggcctga    2820
gcgagctgga taaggccggc ttcatcaaga gcagctggt ggaaaccaga cagatcacaa    2880
agcacgtggc acagatcctg gactcccgga tgaacactaa gtacgacgaa aacgataagc    2940
tgatccggga agtgaaagtg atcaccctga gtccaagct ggtgtccgat ttccggaagg    3000
atttccagtt ttacaaagtg cgcgagatca caactacca ccacgcccac gacgcctacc    3060
tgaacgccgt cgtgggaacc gccctgatca aaaagtaccc taagctggaa agcgagttcg    3120
tgtacggcga ctacaaggtg tacgacgtgc ggaagatgat cgccaagagc gagcaggaaa    3180
tcggcaaggc taccgccaag tacttcttct acagcaacat catgaacttt ttcaagaccg    3240
aaatcacct ggccaacggc gagatcagaa agcgccctct gatcgagaca aacggcgaaa    3300
ccggggagat cgtgtgggat aagggcagag acttcgccac agtgcgaaag gtgctgagca    3360
tgccccaagt gaatatcgtg aaaaagaccg aggtgcagac aggcggcttc agcaaagagt    3420
ctatcctgcc caagaggaac agcgacaagc tgatcgccaa gaagaagac tgggacccca    3480
agaagtacgg cggcttcgac agccctaccg tggcctactc tgtgctggtg gtggctaagg    3540
tggaaaaggg caagtccaag aaactgaaga gtgtgaaaga gctgctgggg atcaccatca    3600
tggaaagag cagctttgag aagaacccta tcgactttct ggaagccaag ggctacaaag    3660
aagtgaaaaa ggacctgatc atcaagctgc ctaagtactc cctgttcgag ctggaaaacg    3720
gcagaaagag aatgctggcc tctgccggcg aactgcagaa gggaaacgag ctggccctgc    3780
```

-continued

```
ctagcaaata tgtgaacttc ctgtacctgg cctcccacta tgagaagctg aagggcagcc   3840
ctgaggacaa cgaacagaaa cagctgtttg tggaacagca taagcactac ctggacgaga   3900
tcatcgagca gatcagcgag ttctccaaga gagtgatcct ggccgacgcc aatctggaca   3960
aggtgctgtc tgcctacaac aagcacaggg acaagcctat cagagagcag gccgagaata   4020
tcatccacct gttcaccctg acaaacctgg gcgctcctgc cgccttcaag tactttgaca   4080
ccaccatcga ccggaagagg tacaccagca ccaaagaggt gctggacgcc accctgatcc   4140
accagagcat caccggcctg tacgagacaa gaatcgacct gtctcagctg ggaggcgaca   4200
agagacctgc cgccactaag aaggccggac aggccaaaaa gaagaagtga gcggccgctt   4260
aattaagctg ccttctgcgg ggcttgcctt ctggccatgc ccttcttctc tcccttgcac   4320
ctgtacctct tggtctttga ataaagctg agtaggaagt ctagaaaaa aaaaaaaaa   4380
aaaaaaaaaa aaaaaaaaa aaaaaaaaa aaaaaaaaa aaaaaaaaa aaaaaaaaa   4440
aaaa                                                            4444
```

```
SEQ ID NO: 52          moltype = RNA   length = 4506
FEATURE                Location/Qualifiers
misc_feature           1..4506
                       note = Synthetic
source                 1..4506
                       mol_type = other RNA
                       organism = synthetic construct
modified_base          9
                       mod_base = m1f
modified_base          27
                       mod_base = m1f
modified_base          37
                       mod_base = m1f
modified_base          39
                       mod_base = m1f
modified_base          51
                       mod_base = m1f
modified_base          58
                       mod_base = m1f
modified_base          75
                       mod_base = m1f
modified_base          81
                       mod_base = m1f
modified_base          82
                       mod_base = m1f
modified_base          90
                       mod_base = m1f
modified_base          110
                       mod_base = m1f
modified_base          113
                       mod_base = m1f
modified_base          117
                       mod_base = m1f
modified_base          118
                       mod_base = m1f
modified_base          123
                       mod_base = m1f
modified_base          124
                       mod_base = m1f
modified_base          127
                       mod_base = m1f
modified_base          129
                       mod_base = m1f
modified_base          130
                       mod_base = m1f
modified_base          140
                       mod_base = m1f
modified_base          144
                       mod_base = m1f
modified_base          148
                       mod_base = m1f
modified_base          149
                       mod_base = m1f
modified_base          156
                       mod_base = m1f
modified_base          159
                       mod_base = m1f
modified_base          163
                       mod_base = m1f
modified_base          170
                       mod_base = m1f
modified_base          177
                       mod_base = m1f
modified_base          182
                       mod_base = m1f
modified_base          191
```

-continued

|                |                        |
| -------------- | ---------------------- |
|                | mod_base = m1f         |
| modified_base  | 192                    |
|                | mod_base = m1f         |
| modified_base  | 198                    |
|                | mod_base = m1f         |
| modified_base  | 201                    |
|                | mod_base = m1f         |
| modified_base  | 211                    |
|                | mod_base = m1f         |
| modified_base  | 221                    |
|                | mod_base = m1f         |
| modified_base  | 225                    |
|                | mod_base = m1f         |
| modified_base  | 226                    |
|                | mod_base = m1f         |
| modified_base  | 237                    |
|                | mod_base = m1f         |
| modified_base  | 240                    |
|                | mod_base = m1f         |
| modified_base  | 241                    |
|                | mod_base = m1f         |
| modified_base  | 249                    |
|                | mod_base = m1f         |
| modified_base  | 252                    |
|                | mod_base = m1f         |
| modified_base  | 254                    |
|                | mod_base = m1f         |
| modified_base  | 255                    |
|                | mod_base = m1f         |
| modified_base  | 260                    |
|                | mod_base = m1f         |
| modified_base  | 280                    |
|                | mod_base = m1f         |
| modified_base  | 288                    |
|                | mod_base = m1f         |
| modified_base  | 298                    |
|                | mod_base = m1f         |
| modified_base  | 311                    |
|                | mod_base = m1f         |
| modified_base  | 333                    |
|                | mod_base = m1f         |
| modified_base  | 334                    |
|                | mod_base = m1f         |
| modified_base  | 335                    |
|                | mod_base = m1f         |
| modified_base  | 338                    |
|                | mod_base = m1f         |
| modified_base  | 342                    |
|                | mod_base = m1f         |
| modified_base  | 351                    |
|                | mod_base = m1f         |
| modified_base  | 353                    |
|                | mod_base = m1f         |
| modified_base  | 354                    |
|                | mod_base = m1f         |
| modified_base  | 366                    |
|                | mod_base = m1f         |
| modified_base  | 375                    |
|                | mod_base = m1f         |
| modified_base  | 382                    |
|                | mod_base = m1f         |
| modified_base  | 383                    |
|                | mod_base = m1f         |
| modified_base  | 386                    |
|                | mod_base = m1f         |
| modified_base  | 387                    |
|                | mod_base = m1f         |
| modified_base  | 389                    |
|                | mod_base = m1f         |
| modified_base  | 390                    |
|                | mod_base = m1f         |
| modified_base  | 394                    |
|                | mod_base = m1f         |
| modified_base  | 399                    |
|                | mod_base = m1f         |
| modified_base  | 410                    |
|                | mod_base = m1f         |
| modified_base  | 411                    |
|                | mod_base = m1f         |

-continued

| | | |
|---|---|---|
| modified_base | 414 | |
| | mod_base = m1f | |
| modified_base | 417 | |
| | mod_base = m1f | |
| modified_base | 450 | |
| | mod_base = m1f | |
| modified_base | 451 | |
| | mod_base = m1f | |
| modified_base | 452 | |
| | mod_base = m1f | |
| modified_base | 453 | |
| | mod_base = m1f | |
| modified_base | 462 | |
| | mod_base = m1f | |
| modified_base | 465 | |
| | mod_base = m1f | |
| modified_base | 469 | |
| | mod_base = m1f | |
| modified_base | 474 | |
| | mod_base = m1f | |
| modified_base | 479 | |
| | mod_base = m1f | |
| modified_base | 491 | |
| | mod_base = m1f | |
| modified_base | 501 | |
| | mod_base = m1f | |
| modified_base | 503 | |
| | mod_base = m1f | |
| modified_base | 505 | |
| | mod_base = m1f | |
| modified_base | 508 | |
| | mod_base = m1f | |
| modified_base | 510 | |
| | mod_base = m1f | |
| modified_base | 511 | |
| | mod_base = m1f | |
| modified_base | 522 | |
| | mod_base = m1f | |
| modified_base | 525 | |
| | mod_base = m1f | |
| modified_base | 530 | |
| | mod_base = m1f | |
| modified_base | 538 | |
| | mod_base = m1f | |
| modified_base | 547 | |
| | mod_base = m1f | |
| modified_base | 549 | |
| | mod_base = m1f | |
| modified_base | 555 | |
| | mod_base = m1f | |
| modified_base | 558 | |
| | mod_base = m1f | |
| modified_base | 560 | |
| | mod_base = m1f | |
| modified_base | 563 | |
| | mod_base = m1f | |
| modified_base | 564 | |
| | mod_base = m1f | |
| modified_base | 570 | |
| | mod_base = m1f | |
| modified_base | 574 | |
| | mod_base = m1f | |
| modified_base | 579 | |
| | mod_base = m1f | |
| modified_base | 582 | |
| | mod_base = m1f | |
| modified_base | 583 | |
| | mod_base = m1f | |
| modified_base | 587 | |
| | mod_base = m1f | |
| modified_base | 588 | |
| | mod_base = m1f | |
| modified_base | 599 | |
| | mod_base = m1f | |
| modified_base | 600 | |
| | mod_base = m1f | |
| modified_base | 601 | |
| | mod_base = m1f | |
| modified_base | 603 | |

-continued

|                | mod_base = m1f |
|----------------|----------------|
| modified_base  | 606            |
|                | mod_base = m1f |
| modified_base  | 618            |
|                | mod_base = m1f |
| modified_base  | 622            |
|                | mod_base = m1f |
| modified_base  | 628            |
|                | mod_base = m1f |
| modified_base  | 632            |
|                | mod_base = m1f |
| modified_base  | 639            |
|                | mod_base = m1f |
| modified_base  | 643            |
|                | mod_base = m1f |
| modified_base  | 648            |
|                | mod_base = m1f |
| modified_base  | 650            |
|                | mod_base = m1f |
| modified_base  | 651            |
|                | mod_base = m1f |
| modified_base  | 654            |
|                | mod_base = m1f |
| modified_base  | 660            |
|                | mod_base = m1f |
| modified_base  | 663            |
|                | mod_base = m1f |
| modified_base  | 671            |
|                | mod_base = m1f |
| modified_base  | 681            |
|                | mod_base = m1f |
| modified_base  | 683            |
|                | mod_base = m1f |
| modified_base  | 684            |
|                | mod_base = m1f |
| modified_base  | 685            |
|                | mod_base = m1f |
| modified_base  | 694            |
|                | mod_base = m1f |
| modified_base  | 699            |
|                | mod_base = m1f |
| modified_base  | 714            |
|                | mod_base = m1f |
| modified_base  | 729            |
|                | mod_base = m1f |
| modified_base  | 732            |
|                | mod_base = m1f |
| modified_base  | 734            |
|                | mod_base = m1f |
| modified_base  | 744            |
|                | mod_base = m1f |
| modified_base  | 746            |
|                | mod_base = m1f |
| modified_base  | 752            |
|                | mod_base = m1f |
| modified_base  | 762            |
|                | mod_base = m1f |
| modified_base  | 769            |
|                | mod_base = m1f |
| modified_base  | 771            |
|                | mod_base = m1f |
| modified_base  | 774            |
|                | mod_base = m1f |
| modified_base  | 783            |
|                | mod_base = m1f |
| modified_base  | 787            |
|                | mod_base = m1f |
| modified_base  | 807            |
|                | mod_base = m1f |
| modified_base  | 809            |
|                | mod_base = m1f |
| modified_base  | 810            |
|                | mod_base = m1f |
| modified_base  | 817            |
|                | mod_base = m1f |
| modified_base  | 819            |
|                | mod_base = m1f |
| modified_base  | 822            |
|                | mod_base = m1f |

-continued

| modified_base | 823 |
| | mod_base = m1f |
| modified_base | 826 |
| | mod_base = m1f |
| modified_base | 828 |
| | mod_base = m1f |
| modified_base | 830 |
| | mod_base = m1f |
| modified_base | 834 |
| | mod_base = m1f |
| modified_base | 840 |
| | mod_base = m1f |
| modified_base | 844 |
| | mod_base = m1f |
| modified_base | 851 |
| | mod_base = m1f |
| modified_base | 852 |
| | mod_base = m1f |
| modified_base | 857 |
| | mod_base = m1f |
| modified_base | 863 |
| | mod_base = m1f |
| modified_base | 864 |
| | mod_base = m1f |
| modified_base | 870 |
| | mod_base = m1f |
| modified_base | 883 |
| | mod_base = m1f |
| modified_base | 888 |
| | mod_base = m1f |
| modified_base | 894 |
| | mod_base = m1f |
| modified_base | 896 |
| | mod_base = m1f |
| modified_base | 908 |
| | mod_base = m1f |
| modified_base | 913 |
| | mod_base = m1f |
| modified_base | 919 |
| | mod_base = m1f |
| modified_base | 921 |
| | mod_base = m1f |
| modified_base | 925 |
| | mod_base = m1f |
| modified_base | 930 |
| | mod_base = m1f |
| modified_base | 931 |
| | mod_base = m1f |
| modified_base | 933 |
| | mod_base = m1f |
| modified_base | 942 |
| | mod_base = m1f |
| modified_base | 949 |
| | mod_base = m1f |
| modified_base | 953 |
| | mod_base = m1f |
| modified_base | 961 |
| | mod_base = m1f |
| modified_base | 963 |
| | mod_base = m1f |
| modified_base | 965 |
| | mod_base = m1f |
| modified_base | 966 |
| | mod_base = m1f |
| modified_base | 969 |
| | mod_base = m1f |
| modified_base | 983 |
| | mod_base = m1f |
| modified_base | 984 |
| | mod_base = m1f |
| modified_base | 986 |
| | mod_base = m1f |
| modified_base | 991 |
| | mod_base = m1f |
| modified_base | 994 |
| | mod_base = m1f |
| modified_base | 996 |
| | mod_base = m1f |
| modified_base | 997 |

-continued

| | |
|---|---|
| | mod_base = m1f |
| modified_base | 999 |
| | mod_base = m1f |
| modified_base | 1002 |
| | mod_base = m1f |
| modified_base | 1011 |
| | mod_base = m1f |
| modified_base | 1012 |
| | mod_base = m1f |
| modified_base | 1014 |
| | mod_base = m1f |
| modified_base | 1020 |
| | mod_base = m1f |
| modified_base | 1024 |
| | mod_base = m1f |
| modified_base | 1027 |
| | mod_base = m1f |
| modified_base | 1032 |
| | mod_base = m1f |
| modified_base | 1047 |
| | mod_base = m1f |
| modified_base | 1049 |
| | mod_base = m1f |
| modified_base | 1059 |
| | mod_base = m1f |
| modified_base | 1062 |
| | mod_base = m1f |
| modified_base | 1070 |
| | mod_base = m1f |
| modified_base | 1092 |
| | mod_base = m1f |
| modified_base | 1096 |
| | mod_base = m1f |
| modified_base | 1098 |
| | mod_base = m1f |
| modified_base | 1101 |
| | mod_base = m1f |
| modified_base | 1110 |
| | mod_base = m1f |
| modified_base | 1113 |
| | mod_base = m1f |
| modified_base | 1125 |
| | mod_base = m1f |
| modified_base | 1129 |
| | mod_base = m1f |
| modified_base | 1136 |
| | mod_base = m1f |
| modified_base | 1146 |
| | mod_base = m1f |
| modified_base | 1147 |
| | mod_base = m1f |
| modified_base | 1148 |
| | mod_base = m1f |
| modified_base | 1149 |
| | mod_base = m1f |
| modified_base | 1151 |
| | mod_base = m1f |
| modified_base | 1152 |
| | mod_base = m1f |
| modified_base | 1160 |
| | mod_base = m1f |
| modified_base | 1172 |
| | mod_base = m1f |
| modified_base | 1181 |
| | mod_base = m1f |
| modified_base | 1185 |
| | mod_base = m1f |
| modified_base | 1186 |
| | mod_base = m1f |
| modified_base | 1211 |
| | mod_base = m1f |
| modified_base | 1212 |
| | mod_base = m1f |
| modified_base | 1213 |
| | mod_base = m1f |
| modified_base | 1214 |
| | mod_base = m1f |
| modified_base | 1220 |
| | mod_base = m1f |

-continued

| modified_base | 1221 |
| | mod_base = m1f |
| modified_base | 1224 |
| | mod_base = m1f |
| modified_base | 1233 |
| | mod_base = m1f |
| modified_base | 1234 |
| | mod_base = m1f |
| modified_base | 1236 |
| | mod_base = m1f |
| modified_base | 1245 |
| | mod_base = m1f |
| modified_base | 1262 |
| | mod_base = m1f |
| modified_base | 1263 |
| | mod_base = m1f |
| modified_base | 1266 |
| | mod_base = m1f |
| modified_base | 1269 |
| | mod_base = m1f |
| modified_base | 1275 |
| | mod_base = m1f |
| modified_base | 1288 |
| | mod_base = m1f |
| modified_base | 1290 |
| | mod_base = m1f |
| modified_base | 1293 |
| | mod_base = m1f |
| modified_base | 1310 |
| | mod_base = m1f |
| modified_base | 1311 |
| | mod_base = m1f |
| modified_base | 1321 |
| | mod_base = m1f |
| modified_base | 1322 |
| | mod_base = m1f |
| modified_base | 1326 |
| | mod_base = m1f |
| modified_base | 1338 |
| | mod_base = m1f |
| modified_base | 1344 |
| | mod_base = m1f |
| modified_base | 1352 |
| | mod_base = m1f |
| modified_base | 1353 |
| | mod_base = m1f |
| modified_base | 1362 |
| | mod_base = m1f |
| modified_base | 1365 |
| | mod_base = m1f |
| modified_base | 1381 |
| | mod_base = m1f |
| modified_base | 1382 |
| | mod_base = m1f |
| modified_base | 1383 |
| | mod_base = m1f |
| modified_base | 1385 |
| | mod_base = m1f |
| modified_base | 1391 |
| | mod_base = m1f |
| modified_base | 1392 |
| | mod_base = m1f |
| modified_base | 1394 |
| | mod_base = m1f |
| modified_base | 1395 |
| | mod_base = m1f |
| modified_base | 1405 |
| | mod_base = m1f |
| modified_base | 1416 |
| | mod_base = m1f |
| modified_base | 1425 |
| | mod_base = m1f |
| modified_base | 1427 |
| | mod_base = m1f |
| modified_base | 1428 |
| | mod_base = m1f |
| modified_base | 1432 |
| | mod_base = m1f |
| modified_base | 1433 |

|                |                       |
| -------------- | --------------------- |
|                | mod_base = m1f        |
| modified_base  | 1434                  |
|                | mod_base = m1f        |
| modified_base  | 1440                  |
|                | mod_base = m1f        |
| modified_base  | 1445                  |
|                | mod_base = m1f        |
| modified_base  | 1448                  |
|                | mod_base = m1f        |
| modified_base  | 1452                  |
|                | mod_base = m1f        |
| modified_base  | 1459                  |
|                | mod_base = m1f        |
| modified_base  | 1461                  |
|                | mod_base = m1f        |
| modified_base  | 1475                  |
|                | mod_base = m1f        |
| modified_base  | 1481                  |
|                | mod_base = m1f        |
| modified_base  | 1482                  |
|                | mod_base = m1f        |
| modified_base  | 1486                  |
|                | mod_base = m1f        |
| modified_base  | 1487                  |
|                | mod_base = m1f        |
| modified_base  | 1491                  |
|                | mod_base = m1f        |
| modified_base  | 1502                  |
|                | mod_base = m1f        |
| modified_base  | 1515                  |
|                | mod_base = m1f        |
| modified_base  | 1516                  |
|                | mod_base = m1f        |
| modified_base  | 1523                  |
|                | mod_base = m1f        |
| modified_base  | 1529                  |
|                | mod_base = m1f        |
| modified_base  | 1530                  |
|                | mod_base = m1f        |
| modified_base  | 1539                  |
|                | mod_base = m1f        |
| modified_base  | 1542                  |
|                | mod_base = m1f        |
| modified_base  | 1556                  |
|                | mod_base = m1f        |
| modified_base  | 1568                  |
|                | mod_base = m1f        |
| modified_base  | 1569                  |
|                | mod_base = m1f        |
| modified_base  | 1572                  |
|                | mod_base = m1f        |
| modified_base  | 1581                  |
|                | mod_base = m1f        |
| modified_base  | 1588                  |
|                | mod_base = m1f        |
| modified_base  | 1589                  |
|                | mod_base = m1f        |
| modified_base  | 1590                  |
|                | mod_base = m1f        |
| modified_base  | 1602                  |
|                | mod_base = m1f        |
| modified_base  | 1617                  |
|                | mod_base = m1f        |
| modified_base  | 1620                  |
|                | mod_base = m1f        |
| modified_base  | 1631                  |
|                | mod_base = m1f        |
| modified_base  | 1635                  |
|                | mod_base = m1f        |
| modified_base  | 1638                  |
|                | mod_base = m1f        |
| modified_base  | 1640                  |
|                | mod_base = m1f        |
| modified_base  | 1646                  |
|                | mod_base = m1f        |
| modified_base  | 1649                  |
|                | mod_base = m1f        |
| modified_base  | 1650                  |
|                | mod_base = m1f        |

| modified_base | 1656 |
| | mod_base = m1f |
| modified_base | 1658 |
| | mod_base = m1f |
| modified_base | 1668 |
| | mod_base = m1f |
| modified_base | 1672 |
| | mod_base = m1f |
| modified_base | 1677 |
| | mod_base = m1f |
| modified_base | 1682 |
| | mod_base = m1f |
| modified_base | 1686 |
| | mod_base = m1f |
| modified_base | 1690 |
| | mod_base = m1f |
| modified_base | 1698 |
| | mod_base = m1f |
| modified_base | 1712 |
| | mod_base = m1f |
| modified_base | 1713 |
| | mod_base = m1f |
| modified_base | 1716 |
| | mod_base = m1f |
| modified_base | 1718 |
| | mod_base = m1f |
| modified_base | 1740 |
| | mod_base = m1f |
| modified_base | 1743 |
| | mod_base = m1f |
| modified_base | 1748 |
| | mod_base = m1f |
| modified_base | 1749 |
| | mod_base = m1f |
| modified_base | 1752 |
| | mod_base = m1f |
| modified_base | 1753 |
| | mod_base = m1f |
| modified_base | 1754 |
| | mod_base = m1f |
| modified_base | 1755 |
| | mod_base = m1f |
| modified_base | 1762 |
| | mod_base = m1f |
| modified_base | 1773 |
| | mod_base = m1f |
| modified_base | 1777 |
| | mod_base = m1f |
| modified_base | 1779 |
| | mod_base = m1f |
| modified_base | 1788 |
| | mod_base = m1f |
| modified_base | 1799 |
| | mod_base = m1f |
| modified_base | 1802 |
| | mod_base = m1f |
| modified_base | 1803 |
| | mod_base = m1f |
| modified_base | 1812 |
| | mod_base = m1f |
| modified_base | 1817 |
| | mod_base = m1f |
| modified_base | 1819 |
| | mod_base = m1f |
| modified_base | 1820 |
| | mod_base = m1f |
| modified_base | 1821 |
| | mod_base = m1f |
| modified_base | 1826 |
| | mod_base = m1f |
| modified_base | 1830 |
| | mod_base = m1f |
| modified_base | 1836 |
| | mod_base = m1f |
| modified_base | 1838 |
| | mod_base = m1f |
| modified_base | 1843 |
| | mod_base = m1f |
| modified_base | 1845 |

-continued

|  |  |
|---|---|
|  | mod_base = m1f |
| modified_base | 1856 |
|  | mod_base = m1f |
| modified_base | 1857 |
|  | mod_base = m1f |
| modified_base | 1865 |
|  | mod_base = m1f |
| modified_base | 1869 |
|  | mod_base = m1f |
| modified_base | 1876 |
|  | mod_base = m1f |
| modified_base | 1877 |
|  | mod_base = m1f |
| modified_base | 1885 |
|  | mod_base = m1f |
| modified_base | 1887 |
|  | mod_base = m1f |
| modified_base | 1890 |
|  | mod_base = m1f |
| modified_base | 1896 |
|  | mod_base = m1f |
| modified_base | 1899 |
|  | mod_base = m1f |
| modified_base | 1913 |
|  | mod_base = m1f |
| modified_base | 1914 |
|  | mod_base = m1f |
| modified_base | 1917 |
|  | mod_base = m1f |
| modified_base | 1921 |
|  | mod_base = m1f |
| modified_base | 1933 |
|  | mod_base = m1f |
| modified_base | 1941 |
|  | mod_base = m1f |
| modified_base | 1944 |
|  | mod_base = m1f |
| modified_base | 1951 |
|  | mod_base = m1f |
| modified_base | 1953 |
|  | mod_base = m1f |
| modified_base | 1956 |
|  | mod_base = m1f |
| modified_base | 1959 |
|  | mod_base = m1f |
| modified_base | 1965 |
|  | mod_base = m1f |
| modified_base | 1970 |
|  | mod_base = m1f |
| modified_base | 1971 |
|  | mod_base = m1f |
| modified_base | 1973 |
|  | mod_base = m1f |
| modified_base | 1974 |
|  | mod_base = m1f |
| modified_base | 1981 |
|  | mod_base = m1f |
| modified_base | 1989 |
|  | mod_base = m1f |
| modified_base | 1992 |
|  | mod_base = m1f |
| modified_base | 2004 |
|  | mod_base = m1f |
| modified_base | 2012 |
|  | mod_base = m1f |
| modified_base | 2022 |
|  | mod_base = m1f |
| modified_base | 2024 |
|  | mod_base = m1f |
| modified_base | 2025 |
|  | mod_base = m1f |
| modified_base | 2026 |
|  | mod_base = m1f |
| modified_base | 2037 |
|  | mod_base = m1f |
| modified_base | 2040 |
|  | mod_base = m1f |
| modified_base | 2049 |
|  | mod_base = m1f |

-continued

| modified_base | 2063 |
| | mod_base = m1f |
| modified_base | 2065 |
| | mod_base = m1f |
| modified_base | 2072 |
| | mod_base = m1f |
| modified_base | 2077 |
| | mod_base = m1f |
| modified_base | 2082 |
| | mod_base = m1f |
| modified_base | 2084 |
| | mod_base = m1f |
| modified_base | 2094 |
| | mod_base = m1f |
| modified_base | 2097 |
| | mod_base = m1f |
| modified_base | 2106 |
| | mod_base = m1f |
| modified_base | 2120 |
| | mod_base = m1f |
| modified_base | 2133 |
| | mod_base = m1f |
| modified_base | 2136 |
| | mod_base = m1f |
| modified_base | 2141 |
| | mod_base = m1f |
| modified_base | 2142 |
| | mod_base = m1f |
| modified_base | 2145 |
| | mod_base = m1f |
| modified_base | 2146 |
| | mod_base = m1f |
| modified_base | 2150 |
| | mod_base = m1f |
| modified_base | 2159 |
| | mod_base = m1f |
| modified_base | 2160 |
| | mod_base = m1f |
| modified_base | 2174 |
| | mod_base = m1f |
| modified_base | 2175 |
| | mod_base = m1f |
| modified_base | 2178 |
| | mod_base = m1f |
| modified_base | 2184 |
| | mod_base = m1f |
| modified_base | 2185 |
| | mod_base = m1f |
| modified_base | 2187 |
| | mod_base = m1f |
| modified_base | 2198 |
| | mod_base = m1f |
| modified_base | 2202 |
| | mod_base = m1f |
| modified_base | 2207 |
| | mod_base = m1f |
| modified_base | 2208 |
| | mod_base = m1f |
| modified_base | 2218 |
| | mod_base = m1f |
| modified_base | 2220 |
| | mod_base = m1f |
| modified_base | 2235 |
| | mod_base = m1f |
| modified_base | 2237 |
| | mod_base = m1f |
| modified_base | 2252 |
| | mod_base = m1f |
| modified_base | 2256 |
| | mod_base = m1f |
| modified_base | 2257 |
| | mod_base = m1f |
| modified_base | 2260 |
| | mod_base = m1f |
| modified_base | 2268 |
| | mod_base = m1f |
| modified_base | 2272 |
| | mod_base = m1f |
| modified_base | 2277 |

-continued

|                 |                        |
|-----------------|------------------------|
|                 | mod_base = m1f         |
| modified_base   | 2285                   |
|                 | mod_base = m1f         |
| modified_base   | 2295                   |
|                 | mod_base = m1f         |
| modified_base   | 2307                   |
|                 | mod_base = m1f         |
| modified_base   | 2308                   |
|                 | mod_base = m1f         |
| modified_base   | 2310                   |
|                 | mod_base = m1f         |
| modified_base   | 2319                   |
|                 | mod_base = m1f         |
| modified_base   | 2325                   |
|                 | mod_base = m1f         |
| modified_base   | 2328                   |
|                 | mod_base = m1f         |
| modified_base   | 2332                   |
|                 | mod_base = m1f         |
| modified_base   | 2337                   |
|                 | mod_base = m1f         |
| modified_base   | 2340                   |
|                 | mod_base = m1f         |
| modified_base   | 2346                   |
|                 | mod_base = m1f         |
| modified_base   | 2349                   |
|                 | mod_base = m1f         |
| modified_base   | 2359                   |
|                 | mod_base = m1f         |
| modified_base   | 2373                   |
|                 | mod_base = m1f         |
| modified_base   | 2376                   |
|                 | mod_base = m1f         |
| modified_base   | 2379                   |
|                 | mod_base = m1f         |
| modified_base   | 2385                   |
|                 | mod_base = m1f         |
| modified_base   | 2404                   |
|                 | mod_base = m1f         |
| modified_base   | 2426                   |
|                 | mod_base = m1f         |
| modified_base   | 2439                   |
|                 | mod_base = m1f         |
| modified_base   | 2448                   |
|                 | mod_base = m1f         |
| modified_base   | 2449                   |
|                 | mod_base = m1f         |
| modified_base   | 2460                   |
|                 | mod_base = m1f         |
| modified_base   | 2469                   |
|                 | mod_base = m1f         |
| modified_base   | 2481                   |
|                 | mod_base = m1f         |
| modified_base   | 2482                   |
|                 | mod_base = m1f         |
| modified_base   | 2484                   |
|                 | mod_base = m1f         |
| modified_base   | 2494                   |
|                 | mod_base = m1f         |
| modified_base   | 2499                   |
|                 | mod_base = m1f         |
| modified_base   | 2514                   |
|                 | mod_base = m1f         |
| modified_base   | 2529                   |
|                 | mod_base = m1f         |
| modified_base   | 2531                   |
|                 | mod_base = m1f         |
| modified_base   | 2533                   |
|                 | mod_base = m1f         |
| modified_base   | 2534                   |
|                 | mod_base = m1f         |
| modified_base   | 2535                   |
|                 | mod_base = m1f         |
| modified_base   | 2537                   |
|                 | mod_base = m1f         |
| modified_base   | 2540                   |
|                 | mod_base = m1f         |
| modified_base   | 2542                   |
|                 | mod_base = m1f         |

-continued

| modified_base | 2544 |
| | mod_base = m1f |
| modified_base | 2560 |
| | mod_base = m1f |
| modified_base | 2562 |
| | mod_base = m1f |
| modified_base | 2564 |
| | mod_base = m1f |
| modified_base | 2568 |
| | mod_base = m1f |
| modified_base | 2572 |
| | mod_base = m1f |
| modified_base | 2580 |
| | mod_base = m1f |
| modified_base | 2586 |
| | mod_base = m1f |
| modified_base | 2587 |
| | mod_base = m1f |
| modified_base | 2595 |
| | mod_base = m1f |
| modified_base | 2603 |
| | mod_base = m1f |
| modified_base | 2605 |
| | mod_base = m1f |
| modified_base | 2610 |
| | mod_base = m1f |
| modified_base | 2614 |
| | mod_base = m1f |
| modified_base | 2619 |
| | mod_base = m1f |
| modified_base | 2620 |
| | mod_base = m1f |
| modified_base | 2622 |
| | mod_base = m1f |
| modified_base | 2626 |
| | mod_base = m1f |
| modified_base | 2633 |
| | mod_base = m1f |
| modified_base | 2634 |
| | mod_base = m1f |
| modified_base | 2637 |
| | mod_base = m1f |
| modified_base | 2648 |
| | mod_base = m1f |
| modified_base | 2652 |
| | mod_base = m1f |
| modified_base | 2653 |
| | mod_base = m1f |
| modified_base | 2664 |
| | mod_base = m1f |
| modified_base | 2667 |
| | mod_base = m1f |
| modified_base | 2696 |
| | mod_base = m1f |
| modified_base | 2701 |
| | mod_base = m1f |
| modified_base | 2704 |
| | mod_base = m1f |
| modified_base | 2706 |
| | mod_base = m1f |
| modified_base | 2711 |
| | mod_base = m1f |
| modified_base | 2721 |
| | mod_base = m1f |
| modified_base | 2724 |
| | mod_base = m1f |
| modified_base | 2733 |
| | mod_base = m1f |
| modified_base | 2740 |
| | mod_base = m1f |
| modified_base | 2741 |
| | mod_base = m1f |
| modified_base | 2744 |
| | mod_base = m1f |
| modified_base | 2754 |
| | mod_base = m1f |
| modified_base | 2757 |
| | mod_base = m1f |
| modified_base | 2761 |

-continued

| | |
|---|---|
| | mod_base = m1f |
| modified_base | 2769 |
| | mod_base = m1f |
| modified_base | 2772 |
| | mod_base = m1f |
| modified_base | 2773 |
| | mod_base = m1f |
| modified_base | 2786 |
| | mod_base = m1f |
| modified_base | 2787 |
| | mod_base = m1f |
| modified_base | 2791 |
| | mod_base = m1f |
| modified_base | 2796 |
| | mod_base = m1f |
| modified_base | 2815 |
| | mod_base = m1f |
| modified_base | 2820 |
| | mod_base = m1f |
| modified_base | 2822 |
| | mod_base = m1f |
| modified_base | 2829 |
| | mod_base = m1f |
| modified_base | 2839 |
| | mod_base = m1f |
| modified_base | 2843 |
| | mod_base = m1f |
| modified_base | 2844 |
| | mod_base = m1f |
| modified_base | 2847 |
| | mod_base = m1f |
| modified_base | 2859 |
| | mod_base = m1f |
| modified_base | 2862 |
| | mod_base = m1f |
| modified_base | 2877 |
| | mod_base = m1f |
| modified_base | 2889 |
| | mod_base = m1f |
| modified_base | 2898 |
| | mod_base = m1f |
| modified_base | 2899 |
| | mod_base = m1f |
| modified_base | 2901 |
| | mod_base = m1f |
| modified_base | 2913 |
| | mod_base = m1f |
| modified_base | 2920 |
| | mod_base = m1f |
| modified_base | 2924 |
| | mod_base = m1f |
| modified_base | 2938 |
| | mod_base = m1f |
| modified_base | 2943 |
| | mod_base = m1f |
| modified_base | 2946 |
| | mod_base = m1f |
| modified_base | 2955 |
| | mod_base = m1f |
| modified_base | 2961 |
| | mod_base = m1f |
| modified_base | 2964 |
| | mod_base = m1f |
| modified_base | 2970 |
| | mod_base = m1f |
| modified_base | 2975 |
| | mod_base = m1f |
| modified_base | 2982 |
| | mod_base = m1f |
| modified_base | 2985 |
| | mod_base = m1f |
| modified_base | 2987 |
| | mod_base = m1f |
| modified_base | 2993 |
| | mod_base = m1f |
| modified_base | 2994 |
| | mod_base = m1f |
| modified_base | 2995 |
| | mod_base = m1f |

-continued

```
modified_base       3004
                    mod_base = m1f
modified_base       3005
                    mod_base = m1f
modified_base       3006
                    mod_base = m1f
modified_base       3011
                    mod_base = m1f
modified_base       3012
                    mod_base = m1f
modified_base       3013
                    mod_base = m1f
modified_base       3014
                    mod_base = m1f
modified_base       3021
                    mod_base = m1f
modified_base       3030
                    mod_base = m1f
modified_base       3038
                    mod_base = m1f
modified_base       3043
                    mod_base = m1f
modified_base       3059
                    mod_base = m1f
modified_base       3063
                    mod_base = m1f
modified_base       3064
                    mod_base = m1f
modified_base       3072
                    mod_base = m1f
modified_base       3075
                    mod_base = m1f
modified_base       3085
                    mod_base = m1f
modified_base       3087
                    mod_base = m1f
modified_base       3088
                    mod_base = m1f
modified_base       3090
                    mod_base = m1f
modified_base       3098
                    mod_base = m1f
modified_base       3108
                    mod_base = m1f
modified_base       3113
                    mod_base = m1f
modified_base       3119
                    mod_base = m1f
modified_base       3120
                    mod_base = m1f
modified_base       3121
                    mod_base = m1f
modified_base       3123
                    mod_base = m1f
modified_base       3125
                    mod_base = m1f
modified_base       3134
                    mod_base = m1f
modified_base       3141
                    mod_base = m1f
modified_base       3143
                    mod_base = m1f
modified_base       3150
                    mod_base = m1f
modified_base       3159
                    mod_base = m1f
modified_base       3162
                    mod_base = m1f
modified_base       3170
                    mod_base = m1f
modified_base       3172
                    mod_base = m1f
modified_base       3183
                    mod_base = m1f
modified_base       3203
                    mod_base = m1f
modified_base       3206
                    mod_base = m1f
modified_base       3207
```

-continued

| | | mod_base = m1f |
|---|---|---|
| modified_base | 3209 | |
| | | mod_base = m1f |
| modified_base | 3210 | |
| | | mod_base = m1f |
| modified_base | 3212 | |
| | | mod_base = m1f |
| modified_base | 3215 | |
| | | mod_base = m1f |
| modified_base | 3222 | |
| | | mod_base = m1f |
| modified_base | 3223 | |
| | | mod_base = m1f |
| modified_base | 3225 | |
| | | mod_base = m1f |
| modified_base | 3229 | |
| | | mod_base = m1f |
| modified_base | 3230 | |
| | | mod_base = m1f |
| modified_base | 3231 | |
| | | mod_base = m1f |
| modified_base | 3232 | |
| | | mod_base = m1f |
| modified_base | 3233 | |
| | | mod_base = m1f |
| modified_base | 3234 | |
| | | mod_base = m1f |
| modified_base | 3241 | |
| | | mod_base = m1f |
| modified_base | 3246 | |
| | | mod_base = m1f |
| modified_base | 3247 | |
| | | mod_base = m1f |
| modified_base | 3252 | |
| | | mod_base = m1f |
| modified_base | 3256 | |
| | | mod_base = m1f |
| modified_base | 3267 | |
| | | mod_base = m1f |
| modified_base | 3268 | |
| | | mod_base = m1f |
| modified_base | 3282 | |
| | | mod_base = m1f |
| modified_base | 3285 | |
| | | mod_base = m1f |
| modified_base | 3286 | |
| | | mod_base = m1f |
| modified_base | 3304 | |
| | | mod_base = m1f |
| modified_base | 3312 | |
| | | mod_base = m1f |
| modified_base | 3313 | |
| | | mod_base = m1f |
| modified_base | 3315 | |
| | | mod_base = m1f |
| modified_base | 3317 | |
| | | mod_base = m1f |
| modified_base | 3335 | |
| | | mod_base = m1f |
| modified_base | 3336 | |
| | | mod_base = m1f |
| modified_base | 3345 | |
| | | mod_base = m1f |
| modified_base | 3354 | |
| | | mod_base = m1f |
| modified_base | 3357 | |
| | | mod_base = m1f |
| modified_base | 3359 | |
| | | mod_base = m1f |
| modified_base | 3363 | |
| | | mod_base = m1f |
| modified_base | 3372 | |
| | | mod_base = m1f |
| modified_base | 3378 | |
| | | mod_base = m1f |
| modified_base | 3381 | |
| | | mod_base = m1f |
| modified_base | 3396 | |
| | | mod_base = m1f |

-continued

| modified_base | 3410 |
| | mod_base = m1f |
| modified_base | 3411 |
| | mod_base = m1f |
| modified_base | 3413 |
| | mod_base = m1f |
| modified_base | 3422 |
| | mod_base = m1f |
| modified_base | 3426 |
| | mod_base = m1f |
| modified_base | 3429 |
| | mod_base = m1f |
| modified_base | 3433 |
| | mod_base = m1f |
| modified_base | 3453 |
| | mod_base = m1f |
| modified_base | 3456 |
| | mod_base = m1f |
| modified_base | 3457 |
| | mod_base = m1f |
| modified_base | 3473 |
| | mod_base = m1f |
| modified_base | 3488 |
| | mod_base = m1f |
| modified_base | 3497 |
| | mod_base = m1f |
| modified_base | 3498 |
| | mod_base = m1f |
| modified_base | 3499 |
| | mod_base = m1f |
| modified_base | 3502 |
| | mod_base = m1f |
| modified_base | 3503 |
| | mod_base = m1f |
| modified_base | 3508 |
| | mod_base = m1f |
| modified_base | 3513 |
| | mod_base = m1f |
| modified_base | 3518 |
| | mod_base = m1f |
| modified_base | 3521 |
| | mod_base = m1f |
| modified_base | 3525 |
| | mod_base = m1f |
| modified_base | 3528 |
| | mod_base = m1f |
| modified_base | 3531 |
| | mod_base = m1f |
| modified_base | 3534 |
| | mod_base = m1f |
| modified_base | 3543 |
| | mod_base = m1f |
| modified_base | 3557 |
| | mod_base = m1f |
| modified_base | 3567 |
| | mod_base = m1f |
| modified_base | 3572 |
| | mod_base = m1f |
| modified_base | 3576 |
| | mod_base = m1f |
| modified_base | 3585 |
| | mod_base = m1f |
| modified_base | 3586 |
| | mod_base = m1f |
| modified_base | 3587 |
| | mod_base = m1f |
| modified_base | 3588 |
| | mod_base = m1f |
| modified_base | 3592 |
| | mod_base = m1f |
| modified_base | 3594 |
| | mod_base = m1f |
| modified_base | 3600 |
| | mod_base = m1f |
| modified_base | 3603 |
| | mod_base = m1f |
| modified_base | 3611 |
| | mod_base = m1f |
| modified_base | 3614 |

-continued

```
                              mod_base = m1f
modified_base                 3617
                              mod_base = m1f
modified_base                 3618
                              mod_base = m1f
modified_base                 3633
                              mod_base = m1f
modified_base                 3637
                              mod_base = m1f
modified_base                 3638
                              mod_base = m1f
modified_base                 3639
                              mod_base = m1f
modified_base                 3642
                              mod_base = m1f
modified_base                 3649
                              mod_base = m1f
modified_base                 3655
                              mod_base = m1f
modified_base                 3656
                              mod_base = m1f
modified_base                 3658
                              mod_base = m1f
modified_base                 3666
                              mod_base = m1f
modified_base                 3678
                              mod_base = m1f
modified_base                 3681
                              mod_base = m1f
modified_base                 3682
                              mod_base = m1f
modified_base                 3684
                              mod_base = m1f
modified_base                 3690
                              mod_base = m1f
modified_base                 3698
                              mod_base = m1f
modified_base                 3701
                              mod_base = m1f
modified_base                 3705
                              mod_base = m1f
modified_base                 3707
                              mod_base = m1f
modified_base                 3708
                              mod_base = m1f
modified_base                 3714
                              mod_base = m1f
modified_base                 3724
                              mod_base = m1f
modified_base                 3735
                              mod_base = m1f
modified_base                 3738
                              mod_base = m1f
modified_base                 3756
                              mod_base = m1f
modified_base                 3774
                              mod_base = m1f
modified_base                 3780
                              mod_base = m1f
modified_base                 3785
                              mod_base = m1f
modified_base                 3791
                              mod_base = m1f
modified_base                 3795
                              mod_base = m1f
modified_base                 3800
                              mod_base = m1f
modified_base                 3801
                              mod_base = m1f
modified_base                 3804
                              mod_base = m1f
modified_base                 3806
                              mod_base = m1f
modified_base                 3810
                              mod_base = m1f
modified_base                 3811
                              mod_base = m1f
modified_base                 3815
                              mod_base = m1f
```

-continued

| | | |
|---|---|---|
| modified_base | 3820 | |
| | mod_base = m1f | |
| modified_base | 3821 | |
| | mod_base = m1f | |
| modified_base | 3831 | |
| | mod_base = m1f | |
| modified_base | 3839 | |
| | mod_base = m1f | |
| modified_base | 3867 | |
| | mod_base = m1f | |
| modified_base | 3868 | |
| | mod_base = m1f | |
| modified_base | 3869 | |
| | mod_base = m1f | |
| modified_base | 3870 | |
| | mod_base = m1f | |
| modified_base | 3873 | |
| | mod_base = m1f | |
| modified_base | 3889 | |
| | mod_base = m1f | |
| modified_base | 3890 | |
| | mod_base = m1f | |
| modified_base | 3893 | |
| | mod_base = m1f | |
| modified_base | 3894 | |
| | mod_base = m1f | |
| modified_base | 3903 | |
| | mod_base = m1f | |
| modified_base | 3906 | |
| | mod_base = m1f | |
| modified_base | 3915 | |
| | mod_base = m1f | |
| modified_base | 3916 | |
| | mod_base = m1f | |
| modified_base | 3917 | |
| | mod_base = m1f | |
| modified_base | 3923 | |
| | mod_base = m1f | |
| modified_base | 3924 | |
| | mod_base = m1f | |
| modified_base | 3926 | |
| | mod_base = m1f | |
| modified_base | 3936 | |
| | mod_base = m1f | |
| modified_base | 3939 | |
| | mod_base = m1f | |
| modified_base | 3942 | |
| | mod_base = m1f | |
| modified_base | 3955 | |
| | mod_base = m1f | |
| modified_base | 3957 | |
| | mod_base = m1f | |
| modified_base | 3966 | |
| | mod_base = m1f | |
| modified_base | 3969 | |
| | mod_base = m1f | |
| modified_base | 3971 | |
| | mod_base = m1f | |
| modified_base | 3977 | |
| | mod_base = m1f | |
| modified_base | 3982 | |
| | mod_base = m1f | |
| modified_base | 3988 | |
| | mod_base = m1f | |
| modified_base | 4000 | |
| | mod_base = m1f | |
| modified_base | 4002 | |
| | mod_base = m1f | |
| modified_base | 4023 | |
| | mod_base = m1f | |
| modified_base | 4026 | |
| | mod_base = m1f | |
| modified_base | 4030 | |
| | mod_base = m1f | |
| modified_base | 4032 | |
| | mod_base = m1f | |
| modified_base | 4034 | |
| | mod_base = m1f | |
| modified_base | 4035 | |

-continued

```
                              mod_base = m1f
modified_base                 4039
                              mod_base = m1f
modified_base                 4041
                              mod_base = m1f
modified_base                 4050
                              mod_base = m1f
modified_base                 4067
                              mod_base = m1f
modified_base                 4068
                              mod_base = m1f
modified_base                 4073
                              mod_base = m1f
modified_base                 4076
                              mod_base = m1f
modified_base                 4077
                              mod_base = m1f
modified_base                 4078
                              mod_base = m1f
modified_base                 4089
                              mod_base = m1f
modified_base                 4093
                              mod_base = m1f
modified_base                 4103
                              mod_base = m1f
modified_base                 4109
                              mod_base = m1f
modified_base                 4114
                              mod_base = m1f
modified_base                 4122
                              mod_base = m1f
modified_base                 4124
                              mod_base = m1f
modified_base                 4125
                              mod_base = m1f
modified_base                 4137
                              mod_base = m1f
modified_base                 4138
                              mod_base = m1f
modified_base                 4140
                              mod_base = m1f
modified_base                 4144
                              mod_base = m1f
modified_base                 4148
                              mod_base = m1f
modified_base                 4152
                              mod_base = m1f
modified_base                 4161
                              mod_base = m1f
modified_base                 4163
                              mod_base = m1f
modified_base                 4176
                              mod_base = m1f
modified_base                 4182
                              mod_base = m1f
modified_base                 4190
                              mod_base = m1f
modified_base                 4191
                              mod_base = m1f
modified_base                 4210
                              mod_base = m1f
modified_base                 4216
                              mod_base = m1f
modified_base                 4250
                              mod_base = m1f
modified_base                 4261
                              mod_base = m1f
modified_base                 4262
                              mod_base = m1f
modified_base                 4265
                              mod_base = m1f
modified_base                 4266
                              mod_base = m1f
modified_base                 4271
                              mod_base = m1f
modified_base                 4275
                              mod_base = m1f
modified_base                 4276
                              mod_base = m1f
```

```
modified_base          4278
                       mod_base = m1f
modified_base          4286
                       mod_base = m1f
modified_base          4287
                       mod_base = m1f
modified_base          4291
                       mod_base = m1f
modified_base          4292
                       mod_base = m1f
modified_base          4294
                       mod_base = m1f
modified_base          4300
                       mod_base = m1f
modified_base          4305
                       mod_base = m1f
modified_base          4306
                       mod_base = m1f
modified_base          4308
                       mod_base = m1f
modified_base          4309
                       mod_base = m1f
modified_base          4311
                       mod_base = m1f
modified_base          4313
                       mod_base = m1f
modified_base          4317
                       mod_base = m1f
modified_base          4318
                       mod_base = m1f
modified_base          4324
                       mod_base = m1f
modified_base          4326
                       mod_base = m1f
modified_base          4330
                       mod_base = m1f
modified_base          4332
                       mod_base = m1f
modified_base          4333
                       mod_base = m1f
modified_base          4336
                       mod_base = m1f
modified_base          4338
                       mod_base = m1f
modified_base          4339
                       mod_base = m1f
modified_base          4340
                       mod_base = m1f
modified_base          4344
                       mod_base = m1f
modified_base          4351
                       mod_base = m1f
modified_base          4355
                       mod_base = m1f
modified_base          4362
                       mod_base = m1f
modified_base          4364
                       mod_base = m1f
SEQUENCE: 52
agaggaaata agagagaaaa gaagagtaag aagaaatata agagccacca tggcccctaa    60
gaagaagaga aaagtcggaa ttcacggagt ccccgccgcc gacaaaaagt actccattgg   120
ccttgatatt ggaaccaact ccgtgggttg ggccgtgatc actgacgagt acaaggtgcc   180
gtccaagaag ttcaaggtgc tggggaacac tgaccggcac tcaattaaga agaacctgat   240
tggggcgctg ctgttcgact ccggagaaac cgcggaggct acccgcctga agcggactgc   300
ccggcggaga tacacgcgca ggaagaaccg gatttgctac ctccaagaaa tcttcagcaa   360
cgaaatggca aaggtggacg attccttctt ccatcgcctg gaagagagct tcctggtgga   420
agaggacaag aagcacgaaa gacacccgat tttcggcaac atcgtggatg aggtcgcata   480
ccacgaaaag taccccacca tctatcatct tcggaagaag ctggtcgact ccaccgataa   540
ggccgatctg cgcctgatct acttggcgct ggctcacatg attaagttca gaggacactt   600
tctgatagag ggcgacctca atccgataa ctccgacgtg gataagctgt tcatccaact   660
ggtgcagacg tacaaccaac tgtttgaaga gaatccaatc aacgccagcg gggtggacgc   720
caaggccatc ctgtccgccc ggctgtcaaa gtccagacgc ctggagaatc tcatcgcgca   780
actccctggc gaaaaaaga acggactctt cgggaatctg attgctctgt ccctggggct   840
cactccgaac ttcaagtcga acttcgacct ggcggaggac gctaagctgc agctgtccaa   900
ggacacctac gatgacgatc tggataacct tctggcccag atcggggatc aatacgccga   960
tctcttcctg gccgcaaaga acttgtcgga tgctattctg ctgagcgaca ttctgcgggt  1020
caatactgaa atcaccaagg cgccctgtc ggccagcatg atcaagcgct acgacgaaca  1080
ccaccaagac ctgactctgc tgaaggccct cgtgcgccag cagctgcctg aaaagtacaa  1140
ggagattttc ttcgaccagt ccaagaacgg atacgccgga tacattgacg gagggccag  1200
```

```
ccaggaggaa ttttacaaat tcatcaagcc cattctcgag aaaatggacg gaaccgaaga    1260
gttgctcgtg aagctgaaca gagaggatcc cctccggaag cagcggacct tcgacaacgg    1320
ttccatcccg caccaaatcc acctgggcga attgcacgcc atcctccggc ggcaggaaga    1380
tttctaccca ttcttgaagg acaatcgcga aaagatcgaa aagatcttga ctttccgcat    1440
cccgtactac gtgggccctc tggcccgcgg caactcccgc ttcgcttgga tgacacggaa    1500
gtccgaggaa accattacgc cctggaactt cgaggaagtg gtggacaagg gggcgtccgc    1560
ccagagcttc atcgaacgca tgaccaattt cgacaagaac ctcccgaacg aaaaagtgct    1620
gccaaagcac tcgctcctct acgaatactt caccgtgtac aacgagctga ctaaggtcaa    1680
atacgtgact gagggaatgc ggaagccggc cttcctgtcg ggagagcaga agaaggccat    1740
agtggacttg cttttcaaga ctaaccggaa ggtcactgtg aagcaactca aggaggacta    1800
cttcaagaag atcgagtgtt tcgactcggt ggagatctcg ggtgtcgagg accgcttcaa    1860
cgcctccctg ggaacttacc acgatctgct gaagatcatc aaggacaagg acttcctcga    1920
taacgaagaa aatgaggaca tcctcgagga tatcgtgctg accctgacct tgttcgagga    1980
tagggagatg atcgaggagc ggctcaagac ctacgcccac ctgtttgacg acaaagtgat    2040
gaagcaactg aaacggcgga ggtataccgg ctggggtcgg ctgtcccgca agctgatcaa    2100
cgggatcagg gacaagcagt ccggaaagac catcctcgac ttccttaagt ccgacggatt    2160
cgcgaaccgc aacttcatgc aacttatcca cgacgactcg ctgacattca aggaagatat    2220
ccagaaggcc caggtgtccg gacaggggga ctcgcttcat gagcacatcg ctaacctggc    2280
cggatccccc gccataaaaa agggcattct gcagaccgtc aaagtggtgg atgagctggt    2340
caaggtcatg ggccggcata gccggaaaa catcgtcatc gagatggccc gcgagaacca    2400
gactacgcag aagggccaga agaactcccg ggagcggatg aagcggattg aagagggcat    2460
caaggagctc ggcagccaga ttctgaagga acatcccgtg gaaaacaccc agctgcaaaa    2520
cgaaaagctc tatttgtact atctgcaaaa cggacgcgat atgtacgtgg atcaggagct    2580
ggacattaac agactgagcg actatgacgt ggatcacatt gtgcctcaaa gcttcctcaa    2640
ggacgactca attgacaaca aggtcctgac cagaagcgac aagaacagag gaaagtcgga    2700
taatgtgccg tccgaagaag tggtcaagaa gatgaagaat tactggagac agctcctgaa    2760
tgcgaagctc attcccagc ggaagttcga taacctgacc aaggccgaaa ggggtggact    2820
gtccgaactc gacaaagctg gcttcatcaa gcgccaactg gtcgaaacca ggcagatcac    2880
caagcacgtc gcccagattc tggacagccg catgaacact aagtacgacg agaacgataa    2940
gctgatccgc gaagtgaagg tcatcaccct gaagtccaag ctcgtgtccg actttcggaa    3000
ggatttccag ttttacaagg tccgcgagat caacaactac catcacgccc acgacgcgta    3060
ccttaacgca gtcgtgggaa cggctcttat caagaagtac ccaaagctgg agtcggaatt    3120
tgtgtacgga gactacaaag tgtacgacgt gcgcaagatg atcgccaaat ctgagcaaga    3180
gatcgggaag gcaaccgcca aatacttctt ctactcaaac attatgaatt ttttcaaaac    3240
tgagattacc ctggctaacg gagaaattcg gaagcgcccc ctgattgaaa ccaacggaga    3300
aactggagaa attgtgtggg acaagggacg ggacttcgcc accgtccgca aggtcctctc    3360
aatgccccaa gtcaacatcg tgaaaaagac cgaagtgcaa accggcggct tctcaaagga    3420
gtccatcctg cctaagcgca acagcgacaa gctgattgcc aggaagaagg actgggaccc    3480
gaagaagtac ggaggatttg attccctac cgtggcctac tccgtgctcg tggtggccaa    3540
agtggaaaag gggaaatcca agaagctgaa gtcggtgaag gagcttttgg gtatcaccat    3600
catggaacgc tcctcgttcg aaaagaaccc aatcgatttc ctggaagcta agggttataa    3660
ggaagtgaaa aaggacctga ttatcaagct gcccaagtac tcactgttcg agctggaaaa    3720
cggtcggaaa aggatgctgg ccagcgccgg agaactccag aagggaaacg aactggcact    3780
gccgtccaaa tacgtcaact tcctctacct tgcatcccat tacgaaaaac tcaagggatc    3840
gccggaggac aacgagcaga agcagctttt cgtggagcaa cacaagcatt acttggacga    3900
gatcatcgag cagatttccg agttctcaaa gcgcgtgatc ctggccgacg caaatctgga    3960
caaggtcctg tccgcgtaca ataagcatcg ggacaagcct atccgcgaac aggccgagaa    4020
catcatccat ctgttcactc tgacaaacct gggcgcaccc gccgcgttca gtactttga    4080
caccaccatc gataggaagc gatacaccct aactaaggaa gtgttggacg cgaccttat    4140
ccatcagtcg atcaccgggc tgtacgaaac acggatcgac ctcagccagt ggggaggcga    4200
caagcgccct gcggctacca agaaggccgg acaggccaag aagaagaaat gagcggccgc    4260
ttaattaagc tgccttctgc ggggcttgcc ttctggccat gcccttcttc tctcccttgc    4320
acctgtacct cttggtcttt gaataaagct tgagtaggaa gtctagaaaa aaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaa                                                                4506
```

```
SEQ ID NO: 53              moltype = DNA   length = 20
FEATURE                   Location/Qualifiers
source                    1..20
                          mol_type = other DNA
                          organism = synthetic construct
SEQUENCE: 53
gccccaagat gatggaagtt                                                        20

SEQ ID NO: 54              moltype = DNA   length = 20
FEATURE                   Location/Qualifiers
source                    1..20
                          mol_type = other DNA
                          organism = synthetic construct
SEQUENCE: 54
ggccccaact tccatcatct                                                        20

SEQ ID NO: 55              moltype = DNA   length = 20
FEATURE                   Location/Qualifiers
source                    1..20
                          mol_type = other DNA
                          organism = synthetic construct
SEQUENCE: 55
```

-continued

```
tgccaaggcc gcagtccagc                                                 20

SEQ ID NO: 56          moltype = DNA   length = 20
FEATURE                Location/Qualifiers
source                 1..20
                       mol_type = other DNA
                       organism = synthetic construct
SEQUENCE: 56
aggcagcagc gtcttccgca                                                 20

SEQ ID NO: 57          moltype = DNA   length = 20
FEATURE                Location/Qualifiers
source                 1..20
                       mol_type = other DNA
                       organism = synthetic construct
SEQUENCE: 57
ccgtcccctg ctacaagcca                                                 20

SEQ ID NO: 58          moltype = DNA   length = 20
FEATURE                Location/Qualifiers
source                 1..20
                       mol_type = other DNA
                       organism = synthetic construct
SEQUENCE: 58
agcctgctgg actgcggcct                                                 20

SEQ ID NO: 59          moltype = DNA   length = 20
FEATURE                Location/Qualifiers
source                 1..20
                       mol_type = other DNA
                       organism = synthetic construct
SEQUENCE: 59
gacggaagct gtgtgccgtc                                                 20

SEQ ID NO: 60          moltype = DNA   length = 20
FEATURE                Location/Qualifiers
source                 1..20
                       mol_type = other DNA
                       organism = synthetic construct
SEQUENCE: 60
taatgtgaaa accgatggag                                                 20

SEQ ID NO: 61          moltype = DNA   length = 20
FEATURE                Location/Qualifiers
source                 1..20
                       mol_type = other DNA
                       organism = synthetic construct
SEQUENCE: 61
ccgactgctg aagaacttcc                                                 20

SEQ ID NO: 62          moltype = DNA   length = 20
FEATURE                Location/Qualifiers
source                 1..20
                       mol_type = other DNA
                       organism = synthetic construct
SEQUENCE: 62
gttttcacat taaccaggct                                                 20

SEQ ID NO: 63          moltype = DNA   length = 20
FEATURE                Location/Qualifiers
source                 1..20
                       mol_type = other DNA
                       organism = synthetic construct
SEQUENCE: 63
ggttttcaca ttaaccaggc                                                 20

SEQ ID NO: 64          moltype = DNA   length = 20
FEATURE                Location/Qualifiers
source                 1..20
                       mol_type = other DNA
                       organism = synthetic construct
SEQUENCE: 64
ctggttaatg tgaaaaccga                                                 20

SEQ ID NO: 65          moltype = DNA   length = 20
FEATURE                Location/Qualifiers
source                 1..20
                       mol_type = other DNA
                       organism = synthetic construct
```

-continued

```
SEQUENCE: 65
caccgtttta aaaactcggt                                                    20

SEQ ID NO: 66            moltype = DNA   length = 20
FEATURE                  Location/Qualifiers
source                   1..20
                         mol_type = other DNA
                         organism = synthetic construct
SEQUENCE: 66
gagtttttaa aacggtgaac                                                    20

SEQ ID NO: 67            moltype = DNA   length = 20
FEATURE                  Location/Qualifiers
source                   1..20
                         mol_type = other DNA
                         organism = synthetic construct
SEQUENCE: 67
taggcatgag tcgacaccca                                                    20

SEQ ID NO: 68            moltype = DNA   length = 20
FEATURE                  Location/Qualifiers
source                   1..20
                         mol_type = other DNA
                         organism = synthetic construct
SEQUENCE: 68
aggcatgagt cgacacccac                                                    20

SEQ ID NO: 69            moltype = DNA   length = 20
FEATURE                  Location/Qualifiers
source                   1..20
                         mol_type = other DNA
                         organism = synthetic construct
SEQUENCE: 69
gtcgacaccc acgggtgtgt                                                    20

SEQ ID NO: 70            moltype = DNA   length = 20
FEATURE                  Location/Qualifiers
source                   1..20
                         mol_type = other DNA
                         organism = synthetic construct
SEQUENCE: 70
cacttactct cactggccgg                                                    20

SEQ ID NO: 71            moltype = DNA   length = 20
FEATURE                  Location/Qualifiers
source                   1..20
                         mol_type = other DNA
                         organism = synthetic construct
SEQUENCE: 71
tgacacttac tctcactggc                                                    20

SEQ ID NO: 72            moltype = DNA   length = 20
FEATURE                  Location/Qualifiers
source                   1..20
                         mol_type = other DNA
                         organism = synthetic construct
SEQUENCE: 72
tgcagtggac aatgcccgag                                                    20

SEQ ID NO: 73            moltype = DNA   length = 20
FEATURE                  Location/Qualifiers
source                   1..20
                         mol_type = other DNA
                         organism = synthetic construct
SEQUENCE: 73
cttactctca ctggccggag                                                    20

SEQ ID NO: 74            moltype = DNA   length = 20
FEATURE                  Location/Qualifiers
source                   1..20
                         mol_type = other DNA
                         organism = synthetic construct
SEQUENCE: 74
acttactctc actggccgga                                                    20

SEQ ID NO: 75            moltype = DNA   length = 20
FEATURE                  Location/Qualifiers
source                   1..20
                         mol_type = other DNA
```

```
                                   organism = synthetic construct
SEQUENCE: 75
gtggacaatg cccgaggggc                                                    20

SEQ ID NO: 76         moltype = DNA  length = 20
FEATURE               Location/Qualifiers
source                1..20
                      mol_type = other DNA
                      organism = synthetic construct
SEQUENCE: 76
atcctcctga agctcaagac                                                    20

SEQ ID NO: 77         moltype = DNA  length = 20
FEATURE               Location/Qualifiers
source                1..20
                      mol_type = other DNA
                      organism = synthetic construct
SEQUENCE: 77
gttagtgtga aaaccgatgg                                                    20

SEQ ID NO: 78         moltype = DNA  length = 20
FEATURE               Location/Qualifiers
source                1..20
                      mol_type = other DNA
                      organism = synthetic construct
SEQUENCE: 78
gtggttagtg tgaaaaccga                                                    20

SEQ ID NO: 79         moltype = DNA  length = 20
FEATURE               Location/Qualifiers
source                1..20
                      mol_type = other DNA
                      organism = synthetic construct
SEQUENCE: 79
ttttaaaaac tcgataggtg                                                    20

SEQ ID NO: 80         moltype = DNA  length = 20
FEATURE               Location/Qualifiers
source                1..20
                      mol_type = other DNA
                      organism = synthetic construct
SEQUENCE: 80
gcagttatgt aagtagccct                                                    20

SEQ ID NO: 81         moltype = DNA  length = 20
FEATURE               Location/Qualifiers
source                1..20
                      mol_type = other DNA
                      organism = synthetic construct
SEQUENCE: 81
gtcattggcc acaaagcacg                                                    20

SEQ ID NO: 82         moltype = DNA  length = 20
FEATURE               Location/Qualifiers
source                1..20
                      mol_type = other DNA
                      organism = synthetic construct
SEQUENCE: 82
ctcggctgtt tcgaatccct                                                    20

SEQ ID NO: 83         moltype = RNA  length = 20
FEATURE               Location/Qualifiers
source                1..20
                      mol_type = other RNA
                      organism = synthetic construct
SEQUENCE: 83
gccccaagat gatggaagtt                                                    20

SEQ ID NO: 84         moltype = RNA  length = 20
FEATURE               Location/Qualifiers
source                1..20
                      mol_type = other RNA
                      organism = synthetic construct
SEQUENCE: 84
ggccccaact tccatcatct                                                    20

SEQ ID NO: 85         moltype = RNA  length = 20
FEATURE               Location/Qualifiers
source                1..20
```

-continued

```
                              mol_type = other RNA
                              organism = synthetic construct
SEQUENCE: 85
tgccaaggcc gcagtccagc                                                20

SEQ ID NO: 86        moltype = RNA   length = 20
FEATURE              Location/Qualifiers
source               1..20
                     mol_type = other RNA
                     organism = synthetic construct
SEQUENCE: 86
aggcagcagc gtcttccgca                                                20

SEQ ID NO: 87        moltype = RNA   length = 20
FEATURE              Location/Qualifiers
source               1..20
                     mol_type = other RNA
                     organism = synthetic construct
SEQUENCE: 87
ccgtcccctg ctacaagcca                                                20

SEQ ID NO: 88        moltype = RNA   length = 20
FEATURE              Location/Qualifiers
source               1..20
                     mol_type = other RNA
                     organism = synthetic construct
SEQUENCE: 88
agcctgctgg actgcggcct                                                20

SEQ ID NO: 89        moltype = RNA   length = 20
FEATURE              Location/Qualifiers
source               1..20
                     mol_type = other RNA
                     organism = synthetic construct
SEQUENCE: 89
gacggaagct gtgtgccgtc                                                20

SEQ ID NO: 90        moltype = RNA   length = 20
FEATURE              Location/Qualifiers
source               1..20
                     mol_type = other RNA
                     organism = synthetic construct
SEQUENCE: 90
taatgtgaaa accgatggag                                                20

SEQ ID NO: 91        moltype = RNA   length = 20
FEATURE              Location/Qualifiers
source               1..20
                     mol_type = other RNA
                     organism = synthetic construct
SEQUENCE: 91
ccgactgctg aagaacttcc                                                20

SEQ ID NO: 92        moltype = RNA   length = 20
FEATURE              Location/Qualifiers
source               1..20
                     mol_type = other RNA
                     organism = synthetic construct
SEQUENCE: 92
gttttcacat taaccaggct                                                20

SEQ ID NO: 93        moltype = RNA   length = 20
FEATURE              Location/Qualifiers
source               1..20
                     mol_type = other RNA
                     organism = synthetic construct
SEQUENCE: 93
ggttttcaca ttaaccaggc                                                20

SEQ ID NO: 94        moltype = RNA   length = 20
FEATURE              Location/Qualifiers
source               1..20
                     mol_type = other RNA
                     organism = synthetic construct
SEQUENCE: 94
ctggttaatg tgaaaaccga                                                20

SEQ ID NO: 95        moltype = RNA   length = 20
FEATURE              Location/Qualifiers
```

-continued

| | | |
|---|---|---|
| source | 1..20 | |
| | mol_type = other RNA | |
| | organism = synthetic construct | |

SEQUENCE: 95
caccgtttta aaaactcggt                                                              20

| | | |
|---|---|---|
| SEQ ID NO: 96 | moltype = RNA   length = 20 | |
| FEATURE | Location/Qualifiers | |
| source | 1..20 | |
| | mol_type = other RNA | |
| | organism = synthetic construct | |

SEQUENCE: 96
gagtttttaa aacggtgaac                                                              20

| | | |
|---|---|---|
| SEQ ID NO: 97 | moltype = RNA   length = 20 | |
| FEATURE | Location/Qualifiers | |
| source | 1..20 | |
| | mol_type = other RNA | |
| | organism = synthetic construct | |

SEQUENCE: 97
taggcatgag tcgacaccca                                                              20

| | | |
|---|---|---|
| SEQ ID NO: 98 | moltype = RNA   length = 20 | |
| FEATURE | Location/Qualifiers | |
| source | 1..20 | |
| | mol_type = other RNA | |
| | organism = synthetic construct | |

SEQUENCE: 98
aggcatgagt cgacacccac                                                              20

| | | |
|---|---|---|
| SEQ ID NO: 99 | moltype = RNA   length = 20 | |
| FEATURE | Location/Qualifiers | |
| source | 1..20 | |
| | mol_type = other RNA | |
| | organism = synthetic construct | |

SEQUENCE: 99
gtcgacaccc acgggtgtgt                                                              20

| | | |
|---|---|---|
| SEQ ID NO: 100 | moltype = RNA   length = 20 | |
| FEATURE | Location/Qualifiers | |
| source | 1..20 | |
| | mol_type = other RNA | |
| | organism = synthetic construct | |

SEQUENCE: 100
cacttactct cactggccgg                                                              20

| | | |
|---|---|---|
| SEQ ID NO: 101 | moltype = RNA   length = 20 | |
| FEATURE | Location/Qualifiers | |
| source | 1..20 | |
| | mol_type = other RNA | |
| | organism = synthetic construct | |

SEQUENCE: 101
tgacacttac tctcactggc                                                              20

| | | |
|---|---|---|
| SEQ ID NO: 102 | moltype = RNA   length = 20 | |
| FEATURE | Location/Qualifiers | |
| source | 1..20 | |
| | mol_type = other RNA | |
| | organism = synthetic construct | |

SEQUENCE: 102
tgcagtggac aatgcccgag                                                              20

| | | |
|---|---|---|
| SEQ ID NO: 103 | moltype = RNA   length = 20 | |
| FEATURE | Location/Qualifiers | |
| source | 1..20 | |
| | mol_type = other RNA | |
| | organism = synthetic construct | |

SEQUENCE: 103
cttactctca ctggccggag                                                              20

| | | |
|---|---|---|
| SEQ ID NO: 104 | moltype = RNA   length = 20 | |
| FEATURE | Location/Qualifiers | |
| source | 1..20 | |
| | mol_type = other RNA | |
| | organism = synthetic construct | |

SEQUENCE: 104
acttactctc actggccgga                                                              20

| | | |
|---|---|---|
| SEQ ID NO: 105 | moltype = RNA   length = 20 | |

-continued

```
FEATURE                Location/Qualifiers
source                 1..20
                       mol_type = other RNA
                       organism = synthetic construct
SEQUENCE: 105
gtggacaatg cccgaggggc                                            20

SEQ ID NO: 106         moltype = RNA   length = 20
FEATURE                Location/Qualifiers
source                 1..20
                       mol_type = other RNA
                       organism = synthetic construct
SEQUENCE: 106
atcctcctga agctcaagac                                            20

SEQ ID NO: 107         moltype = RNA   length = 20
FEATURE                Location/Qualifiers
source                 1..20
                       mol_type = other RNA
                       organism = synthetic construct
SEQUENCE: 107
gttagtgtga aaaccgatgg                                            20

SEQ ID NO: 108         moltype = RNA   length = 20
FEATURE                Location/Qualifiers
source                 1..20
                       mol_type = other RNA
                       organism = synthetic construct
SEQUENCE: 108
gtggttagtg tgaaaaccga                                            20

SEQ ID NO: 109         moltype = RNA   length = 20
FEATURE                Location/Qualifiers
source                 1..20
                       mol_type = other RNA
                       organism = synthetic construct
SEQUENCE: 109
ttttaaaaac tcgataggtg                                            20

SEQ ID NO: 110         moltype = RNA   length = 20
FEATURE                Location/Qualifiers
source                 1..20
                       mol_type = other RNA
                       organism = synthetic construct
SEQUENCE: 110
gcagttatgt aagtagccct                                            20

SEQ ID NO: 111         moltype = RNA   length = 20
FEATURE                Location/Qualifiers
source                 1..20
                       mol_type = other RNA
                       organism = synthetic construct
SEQUENCE: 111
gtcattggcc acaaagcacg                                            20

SEQ ID NO: 112         moltype = RNA   length = 20
FEATURE                Location/Qualifiers
source                 1..20
                       mol_type = other RNA
                       organism = synthetic construct
SEQUENCE: 112
ctcggctgtt tcgaatccct                                            20
```

MODULATING EXPRESSION OF ALAS1 (5'-AMINOLEVULINATE SYNTHASE 1) GENE

RELATED APPLICATIONS

The present application claims priority to U.S. Provisional Application No. 63/515,045, filed Jul. 21, 2023; U.S. Provisional Application No. 63/598,408, filed Nov. 13, 2023; and U.S. Provisional Application No. 63/624,610, filed Jan. 24, 2024. The entire contents of these applications are hereby expressly incorporated by reference in their entireties.

REFERENCE TO SEQUENCE LISTING

The present application is being filed along with a Sequence Listing in electronic format. The Sequence Listing is provided as a file entitled 80EM-341775-US_Sequence-Listing, created Jun. 29, 2024, which is 399 kilobytes in size. The information in the electronic format of the Sequence Listing is incorporated herein by reference in its entirety.

BACKGROUND

Field

The present disclosure generally relates to the field of molecular biology and biotechnology, including gene editing.

Description of the Related Art

5'-Aminolevulinate Synthase 1 (ALAS1) is an enzyme that catalyzes the first and rate-limiting step of heme synthesis in the liver. ALAS1 catalyzes the synthesis of 5-aminolevulinic acid (ALA) from glycine and succinyl-CoA. ALAS1 (e.g., ALAS1 over-expression) is associated with various conditions, including porphyria.

The targeting of DNA using the RNA-guided, DNA-targeting principle of CRISPR (Clustered Regularly Interspaced Short Palindromic Repeats)-Cas (CRISPR associated) systems has been widely used. CRISPR-Cas systems can be divided in two classes, with class 1 systems utilizing a complex of multiple Cas proteins (such as type I, III, and IV CRISPR-Cas systems) and class 2 systems utilizing a single Cas protein (such as type II, V, and VI CRISPR-Cas systems). Type II CRISPR-Cas-based systems have been used for genome editing, and require a Cas polypeptide or variant thereof guided by a customizable guide RNA (gRNA) for programmable DNA targeting.

There is a need for developing safe and effective therapy for treating and preventing ALAS1-related diseases and disorders.

SUMMARY

Disclosed herein include guide RNAs (gRNAs) for targeting a 5'-Aminolevulinate Synthase 1 (ALAS1) genomic locus. In some embodiments, the gRNA comprises a spacer sequence comprising any one of the sequences of SEQ ID NOs: 25-48 and 83-112.

In some embodiments, the spacer sequence comprises a sequence selected from the group consisting of SEQ ID NOs: 25-48 and 83-112. In some embodiments, the gRNA comprises a spacer sequence comprising any one of the sequences of SEQ ID NOs: 25-37 and 101-112. In some embodiments, the gRNA comprises a spacer sequence comprising the sequence of SEQ ID NO: 45, SEQ ID NO: 83, SEQ ID NO: 86, or SEQ ID NO: 87. In some embodiments, the gRNA comprises a spacer sequence comprising the sequence of SEQ ID NO: 25, SEQ ID NO: 26, SEQ ID NO: 27, SEQ ID NO: 29, or SEQ ID NO: 30. In some embodiments, the gRNA comprises a spacer sequence comprising the sequence of SEQ ID NO: 29 or SEQ ID NO: 30. In some embodiments, the gRNA induces, or is capable of inducing, a cutting efficiency of at least 40%, at least 50%, at least 60%, at least 70%, at least 80%, at least 90%, or at least 95% for targeting the ALAS1 genomic locus. In some embodiments, the gRNA is capable of inducing a cutting efficiency of at least 50%, at least 60%, at least 70%, at least 80%, at least 90%, or at least 95% for targeting the ALAS1 genomic locus. In some embodiments, the gRNA the gRNA reduces, or is capable of inducing, a cutting efficiency of at least 60%, at least 70%, at least 80%, at least 90%, or at least 95% for targeting the ALAS1 genomic locus. In some embodiments, the gRNA is a single-guide RNA (sgRNA).

The gRNA can be a chemically-modified gRNA. In some embodiments, the chemically-modified gRNA comprises one or more phosphorothioate linkages and/or one or more 2'-O-methyl nucleotides at the 3' end, the 5' end, or both. In some embodiments, 50% or less of the nucleotides of the gRNA comprise a 2'-O-methyl modification. In some embodiments, about 48% of the nucleotides of the gRNA comprise a 2'-O-methyl modification. In some embodiments, the 5' end of the gRNA comprises three phosphorothioate linkages and the 3' end of the gRNA comprises three phosphorothioate linkages.

Disclosed herein include compositions. In some embodiments, the composition comprises (a) any of the gRNAs disclosed herein or a polynucleotide encoding the gRNA, and (b) an endonuclease or a nucleic acid encoding an endonuclease. In some embodiments, the composition comprises (a) any of the gRNAs disclosed herein or a polynucleotide encoding the gRNA, and (b) a Cas9 endonuclease or a nucleic acid encoding a Cas9 endonuclease.

In some embodiments, the composition comprises: (a) a guide RNA (gRNA) that targets an ALAS1 genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease.

In some embodiments, the spacer sequence comprises a sequence selected from the group consisting of SEQ ID NOs: 25-48 and 83-112. In some embodiments, the gRNA is a single-guide RNA (sgRNA). In some embodiments, the gRNA is a chemically-modified gRNA. In some embodiments, the chemically-modified gRNA comprises one or more phosphorothioate linkages and/or one or more 2'-O-methyl nucleotides at the 3' end, the 5' end, or both. In some embodiments, 50% or less of the nucleotides of the gRNA comprise a 2'-O-methyl modification. In some embodiments, about 48% of the nucleotides of the gRNA comprise a 2'-O-methyl modification. In some embodiments, the 5' end of the gRNA comprises three phosphorothioate linkages and the 3' end of the gRNA comprises three phosphorothioate linkages.

In some embodiments, the Cas9 endonuclease is selected from S. pyogenes Cas9, S. aureus Cas9, N. meningitides Cas9, S. thermophilus CRISPR1 Cas9, S. thermophilus CRISPR 3 Cas9, and T. denticola Cas9. In some embodiments, the composition comprises (a) the ALAS1 gRNA and (b) the Cas9 endonuclease, and the ALAS1 gRNA and Cas 9 nuclease are formulated as a ribonucleoprotein particle (RNP). In some embodiments, the composition comprises (a) a nucleic acid encoding an ALAS1 gRNA and (b) a nucleic acid encoding a Cas9 endonuclease. In some embodiments, (a) and/or (b) is present on a viral vector. In some embodiments, the viral vector is an adeno-associated viral vector. In some embodiments, the gRNA or the nucleic acid encoding a gRNA of (a), the Cas9 endonuclease or the nucleic acid encoding a Cas9 endonuclease of (b), or both are complexed with a liposome or lipid nanoparticle (LNP). In some embodiments, the lipid nanoparticle comprises one or more neutral lipids, charged lipids, ionizable lipids, steroids, and polymers conjugated lipids. In some embodiments, the lipid nanoparticle comprises cholesterol, a polyethylene glycol (PEG) lipid, or both.

Disclosed herein include methods for treating a disease or disorder caused by ALAS1 over-expression in a subject in need thereof. In some embodiments, the method comprises administering to the subject any one of the compositions disclosed herein, thereby treating the disease or disorder caused by ALAS1 over-expression in the subject.

Disclosed herein include methods for treating a subject that has or is suspected of having porphyria. In some embodiments, the method comprises administering to the subject any one of the compositions disclosed herein, thereby treating the porphyria.

Disclosed herein include methods for treating a disease or disorder caused by ALAS1 over-expression in a subject in need thereof. In some embodiments, the method comprises administering to the subject a composition comprising a plurality of nanoparticles complexed with: (a) a guide RNA (gRNA) that targets an ALAS1 genomic locus or a nucleic acid encoding the gRNA; and (b) a Cas9 endonuclease or a nucleic acid encoding a Cas9 endonuclease, thereby treating the disease or disorder caused by ALAS1 over-expression in the subject. In some embodiments, the method comprises administering to the subject a composition comprising a plurality of nanoparticles complexed with: (a) a gRNA that targets an ALAS1 genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease, thereby treating the disease or disorder caused by ALAS1 over-expression in the subject.

Disclosed herein include methods for treating a subject that has or is suspected of having porphyria. In some embodiments, the method comprises administering to the subject a composition comprising a plurality of nanoparticles complexed with: (a) a gRNA that targets an ALAS1 genomic locus or a nucleic acid encoding the gRNA; and (b) a Cas9 endonuclease or a nucleic acid encoding a Cas9 endonuclease, thereby treating the porphyria. In some embodiments, the method comprises administering to the subject a composition comprising a plurality of nanoparticles complexed with: (a) a gRNA that targets an ALAS1 genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease, thereby treating the porphyria.

The Cas9 endonuclease can be, e.g., S. pyogenes Cas9, S. aureus Cas9, N. meningitides Cas9, S. thermophilus CRISPR1 Cas9, S. thermophilus CRISPR 3 Cas9, or T. denticola Cas9. In some embodiments, the plurality of nanoparticles are lipid nanoparticles. The lipid nanoparticles can, e.g., comprise one or more neutral lipids, charged lipids, ionizable lipids, steroids, and polymers conjugated lipids. In some embodiments, the lipid nanoparticles comprise cholesterol, a polyethylene glycol (PEG) lipid, or both. The method can comprise administering to the subject the composition at a single dose of about 0.1 mg/kg, 0.3 mg/kg, 0.6 mg/kg, 1.0 mg/kg, or 2.0 mg/kg of total nucleic acids of (a) and (b). In some embodiments, the method comprises a single administration of the composition to the subject. In some embodiments, the subject is administered the composition two or more times. In some embodiments, each two of the two or more administrations are about two weeks to about four weeks apart. In some embodiments, each two of the two or more administrations are at least three months apart.

In some embodiments, the expression of ALAS1 in the subject is reduced in the subject. In some embodiments, the expression of ALAS1 is reduced in the liver of the subject. In some embodiments, the reduction is relative to (a) the ALAS1 expression of the subject prior to being administered the composition; (b) the ALAS1 expression in one or more untreated subjects; and/or (c) a reference level of ALAS1 expression of healthy subjects. In some embodiments, the expression of ALAS1 in the subject is reduced by at least 20% after the administration. In some embodiments, the expression of ALAS1 in the subject is reduced by at least 50%, at least 60%, at least 70%, at least 80%, at least 90%, or at least 95% after the administration. In some embodiments, levels of ALAS1 mRNA are reduced by at least 90% following the administration. In some embodiments, levels of ALAS1 protein are reduced by at least 75% following the administration. In some embodiments, the reduction is for at least two weeks, at least three weeks, at least four weeks, or at least a month. The method can comprise administering to the subject a therapeutically effective amount of at least one additional therapeutic agent to the subject. In some embodiments, the additional therapeutic agent is hematin, heme arginite, an ALAS1 siRNA, or a combination thereof.

In some embodiments, the subject has, or is suspected of having, cutaneous porphyria. The cutaneous porphyria can be, e.g., congenital erythropoietic porphyria (CEP), hepato-erythropoietic porphyria (HEP), porphyria cutanea tarda (PCT), or erythropoietic protoporphyria and X-linked porphyria (EP/XLP). In some embodiments, the subject has, is suspected of having, or has had acute porphyria. The acute porphyria can be, e.g., acute intermittent porphyria (AIP), hereditary coproporphyria (HCP), variegate porphyria (VP), or delta-aminolevulinic acid dehydratase deficiency porphyria (ADP). In some embodiments, the frequency of attacks of acute porphyria is reduced in the subject as compared to the subject prior to the administration.

The subject can have elevated urine porphobilinogen (PBG), elevated urine aminolevulinic acid (ALA), elevated urine porphyrins, elevated fecal porphyrins, elevated plasma porphyrins, or any combination thereof. In some embodiments, as compared to a reference value. In some embodiments, the levels of plasma and/or urine porphobilinogen (PBG), plasma and/or urine aminolevulinic acid (ALA), urine porphyrins, fecal porphyrins, plasma porphyrins, or any combination thereof are reduced in the subject following administration of the composition. In some embodiments, the levels of ALAS1 mRNA in the urine of the subject are reduced following administration of the composition; and wherein the reduction is relative to (a) the ALAS1 mRNA levels of the subject prior to being administered the composition; (b) the ALAS1 mRNA levels in one or more untreated subjects; and/or (c) a reference level of ALAS1 mRNA of healthy subjects. In some embodiments, the subject has, or is suspected of having, a mutation in at least one gene selected from the group consisting of: ALAS2, ALAD, HMBS, UROD, UROS, CPOX, PPOX, and FECH. In some embodiments, the mutation results in a reduction in the expression, stability, and/or activity of the RNA and/or protein products of the at least one gene.

BRIEF DESCRIPTION OF THE DRAWINGS

FIG. 9A displays data from human hepatocytes. FIG. 9B displays data from NHP hepatocytes. Protein level is presented as the relative expression of treated samples compared to untreated samples.

DETAILED DESCRIPTION

Figure 1:
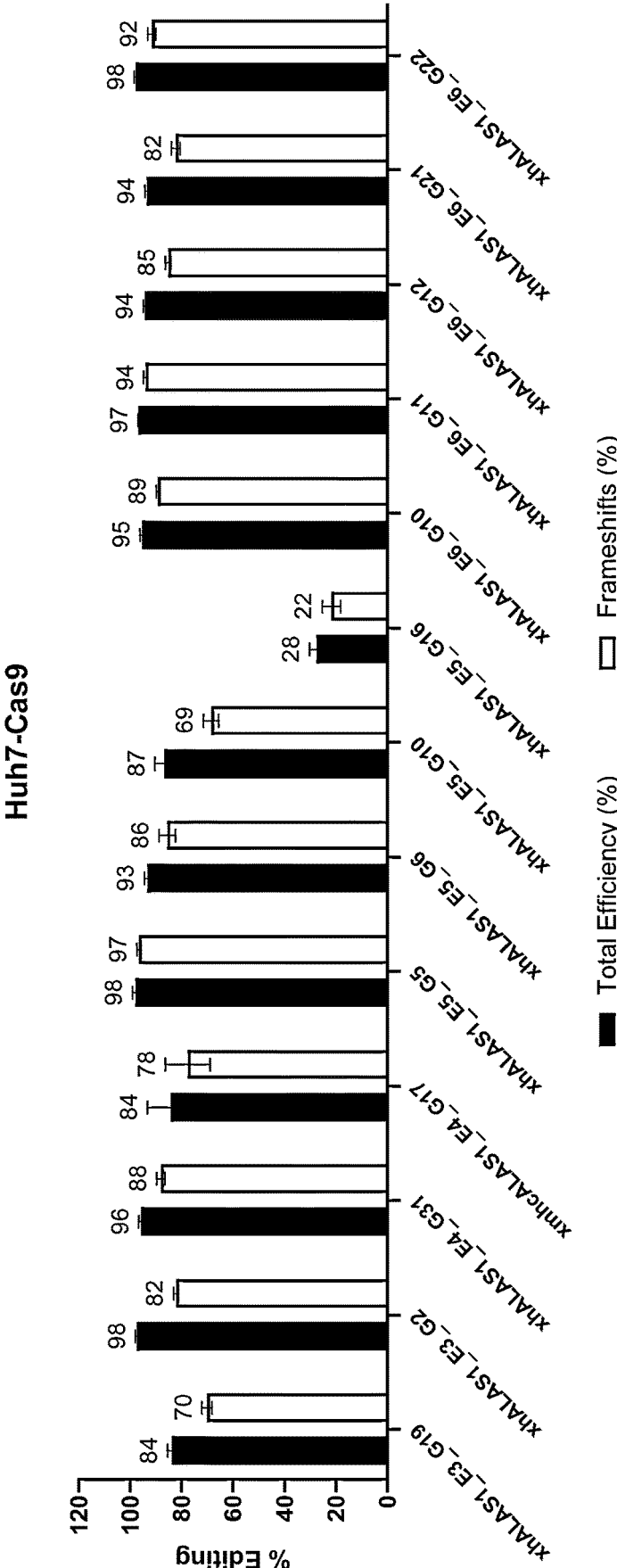
FIG. 1 displays non-limiting exemplary data depicting editing efficiencies of gRNAs comprising the indicated spacer sequences in Huh7-Cas9 human hepatoma cells.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include guide RNAs (gRNAs) for targeting a 5'-Aminolevulinate Synthase 1 (ALAS1) genomic locus. In some embodiments, the gRNA comprises a spacer sequence comprising any one of the sequences of SEQ ID NOs: 25-48 and 83-112.

Disclosed herein include compositions. In some embodiments, the composition comprises (a) any of the gRNAs disclosed herein or a polynucleotide encoding the gRNA, and (b) a Cas9 endonuclease or a nucleic acid encoding a Cas9 endonuclease.

In some embodiments, the composition comprises: (a) a gRNA that targets an ALAS1 genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease.

Disclosed herein include methods for treating a disease or disorder caused by ALAS1 over-expression in a subject in need thereof. In some embodiments, the method comprises administering to the subject any one of the compositions disclosed herein, thereby treating the disease or disorder caused by ALAS1 over-expression in the subject.

Disclosed herein include methods for treating a subject that has or is suspected of having porphyria. In some embodiments, the method comprises administering to the subject any one of the compositions disclosed herein, thereby treating the porphyria.

Disclosed herein include methods for treating a disease or disorder caused by ALAS1 over-expression in a subject in need thereof. In some embodiments, the method comprises administering to the subject a composition comprising a plurality of nanoparticles complexed with: (a) a gRNA that targets an ALAS1 genomic locus or a nucleic acid encoding the gRNA; and (b) a Cas9 endonuclease or a nucleic acid encoding a Cas9 endonuclease, thereby treating the disease or disorder caused by ALAS1 over-expression in the subject. Disclosed herein include methods for treating a disease or disorder caused by ALAS1 over-expression in a subject in need thereof. In some embodiments, the method comprises administering to the subject a composition comprising a plurality of nanoparticles complexed with: (a) a gRNA that targets an ALAS1 genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease, thereby treating the disease or disorder caused by ALAS1 over-expression in the subject.

Disclosed herein include methods for treating a subject that has or is suspected of having porphyria. In some embodiments, the method comprises administering to the subject a composition comprising a plurality of nanoparticles complexed with: (a) a gRNA that targets an ALAS1 genomic locus or a nucleic acid encoding the gRNA; and (b) a Cas9 endonuclease or a nucleic acid encoding a Cas9 endonuclease, thereby treating the porphyria. Disclosed herein include methods for treating a subject that has or is suspected of having porphyria. In some embodiments, the method comprises administering to the subject a composition comprising a plurality of nanoparticles complexed with: (a) a guide RNA (gRNA) that targets an ALAS1 genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease, thereby treating the porphyria.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "about" can mean plus or minus 5% of the provided value.

As used herein, the term "RNA-guided endonuclease" refers to a polypeptide capable of binding an RNA (e.g., a gRNA) to form a complex targeted to a specific DNA sequence (e.g., in a target DNA). A non-limiting example of RNA-guided endonuclease is a Cas polypeptide (e.g., a Cas endonuclease, such as a Cas9 endonuclease). In some embodiments, the RNA-guided endonuclease as described herein is targeted to a specific DNA sequence in a target DNA by an RNA molecule to which it is bound. The RNA molecule can include a sequence that is complementary to and capable of hybridizing with a specific sequence within the target DNA, thus allowing for targeting of the bound polypeptide to a specific location within the target DNA.

As used herein, the term "guide RNA" or "gRNA" can refer to a site-specific targeting RNA that can bind an RNA-guided endonuclease to form a complex, and direct the activities of the bound RNA-guided endonuclease (such as a Cas endonuclease) to a specific sequence within a target nucleic acid (e.g., a specific gene or region within a gene). The guide RNA can include one or more RNA molecules.

As used herein, a "secondary structure" of a nucleic acid molecule (e.g., an RNA fragment, or a gRNA) refers to the base pairing interactions within the nucleic acid molecule.

As used herein, the term "Cas endonuclease" or "Cas nuclease" refers to an RNA-guided DNA endonuclease associated with and/or derived from the CRISPR adaptive immunity system.

Unless otherwise indicated "nuclease" and "endonuclease" are used interchangeably herein to refer to an enzyme which possesses endonucleolytic catalytic activity for polynucleotide cleavage.

The terms "polynucleotide" and "nucleic acid" are used interchangeably herein and refer to a polymeric form of nucleotides of any length, either ribonucleotides or deoxyribonucleotides. A polynucleotide can be single-, double-, or multi-stranded DNA or RNA, genomic DNA, cDNA, DNA-RNA hybrids/triple helices, or a polymer including purine and pyrimidine bases or other natural, chemically or biochemically modified, non-natural, or derivatized nucleotide bases.

As used herein, the term "binding" refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it means that the molecule X binds to molecule Y in a non-covalent manner). Binding interactions can be characterized by a dissociation constant (Kd), for example a Kd of, or a Kd less than, $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-1}$ M, or a number or a range between any two of these values. Kd can be dependent on environmental conditions, e.g., pH and temperature. "Affinity" refers to the strength of binding, and increased binding affinity is correlated with a lower Kd.

As used herein, the term "hybridizing" or "hybridize" refers to the pairing of substantially complementary or complementary nucleic acid sequences within two different molecules. Pairing can be achieved by any process in which a nucleic acid sequence joins with a substantially or fully complementary sequence through base pairing to form a hybridization complex. "Hybridizing" or "hybridize" can comprise denaturing the molecules to disrupt the intramolecular structure(s) (e.g., secondary structure(s)) in the molecule. In some embodiments, denaturing the molecules comprises heating a solution comprising the molecules to a temperature sufficient to disrupt the intramolecular structures of the molecules. In some instances, denaturing the molecules comprises adjusting the pH of a solution comprising the molecules to a pH sufficient to disrupt the intramolecular structures of the molecules. For purposes of hybridization, two nucleic acid sequences or segments of sequences are "substantially complementary" if at least 80% of their individual bases are complementary to one another. In some embodiments, a splint oligonucleotide sequence is not more than about 50% identical to one of the two polynucleotides (e.g., RNA fragments) to which it is designed to be complementary. The complementary portion of each sequence can be referred to herein as a "segment", and the segments are substantially complementary if they have 80% or greater identity.

The terms "complementarity" and "complementary" mean that a nucleic acid can form hydrogen bond(s) with another nucleic acid based on traditional Watson-Crick base paring rule, that is, adenine (A) pairs with thymine (T, or uracil (U) in RNA) and guanine (G) pairs with cytosine (C). Complementarity can be perfect (e.g. complete complementarity) or imperfect (e.g. partial complementarity). Perfect or complete complementarity indicates that each and every nucleic acid base of one strand is capable of forming hydrogen bonds according to Watson-Crick canonical base pairing with a corresponding base in another, antiparallel nucleic acid sequence. Partial complementarity indicates that only a percentage of the contiguous residues of a nucleic acid sequence can form Watson-Crick base pairing with the same number of contiguous residues in another, antiparallel nucleic acid sequence. In some embodiments, the complementarity can be at least 70%, 80%, 90%, 100% or a number or a range between any two of these values. In some embodiments, the complementarity is perfect, i.e., 100%. For example, the complementary candidate sequence segment is perfectly complementary to the candidate sequence segment, whose sequence can be deduced from the candidate sequence segment using the Watson-Crick base pairing rules.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The terms "DNA editing efficiency," or "editing efficiency" may be used interchangeably herein and can refer to the number or proportion of intended target sequences that are edited. For example, if a CRISPR-Cas9 system edits 10% of the intended target sequence (e.g., within a cell or within a population of cells), then the system can be described as being 10% efficient. In some embodiments, the efficiency can be reported as % indel, e.g., the proportion of insertions and/or deletions detected in the target sequence. Indels (e.g., insertion-deletions) can result from repair of double-stranded DNA breaks caused by Cas9 cleavage by processes including, but not limited to, non-homologous end joining (NHEJ) repair.

The term "off-target editing frequency," as used herein, refers to the number or proportion of unintended DNA sequences that are edited. On-target and off-target editing frequencies may be measured by the methods and assays described herein, further in view of techniques known in the art, including high-throughput sequencing reads. As used herein, high-throughput sequencing involves the hybridization of nucleic acid primers (e.g., DNA primers) with complementarity to nucleic acid (e.g., DNA) regions just upstream or downstream of the target sequence or off-target sequence of interest. Since many of the Cas9-dependent off-target sites have high sequence identity to the target site of interest, nucleic acid primers with sufficient complementarity to regions upstream or downstream of the Cas9-dependent off-target site may be designed using techniques and kits known in the art. These kits make use of polymerase chain reaction (PCR) amplification, which produces amplicons as intermediate products. The target and off-target sequences may comprise genomic loci that further comprise protospacers and PAMs. Accordingly, the term "amplicons," as used herein, may refer to nucleic acid molecules that constitute the aggregates of genomic loci, protospacers and PAMs. High-throughput sequencing techniques used herein may further include Sanger sequencing and/or whole genome sequencing (WGS).

As used herein, the terms "transfection" or "infection" refer to the introduction of a nucleic acid into a host cell, such as by contacting the cell with liposomes or nanoparticles (e.g., lipid nanoparticles) as described herein.

As used herein, "treatment" refers to a clinical intervention made in response to a disease, disorder or physiological condition manifested by a patient or to which a patient may be susceptible. The aim of treatment includes, but is not limited to, the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented.

As used herein, the terms "effective amount" or "pharmaceutically effective amount" or "therapeutically effective amount" refer to an amount sufficient to effect beneficial or desirable biological and/or clinical results.

The term "pharmaceutically acceptable excipient" as used herein refers to any suitable substance that provides a pharmaceutically acceptable carrier, additive or diluent for administration of a compound(s) of interest to a subject. Pharmaceutically acceptable excipients can encompass substances referred to as pharmaceutically acceptable diluents, pharmaceutically acceptable additives, and pharmaceutically acceptable carriers.

As used herein, a "subject" refers to an animal for whom a diagnosis, treatment, or therapy is desired. In some embodiments, the subject is a mammal. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a primate. In some embodiments, the mammal is a human. In some embodiments, the mammal is not a human. In some embodiments, the subject has or is suspected of having an ALAS1-associated disease or disorder.

5'-Aminolevulinate Synthase 1 (ALAS1) and Heme Biosynthesis

5'-Aminolevulinate Synthase 1 or delta-aminolevulinate synthase 1 (ALAS1), is a nuclear-encoded mitochondrial protein that catalyzes the first step of heme biosynthesis. ALAS1 functions primarily in the liver, where heme is required for, e.g., synthesis of P450 enzymes. A paralog, ALAS2, is mostly active in bone marrow. ALAS enzymes (e.g., ALAS1) catalyze the condensation of glycine with succinyl-CoA to form delta-aminolevulinic acid (ALA). This first step of heme biosynthesis is the rate-limiting step in the pathway in the liver. In some embodiments, ALAS1 levels are regulated via negative feedback, wherein heme negatively regulates ALAS1 expression and/or activity.

The next steps of heme biosynthesis are summarized below. From ALA, the enzyme ALA-dehydratase (ALAD) catalyzes the condensation of two ALA molecules to form porphobilinogen (PBG). Next, porphobilinogen deaminase (PBGD) activity converts four PBG molecules to hydroxymethylbilane (HMB). Uroporphyrinogen III synthase (UROS or UROIIIS) catalyzes the formation of uroporphyrinogen III from hydroxymethylbilane. Uroporphyrinogen decarboxylase (UROD) catalyzes the removal of the four carboxylic groups of the carboxymethyl side chains in uroporphyrinogen to yield coproporphyrinogen. The enzymes Coproporphyrinogen oxidase (CPO or CPOX) and Protoporphyrinogen oxidase (PPO or PPOX) convert coproporphyrinogen to protoporphyrinogen IX and then protoporphyrin IX. In the final step, iron is inserted into the protoporphyrin IX to form heme, and this reaction is catalyzed by Ferrochelatase (FECH). Each of the products of these reactions can, in some embodiments, be referred to as "porphyrins."

As noted above, ALAS1 enzyme is the rate-limiting step of the heme biosynthesis pathway, and over-expression of ALAS1, e.g., in subjects with a mutation in other enzymes in the pathway, can result in diseases or disorders such as porphyria. Murine studies have found that ubiquitously expressed isozyme ALAS1 has an indispensable function for early embryogenesis in mice. ALAS1-null embryos are lethal by embryonic day 8.5 (E8.5). However, no apparent abnormalities in heterozygous knockout animals were observed (A1+/− mice) until 20-weeks of age. In some embodiments, the heterozygous mice showed a prediabetic phenotype under normally fed conditions and also presented glucose intolerance and insulin resistance in an age-dependent manner (as opposed to an overt diabetic phenotype), as well as abnormalities in the mitochondria of skeletal muscle. Strikingly, dietary administration of ALA was found to reverse insulin resistance and glucose intolerance in aged A1+/− mice. No significant reduction in total heme levels, but reduction in the regulatory "free heme" pool, was observed in the cytosolic or mitochondrial fractions of skeletal muscle from aged A1+/− mice compared to aged wild-type (WT) mice. In contrast to ALAS2, there are no reported human diseases directly caused by mutations in ALAS1.

There are two major types of porphyria based on whether they primarily affect the nervous system or the skin: acute (hepatic) or cutaneous. In Acute Hepatic Porphyria, four types of acute porphyrias affect the nervous system. Two of those types can also affect the skin. Symptoms (e.g., attacks) for acute porphyrias can develop over hours or days and last for days or weeks. There are at least four types of acute porphyrias, which can result from porphyrin accumulation in, e.g., the liver. Acute intermittent porphyria (AIP) affects the nervous system, Variegate porphyria (VP) affects the nervous system and skin, hereditary coproporphyria (HCP) affects the nervous system and skin, and delta-aminolevulinic acid (ALA) dehydratase deficiency porphyria (ALAD) affects the nervous system. The four types of cutaneous porphyrias affect only the skin and cause chronic, or long lasting, symptoms. People with cutaneous porphyria may develop skin symptoms-such as blistering or pain-after their skin is exposed to sunlight. In porphyria cutanea tarda (PCT) porphyrins can accumulate in the liver. In congenital erythropoietic (CEP) porphyrins can accumulate in bone marrow. In hepatoerythropoietic porphyria (HEP), porphyrins can accumulate in liver. In erythropoietic protoporphyria and X-linked porphyria (EP/XLP), porphyrins can accumulate in bone marrow. In some embodiments, the onset of symptoms occurs after childhood in humans, e.g., from 12-65 years of age.

Acute Intermittent Porphyria (AIP) is the most common acute porphyria, at a rate of 5-10 per 100,000 individuals with clinical AIP. 1 in 1,675 individuals in the United States carry genetic mutations for AIP. This disease is caused by deficiency of the enzyme porphobilinogen deaminase (also known as hydroxymethylbilane synthase, HMBS), on Chromosome 11, at q23.3. Variegate Porphyria (VP) is caused by PPOX gene mutation (on Chromosome 1, at q22-23), resulting in deficient function of the enzyme protoporphyrinogen oxidase. Hereditary Coporphyria (HCP) is caused by CPOX gene mutation (Chromosome 3, at q11.2), resulting in deficiency of the enzyme coproporphyrinogen oxidase. The above diseases and mutations are typically autosomal dominant mutations, e.g., only one copy of the gene is needed to be mutated to cause disease. ALA-Dehydratase Deficient Porphyria (ALAD), which is least common, is due to recessive mutation (e.g., both copies of the gene must be mutated). ALAD gene mutation (on Chromosome 9, at q34) causes deficiency of the enzyme aminolevulinate dehydratase.

Figure 7:
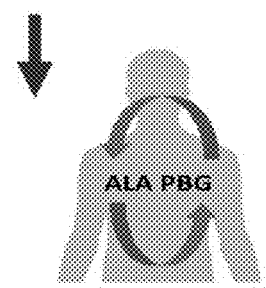
FIG. 7 displays a non-limiting diagram showing the therapeutic rationale for treatment of acute intermittent porphyria.

AIP is caused by mutation of hydroxymethylbilane synthase gene (HMBS), which encodes for the third enzyme in heme biosynthesis pathway. Loss of functional HMBS prevents the breakdown of ALA and PBG, which are toxic to the liver and other organs. Knocking out the first enzyme in the pathway, ALAS1, lowers ALA and PBG levels, which can prevent future attacks and chronic symptoms (FIG. 7). The prevalence of AIP (HMBS –/+) in the general population has been estimated as 1:1,600 with a penetrance of about 2-3% (or 10-20%, NIH 2023). Emerging data of AIP families show the penetrance is low due to vague symptoms/ misdiagnosis/missed diagnosis. Penetrance in these studies is actually 20-40% (based on symptom diagnostic in questionnaire). More patients are symptomatic when they have thought they had no clinical manifestations. Uptake of previous therapies (e.g., siRNA) have been hindered by adverse effects, like liver function test (LEFT) elevations in >155% of patients (transient, but dosing is monthly), and failure to invest in improving diagnosis.

Without being bound by any particular theory, diseases such as porphyria are caused by the accumulation of precursor molecules of the heme biosynthesis pathway (e.g., porphyrins) which can be toxic. Alcohol use, medications, stress, hormonal changes, and other factors can precipitate an episode or attack, e.g., of "acute porphyria." Acute porphyria can be characterized by multiple symptoms, including, but not limited to, neurological symptoms such as abdominal and/or chest pain, muscle weakness, autonomic neuropathy (e.g., hypertension, tachycardia, nausea, vomiting, and constipation), and changes in mental status, as well has symptoms in the skin. The non-acute (or cutaneous) porphyrias primarily affect the skin. Both acute and cutaneous porphyrias can result in, e.g., photosensitivity, blisters, and painful skin redness and swelling. Although *porphyria* attacks can be treated by providing, e.g., hemin, there is a need for long-term and/or preventative and more effective therapies and treatments for diseases caused by ALAS1 over-expression.

Gene Editing

Provided herein include methods, compositions and kits for editing an ALAS1 gene, thereby reducing the expression level of ALAS1 protein (e.g., concentrations of ALAS1 protein in the liver of a subject). Gene editing (including genomic editing) is a type of genetic engineering in which nucleotide(s)/nucleic acid(s) is/are inserted, deleted, and/or substituted in a DNA sequence, such as in the genome of a targeted cell. Targeted gene editing enables insertion, deletion, and/or substitution at pre-selected sites in the genome of a targeted cell (e.g., in a targeted gene or targeted DNA sequence). When a sequence of an endogenous gene is edited, for example by deletion, insertion or substitution of nucleotide(s)/nucleic acid(s), the endogenous gene comprising the affected sequence can be knocked-out or knocked-down due to the sequence alteration. Thus, targeted editing can be used to disrupt endogenous gene expression. "Targeted integration" refers to a process involving insertion of one or more exogenous sequences, with or without deletion of an endogenous sequence at the insertion site. Targeted integration can result from targeted gene editing when a donor template containing an exogenous sequence is present.

Targeted editing can be achieved either through a nuclease-independent approach, or through a nuclease-dependent approach. In the nuclease-independent targeted editing approach, homologous recombination is guided by homologous sequences flanking an exogenous polynucleotide to be introduced into an endogenous sequence through the enzymatic machinery of the host cell. The exogenous polynucleotide can introduce deletions, insertions or replacement of nucleotides in the endogenous sequence.

Alternatively, the nuclease-dependent approach can achieve targeted editing with higher frequency through the specific introduction of double strand breaks (DSBs) by specific rare-cutting nucleases (e.g., endonucleases). Such nuclease-dependent targeted editing also utilizes DNA repair mechanisms, for example, non-homologous end joining (NHEJ), which occurs in response to DSBs. DNA repair by NHEJ often leads to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which results in targeted integration of the exogenous genetic material.

Available endonucleases capable of introducing specific and targeted DSBs include, but are not limited to, zinc-finger nucleases (ZFN), transcription activator-like effector nucleases (TALEN), and RNA-guided CRISPR-Cas9 nuclease (CRISPR/Cas9; Clustered Regular Interspaced Short Palindromic Repeats Associated 9). Additionally, DICE (dual integrase cassette exchange) system utilizing phiC31 and Bxb1 integrases may also be used for targeted integration.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but are not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See e.g., U.S. Pat. Nos. 6,140,081; 6,453,242; and 6,534,261; WO 98/53058; WO 98/53059; WO 98/53060; WO 02/016536 and WO 03/016496, the contents of which are incorporated by reference in their entireties. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US2011/0145940. The most recognized example of a TALEN in the art is a fusion polypeptide of the FokI nuclease to a TAL effector DNA binding domain.

Additional examples of targeted nucleases suitable for use as provided herein include, but are not limited to, Bxb1, phiC31, R4, PhiBT1, and Wb/SPBc/TP901-1, whether used individually or in combination. Other non-limiting examples of targeted nucleases include naturally-occurring and recombinant nucleases, e.g., CRISPR/Cas9, restriction endonucleases, meganucleases homing endonucleases, and the like.

CRISPR-Cas Gene Editing System and RNA-Guided Nuclease

In some embodiments, the vectors, compositions, methods, and kits described herein can be used in a gene editing system, such as in a CRISPR-Cas gene editing system, to genetically edit the ALA S1 gene. For example, the CRISPR-Cas9 system is a naturally-occurring defense mechanism in prokaryotes that has been repurposed as a RNA-guided DNA-targeting platform used for gene editing. It relies on the DNA nuclease Cas9, and two noncoding RNAs: crisprRNA (crRNA) and trans-activating RNA (tracrRNA) to target the cleavage of DNA. crRNA drives sequence recognition and specificity of the CRISPR-Cas9 complex through Watson-Crick base pairing typically with a 20 nucleotide (nt) sequence in the target DNA. The CRISPR-Cas9 complex only binds DNA sequences that contain a sequence match to the first 20 nt of the crRNA, single-guide RNA (sgRNA), if the target sequence is followed by a specific short DNA motif (with, for example, the sequence NGG) referred to as a protospacer adjacent motif (PAM). TracrRNA hybridizes with the 3' end of crRNA to form an RNA-duplex structure that is bound by the Cas9 endonuclease to form the catalytically active CRISPR-Cas9 complex, which can then cleave the target DNA. Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end). After binding of CRISPR-Cas9 complex to DNA at a specific target site and formation of the site-specific DSB, the next key step is repair of the DSB. Cells use two main DNA repair pathways to repair the DSB: non-homologous end-joining (NHEJ) and homology-directed repair (HDR). In some embodiments, CRISPR-Cas9 gene editing system comprises an RNA-guided nuclease and one or more guide RNAs targeting one or more target genes.

As described herein, the RNA-guided endonuclease can be naturally-occurring or non-naturally occurring. Non-limiting examples of RNA-guided endonucleases include a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 endonuclease, and functional derivatives thereof. In some embodiments, the RNA-guided endonuclease is a Cas9 endonuclease. The Cas9 endonuclease can be from, e.g., *Streptococcus pyogenes* (SpCas9 or SpyCas9), *Staphylococcus lugdunensis* (SluCas9), or *Staphylococcus aureus* (SaCas9). In some embodiments, the RNA-guided endonuclease is a variant of Cas9, including but not limited to, a small Cas9, a dead Cas9 (dCas9), and a Cas9 nickase. In some embodiments, a Cas nuclease can comprise a RuvC or RuvC-like nuclease domain (e.g., Cpf1) and/or a HNH or HNH-like nuclease domain (e.g., Cas9). In some embodiments, the Cas9 endonuclease is *S. pyogenes* Cas9, *S. aureus* Cas9, *N. meningitides* Cas9, *S. thermophilus* Cas9, *S. thermophilus* 3 Cas9, *T. denticola* Cas9, or a variant thereof.

The RNA-guided endonuclease can be a small RNA-guided endonuclease. The small RNA-guided endonucleases can be engineered from portions of RNA-guided endonucleases derived from any of the RNA-guided endonucleases described herein and known in the art. The small RNA-guided endonucleases can be, e.g., small Cas endonucleases. In some cases, a small RNA-guided nuclease is shorter than about 1,100 amino acids in length.

The RNA-guided endonuclease can be a mutant RNA-guided endonuclease. For example, the RNA-guided endonuclease can be a mutant of a naturally occurring RNA-guided endonuclease. The mutant RNA-guided endonuclease can also be a mutant RNA-guided endonuclease with altered activity compared to a naturally occurring RNA-guided endonuclease, such as altered endonuclease activity (e.g., altered or abrogated DNA endonuclease activity without substantially diminished binding affinity to DNA). Such modification can allow for the sequence-specific DNA targeting of the mutant RNA-guided endonuclease for the purpose of transcriptional modulation (e.g., activation or repression); epigenetic modification or chromatin modification by methylation, demethylation, acetylation or deacetylation, or any other modifications of DNA binding and/or DNA-modifying proteins known in the art. In some embodiments, the mutant RNA-guided endonuclease has no DNA endonuclease activity.

The RNA-guided endonuclease can be a nickase that cleaves the complementary strand of the target DNA but has reduced ability to cleave the non-complementary strand of the target DNA, or that cleaves the non-complementary strand of the target DNA but has reduced ability to cleave the complementary strand of the target DNA. In some embodiments, the RNA-guided endonuclease has a reduced ability to cleave both the complementary and the non-complementary strands of the target DNA.

In some embodiments, a nucleic acid encoding an RNA-guided endonuclease is administered to the subject. In some embodiments, the nucleic acid can be generated by an in vitro transcription reaction. In some embodiments, generating in vitro transcribed RNA comprises incubating a linear DNA template with an RNA polymerase and a nucleotide mixture under conditions to allow (run-off) RNA in vitro transcription. The nucleotide mixture can be part of an in vitro transcription mix (IVT-mix). In some embodiments, the RNA polymerase is a T7 RNA polymerase.

The nucleotide mixture used in RNA in vitro transcription can additionally contain modified nucleotides as defined below. In some embodiments, the nucleotide mixture (e.g., the fraction of each nucleotide in the mixture) used for RNA in vitro transcription reactions can be optimized for the given RNA sequence (optimized NTP mix). Such methods are described, for example in WO2015/188933. RNA obtained by a process using an optimized NTP mix is, in some embodiments, characterized by reduced immune stimulatory properties.

In some embodiments, the nucleotide mixture is composed of (chemically) non-modified ribonucleoside triphosphates (NTPs) GTP, ATP, CTP and UTP. In some embodiments, the in vitro transcription can include the presence of at least one cap analog, e.g., a cap1 trinucleotide cap analog, m7G(5')ppp(5')(2'OMeA)pG or m7G(5')ppp(5')(2'OMeG) pG, m7G(5')ppp(5')(2'OMeA)pG or rn7(3'OMeG)(5')ppp (5')(2'OMeA)pG. In some embodiments, a 5'-cap structure is formed via enzymatic capping using capping enzymes (e.g. vaccinia virus capping enzymes and/or cap-dependent 2'-O-methyltransferases) to generate cap0 or cap1 or cap2 structures. The 5'-cap structure (cap0 or cap1) may also be added using immobilized capping enzymes and/or cap-dependent 2'-O-methyltransferases using methods and means disclosed in WO2016/193226. In some embodiments, a part or all of at least one (ribo)nucleoside triphosphate is replaced by a modified nucleoside triphosphate. In some embodiments, the modified nucleoside triphosphate comprises pseudouridine (ψ), N1-methylpseudouridine (m1 ψ), 5-methylcytosine, or 5-methoxyuridine. In some embodiments, uracil nucleotides in the nucleotide mixture are replaced (either partially or completely) by pseudouridine (ψ) and/or N1-methylpseudouridine (m1 ψ) to obtain a modified RNA. In some embodiments, the chemically modified nucleotide is pseudouridine (ψ). In some embodiments the chemically modified nucleotide is N1-methylpseudouridine (m1ψ). In some embodiments, the nucleotide mixture comprises at least one modified nucleotide and/or at least one nucleotide analogue or nucleotide derivative for incorporation into an RNA. For example, the modified nucleotide as defined herein can include nucleotide analogs/modifications, e.g., backbone modifications, sugar modifications or base modifications. A backbone modification can comprise a modification, in which phosphates of the backbone of the nucleotides are chemically modified. A sugar modification can comprise a chemical modification of the sugar of the nucleotides. Furthermore, a base modification can comprise a chemical modification of the base moiety of the nucleotides. In this context nucleotide analogs or modifications can comprise nucleotide analogs which are applicable for transcription and/or translation. In some embodiments the nucleotide mixture comprises least one modified nucleotide and/or at least one nucleotide analogues is selected from a backbone modified nucleotide, a sugar modified nucleotide and/or a base modified nucleotide, or any combination thereof.

The modified nucleosides and nucleotides, which may be included in the nucleotide mixture and incorporated into the RNA can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R═H, alkyl, cycloalkyl, aryl, aralkyl, heteroaryl or sugar); polyethyleneglycols (PEG), —O(CH$_2$CH$_{20}$)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, can be alkylamino, dialkylamino, heterocyclyl, arylamino, diarylamino, heteroarylamino, or diheteroaryl amino, ethylene diamine, polyamino) or aminoalkoxy. "Deoxy" modifications include hydrogen, amino (e.g., NH$_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O. The sugar group can also contain one or more carbons that possess the opposite stereochemical configuration than that of the corresponding carbon in ribose. Thus, a modified RNA molecule can include nucleotides containing, for instance, arabinose as the sugar.

The phosphate backbone can further be modified in the modified nucleosides and nucleotides, which can be included in the nucleotide mixture and incorporated into a modified in vitro transcribed RNA. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

A nucleotide as described herein can be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications includes an amino group, a thiol group, an alkyl group, or a halo group.

In some embodiments, the nucleotide analogues/modifications comprise 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl-inosine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, puromycin-5'-triphosphate, xanthosine-5'-triphosphate. Base-modified nucleotides can comprise 5-methylcytidine-5'-triphosphate, 7-deazaguanosine-5'-triphosphate, 5-bromocytidine-5'-triphosphate, and pseudouridine-5'-triphosphate, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyl-adenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, 5'-O-(1-thiophosphate)-adenosine, 5'-O-(1-thiophosphate)-cytidine, 5'-O-(1-thiophosphate)-guanosine, 5'-O-(1-thiophosphate)-uridine, 5'-O-(1-thiophosphate)-pseudouridine, 6-aza-cytidine, 2-thio-cytidine, alpha-thio-cytidine, Pseudo-iso-cytidine, 5-aminoallyl-uridine, 5-iodo-uridine, N1-methyl-pseudouridine, 5,6-dihydrouridine, alpha-thio-uridine, 4-thio-uridine, 6-aza-uridine, 5-hydroxy-uridine, deoxy-thymidine, 5-methyl-uridine, Pyrrolo-cytidine, inosine, alpha-thio-guanosine, 6-methyl-guanosine, 5-methyl-cytidine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, alpha-thio-adenosine, 8-azido-adenosine, or 7-deaza-adenosine.

At least one modified nucleotide and/or the at least one nucleotide analog can comprise 1-methyladenosine, 2-methyladenosine, N6-methyladenosine, 2'-O-methyladenosine, 2-methylthio-N6-methyladenosine, N6-isopentenyladenosine, 2-methylthio-N6-isopentenyladenosine, N6-threonylcarbamoyladenosine, 2-methylthio-N6-threonyl carbamoyladenosine, N6-methyl-N6-threonylcarbamoyladenosine, N6-hydroxynorvalylcarbamoyladenosine, 2-methylthio-N6-hydroxynorvalyl carbamoyladenosine, inosine, 3-methylcytidine, 2-O-methylcytidine, 2-thiocytidine, N4-acetylcytidine, lysidine, 1-methylguanosine, 7-methylguanosine, 2'-O-methylguanosine, queuosine, epoxyqueuosine, 7-cyano-7-deazaguanosine, 7-aminomethyl-7-deazaguanosine, pseudouridine, dihydrouridine, 5-methyluridine, 2'-O-methyluridine, 2-thiouridine, 4-thiouridine, 5-methyl-2-thiouridine, 3-(3-amino-3-carboxypropyl)uridine', 5-hydroxyuridine, 5-methoxyuridine, uridine 5-oxyacetic acid, uridine 5-oxyacetic acid methyl ester, 5-aminomethyl-2-thiouridine, 5-methylaminomethyluridine, 5-methylaminomethyl-2-thiouridine, 5-methylaminomethyl-2-selenouridine, 5-carboxymethylaminomethyluridine, 5-carboxymethylaminomethyl-2'-O-methyluridine, 5-carboxymethylaminomethyl-2-thiouridine, 5-(isopentenylaminomethyl)uridine, 5-(isopentenylaminomethyl)-2-thiouridine, or 5-(isopentenylaminomethyl)-2'-O-methyluridine.

In some embodiments, chemical modifications comprise pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyluridine.

In some embodiments, 100% of the uracil in the coding sequence as defined herein can have a chemical modification. In some embodiments, a chemical modification is in the 5'-position of the uracil. In some embodiments, 100% of the uracil in the coding sequence (cds) of the RNA can have a chemical modification, e.g., a chemical modification that is in the 5'-position of the uracil. In other embodiments, at least 10%, 20%, 30%, 40%, 50%, 60%, 70%, 80%, or 90% of the uracil nucleotides in the cds have a chemical modification, e.g., a chemical modification that is in the 5-position of said uracil nucleotides. Such modifications may reduce the stimulation of the innate immune system (after in vivo administration of the RNA comprising such a modified nucleotide).

The terms "cds" or "coding sequence" or "coding region" as used herein will be recognized and understood by the person of ordinary skill in the art, and are e.g., can refer to a sequence of several nucleotide triplets, which may be translated into a peptide or protein. The cds of the RNA may comprise at least one modified nucleotide, wherein said at least one modified nucleotide may be selected from pseudouridine (ψ), N1-methylpseudouridine (m1ψ), 5-methylcytosine, and 5-methoxyuridine.

As used herein, the terms "modified nucleotides" or "chemically modified nucleotides" can refer to all potential natural and non-natural chemical modifications of the building blocks of an RNA, namely the ribonucleotides A, G, C, and U.

In various embodiments the nucleotide mixture in an in vitro transcription reaction comprises a cap analog. Accordingly, in some embodiments the cap analog is a cap0, cap1, cap2, a modified cap0 or a modified cap1 analog, or a cap1 analog as described below.

The term "cap analog" or "5'-cap structure" as used herein can refer to the 5' structure of the RNA, particularly a guanine nucleotide, positioned at the 5'-end of an RNA, e.g., an mRNA. In some embodiments, the 5'-cap structure is connected via a 5'-5'-triphosphate linkage to the RNA. In some embodiments, a "5'-cap structure" or a "cap analogue" is not considered to be a "modified nucleotide" or "chemically modified nucleotides". 5'-cap structures which may be suitable include cap0 (methylation of the first nucleobase, e.g., m7GpppN), cap1 (additional methylation of the ribose of the adjacent nucleotide of m7GpppN), cap2 (additional methylation of the ribose of the 2nd nucleotide downstream of the m7GpppN), cap3 (additional methylation of the ribose of the 3rd nucleotide downstream of the m7GpppN), cap4 (additional methylation of the ribose of the 4th nucleotide downstream of the m7GpppN), ARCA (anti-reverse cap analogue), modARCA (e.g., phosphothioate modARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

A 5'-cap (cap0 or cap1) structure can be formed in chemical RNA synthesis, using capping enzymes, or in RNA in vitro transcription (co-transcriptional capping) using cap analogs. The term "cap analog" as used herein can refer to a non-polymerizable di-nucleotide or tri-nucleotide that has cap functionality in that it facilitates translation or localization, and/or prevents degradation of the RNA when incorporated at the 5'-end of the RNA. Non-polymerizable means that the cap analogue will be incorporated only at the 5'-terminus because it does not have a 5' triphosphate and therefore cannot be extended in the 3'-direction by a template-dependent polymerase, (e.g., a DNA-dependent RNA polymerase). Examples of cap analogues include m7GpppG, m7GpppA, m7GpppC; unmethylated cap analogues (e.g., GpppG); dimethylated cap analogue (e.g., m2,7GpppG), trimethylated cap analogue (e.g. m2,2,7GpppG), dimethylated symmetrical cap analogues (e.g., m7Gpppm7G), or anti reverse cap analogues (e.g., ARCA; m7,2'OmeGpppG, m7,2'dGpppG, m7,3'OmeGpppG, m7,3'dGpppG and their tetraphosphate derivatives). Further cap analogues have been described previously, e.g., WO2008/016473, WO2008/157688, WO2009/149253, WO2011/015347, and WO2013/059475. Further suitable cap analogues in that context are described in, e.g., WO2017/066793, WO2017/066781, WO2017/066791, WO2017/066789, WO2017/053297, WO2017/066782, WO2018/075827 and WO2017/066797 wherein the disclosures relating to cap analogues are incorporated herewith by reference.

In some embodiments, a cap1 structure is generated using tri-nucleotide cap analogue as disclosed in WO2017/053297, WO2017/066793, WO2017/066781, WO2017/066791, WO2017/066789, WO2017/066782, WO2018/075827 and WO2017/066797. For example, any cap analog derivable from the structure disclosed in claim 1-5 of WO2017/053297 may be suitably used to co-transcriptionally generate a cap1 structure. In some embodiments, any cap analog derivable from the structure described in WO2018/075827 can be suitably used to co-transcriptionally generate a cap1 structure. In some embodiments, the cap1 analog is a cap1 trinucleotide cap analog. In some embodiments, the cap1 structure of the in vitro transcribed RNA is formed using co-transcriptional capping using tri-nucleotide cap analog m7G(5')ppp(5')(2'OMeA)pG or m7G(5')ppp(5')(2'OMeG)pG. In some embodiments, the cap1 analog is m7G(5')ppp(5')(2'OMeA)pG.

In some embodiments, the RNA (e.g., mRNA) comprises a 5'-cap structure, e.g., a cap1 structure. In some embodiments, the 5' cap structure can improve stability and/or expression of the mRNA. A cap1 structure comprising mRNA (produced by, e.g., in vitro transcription) has several advantageous features including an increased translation efficiency and a reduced stimulation of the innate immune system. In some embodiments, the in vitro transcribed RNA comprises at least one coding sequence encoding at least one peptide or protein. In some embodiments, the protein is an RNA-guided endonuclease. In some embodiments, the RNA-guided endonuclease is Cas9 or a derivative thereof.

The present disclosure provides optimized mRNAs encoding an *S. pyogenes* Cas9 endonuclease ("SpCas9 mRNA"), and which optionally include chemically modified nucleotides, that provide effective genome editing of a target cell population when administered with one or more gRNAs. In some embodiments, the disclosure provides an mRNA comprising (i) a 5' untranslated region (UTR); (ii) an open reading frame (ORF) comprising a nucleotide sequence that encodes a site-directed endonuclease; and (iii) a 3' untranslated region (UTR). In some embodiments, the site-directed endonuclease is a Cas nuclease. In some embodiments, the Cas nuclease is a Cas9 polypeptide. In some embodiments, the Cas9 polypeptide is a *Streptococcus pyogenes*-derived Cas9 (SpCas9) polypeptide. In some embodiments, the ORF further comprises one or more nucleotide sequences encoding a nuclear localization signal, such as one described herein. In some embodiments, the ORF comprises a nucleotide sequence encoding a site-directed endonuclease, such as a SpCas9 polypeptide and at least one NLS that is a nucleoplasmin and/or SV40 NLS. In some embodiments, the ORF comprises a nucleotide sequence encoding an N-terminal and/or C-terminal NLS operably-linked to a site-directed endonuclease, such as a SpCas9 polypeptide. In some embodiments the ORF comprises a nucleotide sequence encoding an N-terminal SV40 NLS operably-linked to a site-directed endonuclease, such as a SpCas9 polypeptide, and a C-terminal nucleoplasmin NLS operably-linked to the site-directed endonuclease, such as the SpCas9 polypeptide.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, or 100%) identical to the nucleotide sequence of SEQ ID NO: 51. In some embodiments, the disclosure provides an mRNA comprising a nucleotide sequence that is 100% identical to the nucleotide sequence of SEQ ID NO: 51. In some embodiments, the mRNA comprises a codon-optimized sequence comprising a nucleotide sequence that is at least 85% or more (e.g., 86%, 87%, 88%, 89%, 90%, 91%, 92%, 93%, 94%, 95%, 96%, 97%, 98%, 99%, or 100%) identical to the nucleotide sequence of SEQ ID NO: 51.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, or 100%) identical to the nucleotide sequence of SEQ ID NO: 50. In some embodiments, the disclosure provides an mRNA comprising a nucleotide sequence that is 100% identical to the nucleotide sequence of SEQ ID NO: 50.

In some embodiments, the mRNA can comprise at least one chemically modified nucleoside and/or nucleotide. In some embodiments, the chemically modified nucleoside and/or nucleotide is selected from pseudouridine, N1-methylpseudouridine, and 5-methoxyuridine. In some embodiments, the chemically modified nucleoside is N1-methylpseudouridine (e.g., 1-methylpseudouridine). In some embodiments, at least about 80% or more (e.g., about 85%, 90%, 91%, 92%, 93%, 94%, 95%, 96%, 97%, 98%, 99%) of uridines in the mRNA are modified or replaced with N1-methylpseudouridine. In some embodiments, 100% of the uridines (e.g., uracils) in the mRNA are modified or replaced with N1-methylpseudouridine. In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 50, wherein 100% of the uridines or uracils of the mRNA are modified or replaced with N1-methylpseudouridine. In some embodiments, two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800 or more) of the uridine or uracil residues are N1-methylpseudouridine.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, or 100%) identical to the nucleotide sequence of SEQ ID NO: 52. In some embodiments, the disclosure provides an mRNA comprising a nucleotide sequence that has one, two, three, four, or five mismatches to the nucleotide sequence of SEQ ID NO: 52. In some embodiments, the disclosure provides an mRNA comprising a nucleotide sequence that is 100% identical to the nucleotide sequence of SEQ ID NO: 52.

Some embodiments provide an mRNA comprising a nucleotide sequence that is 100% identical to the nucleotide sequence of SEQ ID NO: 50, wherein 100% of the uridines (e.g., uracils) of the mRNA are modified or replaced with N1-methylpseudouridine. In some embodiments, an mRNA comprises or consists of the nucleotide sequence of SEQ ID NO: 52. In some embodiments, a mRNA can further comprise a 5' cap, such as one described herein. The 5' cap can be, e.g., a cap-0, a cap-1, or a cap-2 structure. SEQ ID NO: 51 is the sequence of a non-limiting exemplary parent Cas9 mRNA. SEQ ID NO: 52 is codon-optimized sequence derived from the parent Cas9 mRNA, and some u are N1-methylpseudouridines in SEQ ID NO: 52.

Optimized mRNAs encoding, for example Cas9, are also described in US20210355463A1, which is hereby incorporated by reference in its entirety.

Guide RNAs (gRNAs)

In some embodiments, the CRISPR/Cas-mediated gene editing system used to genetically edit an ALAS1 gene comprises a genome-targeting nucleic acid (e.g., a guide RNA) that can direct the activities of an RNA-guided endonuclease to a specific target sequence within the ALAS1 gene. A guide RNA comprises at least a spacer sequence that hybridizes to a specific nucleic acid sequence of interest, and a CRISPR repeat sequence. The gRNA can be a single-molecule guide RNA (sgRNA) or a double-molecule guide RNA. The RNA-guided endonuclease can be, for example a Cas endonuclease, including Cas9 endonuclease. The Cas9 endonuclease can be, for example, a SpCas9, a SaCas9, or a SluCas9 endonuclease. In some embodiments, the RNA-endonuclease is a Cas9 variant. In some embodiments, the RNA-guided endonuclease is a small RNA-guided endonuclease. In some embodiments, the RNA-guided endonuclease is a small Cas endonuclease.

In some embodiments, the gRNA comprises 5' to 3': a crRNA and a tracrRNA, wherein the crRNA and tracrRNA hybridize to form a duplex. In some embodiments, the crRNA comprises a spacer sequence capable of targeting a target sequence in a target nucleic acid (e.g., genomic DNA molecule) and a crRNA repeat sequence. In some embodiments, the tracrRNA comprises a tracrRNA anti-repeat sequence and a 3' tracrRNA sequence. In some embodiments, the 3' end of the crRNA repeat sequence is linked to the 5' end of the tracrRNA anti-repeat sequence, e.g., by a tetraloop, wherein the crRNA repeat sequence and the tracrRNA anti-repeat sequence hybridize to form the sgRNA. In some embodiments, the sgRNA comprises 5' to 3': a spacer sequence, a crRNA repeat sequence, a tetraloop, a tracrRNA anti-repeat sequence, and a 3' tracrRNA sequence. In some embodiments, the sgRNA comprise a 5' spacer extension sequence. In some embodiments, the sgRNA comprise a 3' tracrRNA extension sequence. The 3' tracrRNA can comprise, or consist of, one or more stem loops, for example one, two, three, or more stem loops.

In some embodiments, the sequence of the sgRNA comprises the nucleotide sequence of GUUUUAGAGCUA-GAAAUAGCAAGUUAAAAUAAGGCUAGU-CCGUUAUCAACUUGA AAAAGUGGCACCGAGUCGGUGCUUUU (SEQ ID NO: 49), or a nucleotide sequence having up to 1, 2, 3, 4, 5, 6, 7, 8, 9, or 10 nucleotide deletions, insertions, or substitutions relative to SEQ ID NO: 49. In some embodiments, the sgRNA is for use with a S. pyogenes Cas9 endonuclease (also referred to herein as SpCas9 or SpyCas9) herein.

The guide RNA disclosed herein can target any sequence of interest via the spacer sequence. A spacer sequence in a gRNA is a sequence (e.g., a 20-nucleotide sequence) that defines the target sequence (e.g., a DNA target sequences, such as a genomic target sequence) of a target gene of interest (e.g., ALAS1 gene). In some embodiments, the spacer sequence ranges from 15 to 30 nucleotides. For example, the spacer sequence can be, can be about, can be at least, or can be at most 10, 15, 16, 17, 18, 19, 29, 21, 22, 23, 24, 25, 26, 27, 28, 29, 30, 40, 50, or a number or a range between any of these values, of nucleotides in length. In some embodiments, a spacer sequence contains 20 nucleotides. In some embodiments, the gRNA is capable of hybridizing to the forward strand of the target dsDNA. In some embodiments, the gRNA is capable of hybridizing to the reverse strand of the target dsDNA. In some embodiments, the gRNA is capable of hybridizing to a DNA strand that is complementary to a target PAM-strand in a dsDNA.

The terms "target nucleic acid," "target site," and "target sequence" may be used interchangeably throughout and can refer to any nucleic acid sequence that may be targeted by a gRNA sequence described herein. In some embodiments, the "target sequence" is in a target gene that is adjacent to a PAM sequence and is the sequence to be modified by an RNA-guided nuclease (e.g., Cas9). The "target sequence" can be on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, in some embodiments, the gRNA spacer sequence is the RNA equivalent of the target sequence. The spacer of a gRNA interacts with a target nucleic acid of interest in a sequence-specific manner via hybridization (i.e., base pairing). The nucleotide sequence of the spacer thus varies depending on the target sequence of the target nucleic acid of interest. In some embodiments, the target sequence of the ALAS1 gene is within exon 3, 4, 5, or 6 of the ALAS1 gene.

In a CRISPR/Cas system used herein, the spacer sequence is designed to hybridize to a region of the target nucleic acid that is located 5' of a PAM recognizable by a Cas9 enzyme used in the system. The spacer can perfectly match the target sequence or can have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence (R is G or A) is the S. pyogenes PAM. In some embodiments, the PAM sequence used in the compositions and methods of the present disclosure as a sequence recognized by SpCas9 is NGG, wherein N can be A, T, C or G.

In some embodiments, the percent complementarity between the spacer sequence and the target nucleic acid is about, at least, at least about, at most or at most about 30%, 40%, 50%, 60%, 65%, 70%, 75%, 80%, 85%, 90%, 95%, 97%, 98%, 99%, or 100%. In some embodiments, the spacer sequence of the guide RNA and the target nucleic acid in the target gene is 100% complementary. In some embodiments, the percent complementarity between the spacer sequence and the target nucleic acid is 100% over the six contiguous 5'-most nucleotides of the target sequence of the complementary strand of the target nucleic acid. In some embodiments, the percent complementarity between the spacer sequence and the target nucleic acid is at least 60% over about 20 contiguous nucleotides. In other embodiments, the spacer sequence of the guide RNA and the target sequence in the target gene can contain up to 10 mismatches, e.g., up to 9, up to 8, up to 7, up to 6, up to 5, up to 4, up to 3, up to 2, or up to 1 mismatch.

In some embodiments, the gRNA is a chemically modified gRNA. Various types of RNA modifications can be introduced to the gRNAs to enhance stability, reduce the likelihood or degree of innate immune response, and/or enhance other attributes as described in the art. The gRNAs described herein can comprise one or more modifications including internucleoside linkages, purine or pyrimidine bases, or sugar. In some embodiments, a modification is introduced at the terminal of a gRNA with chemical synthesis or with a polymerase enzyme. Examples of modified nucleic acids and their synthesis are disclosed in WO2013/052523. Synthesis of modified polynucleotides is also described in Verma and Eckstein, Annual Review of Biochemistry, vol. 76, 99-134 (1998).

In some embodiments, the chemically-modified gRNA comprises phosphorothioated 2'-O-methyl nucleotides at the 3' end and the 5' end of the gRNA. In some embodiments, the chemically-modified gRNA comprises phosphorothioated 2'-O-methyl nucleotides at the 3' end of the gRNA. In some embodiments, the chemically-modified gRNA comprises phosphorothioated 2'-O-methyl nucleotides at the 5'end of the gRNA. In some embodiments, the chemically-modified gRNA comprises three or four phosphorothioated 2'-O-methyl nucleotides at the 3' end and/or three or four at the 5' end of the gRNA. In some embodiments, any one of a gRNA comprising any of SEQ ID NOs: 25-48 and 83-112 can be chemically modified to have four or more phosphorothioated 2'-O-methyl nucleotides at the 3' end and/or three at the 5' end of the gRNA.

The number and position of the phosphorothioate linkages can vary. In some embodiments, the linkage can be between the first and second, the second and third, the third and fourth position, fourth and fifth, fifth and sixth, sixth and seventh, seventh and eighth, eighth and ninth, ninth or tenth, or further, position from the 5' end of the gRNA. In some embodiments, the linkage can be between the first and second, the second and third, the third and fourth position, fourth and fifth, fifth and sixth, sixth and seventh, seventh and eighth, eighth and ninth, ninth or tenth, or further, position from the 3' end of the gRNA.

In some embodiments, the nucleotide analogues/modifications can comprise 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl-inosine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine- 5'-triphosphate, pseudouridine-5'-triphosphate, puromycin-5'-triphosphate, or xanthosine-5'-triphosphate. Base-modified nucleotides can comprise 5-methylcytidine-5'-triphosphate, 7-deazaguanosine-5'-triphosphate, 5-bromocytidine-5'-triphosphate, and pseudouridine-5'-triphosphate, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine, 5-aza-cytidine, pseudoisocytidine, 3-methyl-cytidine, N4-acetyl-cytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyl-adenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, 5'-O-(1-thiophosphate)-adenosine, 5'-O-(1-thiophosphate)-cytidine, 5'-O-(1-thiophosphate)-guanosine, 5'-O-(1-thiophosphate)-uridine, 5'-O-(1-thiophosphate)-pseudouridine, 6-aza-cytidine, 2-thio-cytidine, alpha-thio-cytidine, Pseudo-iso-cytidine, 5-aminoallyl-uridine, 5-iodo-uridine, N1-methyl-pseudouridine, 5,6-dihydrouridine, alpha-thio-uridine, 4-thio-uridine, 6-aza-uridine, 5-hydroxy-uridine, deoxy-thymidine, 5-methyl-uridine, Pyrrolo-cytidine, inosine, alpha-thio-guanosine, 6-methyl-guanosine, 5-methyl-cytidine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, alpha-thio-adenosine, 8-azido-adenosine, or 7-deaza-adenosine.

At least one modified nucleotide and/or the at least one nucleotide analog can comprise 1-methyladenosine, 2-methyladenosine, N6-methyladenosine, 2'-O-methyladenosine, 2-methylthio-N6-methyladenosine, N6-isopentenyladenosine, 2-methylthio-N6-isopentenyladenosine, N6-threonylcarbamoyladenosine, 2-methylthio-N6-threonyl carbamoyladenosine, N6-methyl-N6-threonylcarbamoyladenosine, N6-hydroxynorvalylcarbamoyladenosine, 2-methylthio-N6-hydroxynorvalyl carbamoyladenosine, inosine, 3-methylcytidine, 2-O-methylcytidine, 2-thiocytidine, N4-acetylcytidine, lysidine, 1-methylguanosine, 7-methylguanosine, 2'-O-methylguanosine, queuosine, epoxyqueuosine, 7-cyano-7-deazaguanosine, 7-aminomethyl-7-deazaguanosine, pseudouridine, dihydrouridine, 5-methyluridine, 2'-O-methyluridine, 2-thiouridine, 4-thiouridine, 5-methyl-2-thiouridine, 3-(3-amino-3-carboxypropyl)uridine', 5-hydroxyuridine, 5-methoxyuridine, uridine 5-oxyacetic acid, uridine 5-oxyacetic acid methyl ester, 5-aminomethyl-2-thiouridine, 5-methylaminomethyluridine, 5-methylaminomethyl-2-thiouridine, 5-methylaminomethyl-2-selenouridine, 5-carboxymethylaminomethyluridine, 5-carboxymethylaminomethyl-2'-O-methyluridine, 5-carboxymethylaminomethyl-2-thiouridine, 5-(isopentenylaminomethyl)uridine, 5-(isopentenylaminomethyl)-2-thiouridine, or 5-(isopentenylaminomethyl)-2'-O-methyluridine.

In some embodiments, chemical modifications comprise pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine or 2'-O-methyluridine. In some embodiments, the modification comprises a 2'-O-methyluridine (2'OMe-rU), a 2-O-methylcytidine (2'OMe-rC), 2'-O-methyladenosine (2'OMe-rA), or 2'-O-methylguanosine (2'OMe-rG).

The gRNA can comprise any number of modified nucleic acids. In some embodiments, the percentage of nucleic acids in a gRNA molecule that are modified can be, can be at least, can be about, or can be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% of the gRNA sequence. In some embodiments, 50% or less of the nucleotides of the gRNA comprise a 2'-O-methyl modification.

In some embodiments, more than one guide RNA can be used with a CRISPR/Cas nuclease system. Each guide RNA can contain a different targeting sequence, such that the CRISPR/Cas system cleaves more than one target nucleic acid. In some embodiments, one or more guide RNAs can have the same or differing properties such as activity or stability within the Cas9 RNP complex. Where more than one guide RNA is used, each guide RNA can be encoded on the same or on different vectors.

In some embodiments, the gRNAs described herein can be produced by in vitro transcription (IVT), synthetic and/or chemical synthesis methods, or a combination thereof. One or more of enzymatic IVT, solid-phase, liquid-phase, combined synthetic methods, small region synthesis, and ligation methods can be utilized. In some embodiments, the gRNAs are made using IVT enzymatic synthesis methods. Methods of making polynucleotides by IVT are known in the art and are described in WO2013/151666. Polynucleotides constructs and vectors can be used to in vitro transcribe a gRNA described herein.

Disclosed herein include guide RNAs (gRNAs) for targeting a 5'-Aminolevulinate Synthase 1 (ALAS1) genomic locus. In some embodiments, the gRNA comprises a spacer sequence comprising any one of the sequences of SEQ ID NOs: 25-48 and 83-112. In some embodiments, the gRNA comprises a spacer sequence comprising any one of the sequences of SEQ ID NOs: 25-48 and 83-112 or a variant thereof having no more than 3 mismatches compared to any one of SEQ ID NOs: 25-48 and 83-112. The spacer sequence can comprise a sequence selected from the group consisting of SEQ ID NOs: 25-48 and 83-112.

The gRNA can comprise a spacer sequence comprising any one of the sequences of SEQ ID NOs: 25-37 and 101-112. In some embodiments, the gRNA comprises a spacer sequence comprising any one of the sequences of SEQ ID NOs: 25-37 and 101-112 or a variant thereof having no more than 3 mismatches compared to any one of SEQ ID NOs: 25-37 and 101-112.

In some embodiments, the gRNA comprises a spacer sequence comprising the sequence of SEQ ID NO: 45, SEQ ID NO: 83, SEQ ID NO: 86, or SEQ ID NO: 87. In some embodiments, the gRNA comprises a spacer sequence comprising any one of the sequences of SEQ ID NO: 45, SEQ ID NO: 83, SEQ ID NO: 86, or SEQ ID NO: 87 or a variant thereof having no more than 3 mismatches compared to any one of SEQ ID NO: 45, SEQ ID NO: 83, SEQ ID NO: 86, or SEQ ID NO: 87. In some embodiments, the gRNA comprises a spacer that comprises or consists of the sequence of SEQ ID NO: 45. In some embodiments, the gRNA comprises a spacer that comprises or consists of the sequence of SEQ ID NO: 83. In some embodiments, the gRNA comprises a spacer that comprises or consists of the sequence of SEQ ID NO: 83. In some embodiments, the gRNA comprises a spacer that comprises or consists of the sequence of SEQ ID NO: 86. In some embodiments, the gRNA comprises a spacer that comprises or consists of the sequence of SEQ ID NO: 87.

In some embodiments, the gRNA comprises a spacer sequence comprising the sequence of SEQ ID NO: 25, SEQ ID NO: 26, SEQ ID NO: 27, SEQ ID NO: 29, or SEQ ID NO: 30. In some embodiments, the gRNA comprises a spacer sequence comprising any one of the sequences of SEQ ID NO: 25, SEQ ID NO: 26, SEQ ID NO: 27, SEQ ID NO: 29, or SEQ ID NO: 30 or a variant thereof having no more than 3 mismatches compared to any one of SEQ ID NO: 25, SEQ ID NO: 26, SEQ ID NO: 27, SEQ ID NO: 29, or SEQ ID NO: 30. In some embodiments, the gRNA comprises a spacer that comprises or consists of the sequence of SEQ ID NO: 25. In some embodiments, the gRNA comprises a spacer that comprises or consists of the sequence of SEQ ID NO: 26. In some embodiments, the gRNA comprises a spacer that comprises or consists of the sequence of SEQ ID NO: 27. In some embodiments, the gRNA comprises a spacer sequence comprising the sequence of SEQ ID NO: 29 or SEQ ID NO: 30. In some embodiments, the gRNA comprises a spacer sequence comprising the sequence of SEQ ID NO: 29 or SEQ ID NO: 30 or a variant thereof having no more than 3 mismatches compared to SEQ ID NO: 29 or SEQ ID NO: 30. In some embodiments, the gRNA comprises a spacer that comprises or consists of the sequence of SEQ ID NO: 29. In some embodiments, the gRNA comprises a spacer that comprises or consists of the sequence of SEQ ID NO: 30.

In some embodiments, the gRNA is capable of inducing a cutting efficiency of at least 40%, at least 50%, at least 60%, at least 70%, at least 80%, at least 90%, or at least 95% for targeting the ALAS1 genomic locus (e.g., 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values).

In some embodiments, the gRNA is capable of inducing a cutting efficiency of at least 50%, at least 60%, at least 70%, at least 80%, at least 90%, or at least 95% for targeting the ALAS1 genomic locus (e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values).

In some embodiments, the gRNA is capable of inducing a cutting efficiency of at least 60%, at least 70%, at least 80%, at least 90%, or at least 95% for targeting the ALAS1 genomic locus (e.g., 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values).

The gRNA can be a single-guide RNA (sgRNA). The gRNA can be a chemically-modified gRNA. The chemically-modified gRNA can comprise one or more phosphorothioate linkages. The chemically-modified gRNA can comprise one or more 2'-O-methyl nucleotides at the 3' end, the 5' end, or both. In some embodiments, 50% or less of the nucleotides of the gRNA comprise a 2'-O-methyl modification. For example, for a gRNA (e.g., an sgRNA) that is 100 nucleotides in length, 50 or less of the nucleotides can be a 2'-O-methyl nucleotide (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of the nucleotides can be or can comprise 2'-O-methyl nucleotides).

The 2'-O-methyl nucleotides can be at any position within the gRNA. In some embodiments, the 3 nucleotides at the 5' end of the gRNA comprise or are 2'-O-methyl nucleotides. In some embodiments approximately the last 35 or less of the nucleotides at the 3' end of the gRNA comprise or are 2'-O-methyl nucleotides (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 of the last nucleotides at the 3' end of the sgRNA). In some embodiments, e.g., for an sgRNA that is 100 bp in length, the nucleotides at positions 25-41 of the sgRNA can be or can comprise 2'-O-methyl nucleotides. About 48% of the nucleotides of the gRNA can comprise a 2'-O-methyl modification.

The 5' end of the gRNA can comprise three phosphorothioate linkages and the 3' end of the gRNA can comprise three phosphorothioate linkages. In some embodiments, the linkage can be between the first and second, the second and third, and/or the third and fourth position from the 5' end of the gRNA. In some embodiments, the linkage can be between the first and second, the second and third, and/or the third and fourth position from the 3' end of the gRNA.

Base Editing

In some embodiments, a gene can be edited using base editing. Base editing is a genome editing method that directly generates point mutations within a specific region of the genomic DNA without causing double-stranded breaks (DSB). DNA base editors (BEs) comprise fusions between a catalytically impaired Cas nuclease and a base-modification enzyme. Nucleobase editors typically include a polynucleotide programmable nucleotide binding domain and a nucleobase editing domain (e.g., adenosine deaminase, cytidine deaminase). A polynucleotide programmable nucleotide binding domain, when in conjunction with a bound guide polynucleotide (e.g., gRNA), can specifically bind to a target polynucleotide sequence and thereby localize the base editor to the target nucleic acid sequence desired to be edited. In some embodiments, base editing can be used to introduce a loss-of-function mutation (e.g., premature stop codons, destabilizing mutations, altering splicing, etc.). In other embodiments, base editing can be used to correct, a mutation (e.g., a disease-causing mutation).

In some embodiments, base editors comprising a polynucleotide programmable nucleotide binding domain comprise all or a portion (e.g., a functional portion) of a CRISPR protein. In some embodiments, the polynucleotide programmable nucleotide binding domain comprises a nickase domain. Herein the term "nickase" shall be given its ordinary meaning, and shall also refer to a polynucleotide programmable nucleotide binding domain comprising a nuclease domain that is capable of cleaving only one strand of the two strands in a double-stranded nucleic acid molecule (e.g., DNA). For example, where a polynucleotide programmable nucleotide binding domain comprises a nickase domain derived from Cas9, the Cas9-derived nickase domain can include a D10A mutation and a histidine at position 840. In another example, a Cas9-derived nickase domain comprises an H840A mutation, while the amino acid residue at position 10 remains a D. In some embodiments, a Cas9 nuclease has an inactive (e.g., an inactivated) DNA cleavage domain (e.g., the Cas9 is a nickase, referred to as an "nCas9" protein). Suitable Cas9 nickases will be apparent to those of skill in the art based on this disclosure and knowledge in the field and are within the scope of this disclosure. In some embodiments, base editors comprise a polynucleotide programmable nucleotide binding domain which is catalytically dead (e.g., incapable of cleaving a target polynucleotide sequence). For example, in the case of a base editor comprising a Cas9 domain, the Cas9 can comprise both a D10A mutation and an H840A mutation. In further embodiments, a catalytically dead polynucleotide programmable nucleotide binding domain comprises a point mutation (e.g., D10A or H840A) as well as a deletion of all or a portion (e.g., a functional portion) of a nuclease domain.

In some embodiments, a base editor comprises an adenosine deaminase domain. Such an adenosine deaminase domain of a base editor can facilitate the editing of an adenine (A) nucleobase to a guanine (G) nucleobase by deaminating the A to form inosine (I), which exhibits base pairing properties of G. In some embodiments, an A-to-G base editor further comprises an inhibitor of inosine base excision repair, for example, a uracil glycosylase inhibitor (UGI) domain or a catalytically inactive inosine specific nuclease. Without wishing to be bound by any particular theory, the UGI domain or catalytically inactive inosine specific nuclease can inhibit or prevent base excision repair of a deaminated adenosine residue (e.g., inosine), which can improve the activity or efficiency of the base editor. The adenosine deaminase can be derived from any suitable organism (e.g., E. coli, e.g., ecTadA deaminase). In some embodiments, the adenine deaminase is a naturally-occurring adenosine deaminase that includes one or more mutations. Details of A to G nucleobase editing proteins are described WO2018/027078 and Gaudelli, N. M., et al., "Programmable base editing of A»T to G»C in genomic DNA without DNA cleavage" Nature, 551, 464-471 (2017), the entire contents of which are hereby incorporated by reference.

In some embodiments, a base editor comprises a fusion protein or complex comprising cytidine deaminase capable of deaminating a target cytidine (C) base of a polynucleotide to produce uridine (U), which has the base pairing properties of thymine. In some embodiments, for example where the polynucleotide is double-stranded (e.g., DNA), the uridine base can then be substituted with a thymidine base (e.g., by cellular repair machinery) to give rise to a C:G to a T:A transition. In other embodiments, deamination of a C to U in a nucleic acid by a base editor cannot be accompanied by substitution of the U to a T. The deamination of a target C in a polynucleotide to give rise to a U is a non-limiting example of a type of base editing that can be executed by a base editor described herein. In another example, a base editor comprising a cytidine deaminase domain can mediate conversion of a cytosine (C) base to a guanine (G) base. For example, a U of a polynucleotide produced by deamination of a cytidine by a cytidine deaminase domain of a base editor can be excised from the polynucleotide by a base excision repair mechanism (e.g., by a uracil DNA glycosylase (UDG) domain), producing an abasic site. The nucleobase opposite the abasic site can then be substituted (e.g., by base repair machinery) with another base, such as a C, by for example a translesion polymerase. Although it is typical for a nucleobase opposite an abasic site to be replaced with a C, other substitutions (e.g., A, G or T) can also occur.

Accordingly, in some embodiments a base editor described herein comprises a deamination domain (e.g., cytidine deaminase domain) capable of deaminating a target C to a U in a polynucleotide. Further, as described below, the base editor can comprise additional domains which facilitate conversion of the U resulting from deamination to, in some embodiments, a T or a G. For example, a base editor comprising a cytidine deaminase domain can further comprise a uracil glycosylase inhibitor (UGI) domain to mediate substitution of a U by a T, completing a C-to-T base editing event. In another example, the base editor can comprise a uracil stabilizing protein as described herein. In another example, a base editor can incorporate a translesion polymerase to improve the efficiency of C-to-G base editing, since a translesion polymerase can facilitate incorporation of a C opposite an abasic site (i.e., resulting in incorporation of a G at the abasic site, completing the C-to-G base editing event). A base editor comprising a cytidine deaminase as a domain can deaminate a target C in any polynucleotide, including DNA, RNA and DNA-RNA hybrids.

In some embodiments, a cytidine deaminase of a base editor comprises all or a portion (e.g., a functional portion) of an apolipoprotein B mRNA editing complex (APOBEC) family deaminase. APOBEC is a family of evolutionarily conserved cytidine deaminases. Members of this family are C-to-U editing enzymes. The N-terminal domain of APOBEC like proteins is the catalytic domain, while the C-terminal domain is a pseudocatalytic domain. More specifically, the catalytic domain is a zinc dependent cytidine deaminase domain and is important for cytidine deamination. APOBEC family members include APOBEC 1, APOBEC2, APOBEC3A, APOBEC3B, APOBEC3C, APOBEC3D ("APOBEC3E" now refers to this), APOBEC3F, APOBEC3G, APOBEC3H, APOBEC4, and Activation-induced (cytidine) deaminase. In some embodiments, the deaminases are activation-induced deaminases (AID). In some embodiments, an APOBEC deaminase incorporated into a base editor can comprise one or more mutations selected from the group consisting of H121R, H122R, R126A, R126E, R118A, W90A, W90Y, and R132E of rAPOBEC1; D316R, D317R, R320A, R320E, R313A, W285A, W285Y, and R326E of hAPOBEC3G; and any alternative mutation at the corresponding position, or one or more corresponding mutations in another APOBEC deaminase. A number of modified cytidine deaminases are commercially available, including, but not limited to, SaBE3, SaKKH-BE3, VQR-BE3, EQR-BE3, VRER-BE3, YE1-BE3, EE-BE3, YE2-BE3, and YEE-BE3, which are available from Addgene (plasmids 85169, 85170, 85171, 85172, 85173, 85174, 85175, 85176, 85177). In some embodiments, a deaminase incorporated into a base editor comprises all or a portion (e.g., a functional portion) of an APOBEC 1 deaminase.

Details of C to T nucleobase editing proteins are described in WO2017/070632 and Komor, A. C., et al., "Programmable editing of a target base in genomic DNA without double-stranded DNA cleavage" Nature 533, 420-424 (2016), the entire contents of which are hereby incorporated by reference.

A polynucleotide programmable nucleotide binding domain, when in conjunction with a bound guide polynucleotide (e.g., gRNA), can specifically bind to a target polynucleotide sequence (i.e., via complementary base pairing between bases of the bound guide nucleic acid and bases of the target polynucleotide sequence) and thereby localize the base editor to the target nucleic acid sequence desired to be edited (e.g., a double-stranded DNA target). In one embodiment, the guide polynucleotide is a gRNA. In some embodiments, the guide polynucleotide is at least one single guide RNA ("sgRNA" or "gRNA"). In some embodiments, the methods described herein can utilize an engineered Cas protein. A guide RNA (gRNA) is a short synthetic RNA composed of a scaffold sequence necessary for Cas-binding and a user-defined ~20 nucleotide spacer that defines the genomic target to be modified. Thus, the specificity of the Cas protein for the genomic target of the Cas protein is partially determined by how specific the gRNA targeting sequence is for the genomic target compared to the rest of the genome. In some embodiments, the spacer is about 10, 11, 12, 13, 14, 15, 16, 17, 18, 19, 20, 22, 23, 24, 25, or more nucleotides in length. The spacer of a gRNA can be or can be about 19, 20, or 21 nucleotides in length.

Additional Exemplary Editing

In some embodiments, a gene can be edited using additional exemplary editing. In some embodiments, additional editing can be used to introduce a loss-of-function mutation (e.g., premature stop codons, destabilizing mutations, altering splicing, etc.). In other embodiments, the editing can be used to correct a mutation (e.g., a disease-causing mutation). The editing systems generally include an editor comprising a polynucleotide programmable nucleotide binding domain (e.g., a nickase Cas9) and a DNA-polymerase domain (e.g., a reverse transcriptase (RT), such as a Moloney murine leukemia virus reverse transcriptase (M-MLV RT)). The guide nucleic acid can contain an editing template. The gRNA can also include a primer-binding site (PBS). The PBS may be designed to hybridize with the displaced strand on the 5' side of the introduced cut generated by the nickase. The PBS may be complementary to a portion of the protospacer sequence. The editing template sequence includes the edit to be installed and is typically located between the tracr region (e.g., scaffold or core region) and the PBS. The length of the edit to be installed may vary, e.g., from deletions of 10 or fewer nucleotides to insertions of more than 80 nucleotides. In some embodiments, the edit comprises a substitution of 1 or more nucleotides.

In some embodiments, the target sequence is bound by the nickase Cas9 (e.g., Cas9-H840A domain) via the spacer region of the guide RNA (gRNA). The hybridization of the spacer sequence to the complementary target sequences can result in displacement of the other strand (e.g., the PAM-strand or the edit strand). The Cas9-H840A domain can cut the displaced strand, and the displaced strand then may pair with the PBS. The RT may recognize the RNA-DNA duplex formed by the displaced strand and PBS and extend the DNA of the displaced strand in the 3' direction, using the editing template (e.g., RT template) of the gRNA as a template. This can create a "flap" of single-stranded DNA on the displaced strand including the desired edit. The editor may then dissociate from the DNA, leaving two redundant "flaps" on the displaced strand, wherein one flap is the original sequence, and one flap is the edited sequence. Through a process called "flap equilibration", one of the sequences will bind the target sequence, and the other will remain attached to the displaced strand as a single-stranded flap. If the flap with the edited sequence is bound by the target sequence, the complex may be called a "DNA heteroduplex", in view of the mismatch caused by the edit. Cellular DNA repair machinery may then act on the DNA heteroduplex, incorporating the edit.

In some embodiments, where an editor comprises a nickase domain derived from Cas9, the Cas9-derived nickase domain can include a D10A mutation and a histidine at position 840. In another example, a Cas9-derived nickase domain comprises an H840A mutation, while the amino acid residue at position 10 remains a D. In some embodiments, a Cas9 nuclease has an inactive (e.g., an inactivated) DNA cleavage domain, that is, the Cas9 is a nickase, referred to as an "nCas9" protein. The Cas9 nickase may be a Cas9 protein that is capable of cleaving only one strand of a duplexed nucleic acid molecule (e.g., a duplexed DNA molecule). Additional suitable Cas9 nickases will be apparent to those of skill in the art based on this disclosure and knowledge in the field and are within the scope of this disclosure. In some embodiments, an editor comprises an RNA-dependent DNA polymerase domain, such as a reverse transcriptase (RT). In some embodiments, an editor comprises a virus RT, such as a retrovirus RT (e.g., Moloney murine leukemia virus (M-MLV or MLVRT)). In some embodiments, an editor may comprise a fusion of an *S. pyogenes* Cas9 polypeptide and a Moloney murine leukemia virus (M-MLV) reverse transcriptase polypeptide.

The gRNA can refer to a guide polynucleotide that comprises one or more intended nucleotide edits for incorporation into the target DNA. In some embodiments, the gRNA associates with and directs an editor to incorporate the one or more intended nucleotide edits into the target gene via editing. "Nucleotide edit" or "intended nucleotide edit" shall be given their ordinary meaning, and shall also refer to a specified deletion of one or more nucleotides at one specific position, insertion of one or more nucleotides at one specific position, substitution of a single nucleotide, or other alterations at one specific position to be incorporated into the sequence of the target gene. Intended nucleotide edit may refer to the edit on the editing template as compared to the sequence on the target strand of the target gene or may refer to the edit encoded by the editing template on the newly synthesized single stranded DNA. In some embodiments, a gRNA comprises a spacer sequence that is complementary or substantially complementary to a sequence on a target strand of the target gene. In some embodiments, the gRNA comprises a gRNA core that associates with a DNA binding domain, e.g., a CRISPR-Cas protein domain, of an editor. In some embodiments, the gRNA further comprises an extended nucleotide sequence comprising one or more intended nucleotide edits compared to the endogenous sequence of the target gene, wherein the extended nucleotide sequence may be referred to as an extension arm.

The extension arm can comprise a primer binding site sequence (PBS) that can initiate target-primed DNA synthesis. In some embodiments, the PBS is complementary or substantially complementary to a free 3' end on the edit strand of the target gene at a nick site generated by the editor. In some embodiments, the extension arm further comprises an editing template that comprises one or more intended nucleotide edits to be incorporated in the target gene by editing. In some embodiments, the editing template is a template for an RNA-dependent DNA polymerase domain or polypeptide of the editor, for example, a reverse transcriptase domain. In some embodiments, the editing template comprises partial complementarity to an editing target sequence in the target gene. In some embodiments, the editing template comprises substantial or partial complementarity to the editing target sequence except at the position(s) of the intended nucleotide edit(s) to be incorporated into the target gene.

Some editors include a Cas9 variant comprising an H840A mutation (i.e., a Cas9 nickase) and an M-MLV RT wild type, as well as an N-terminal NLS sequence (19 amino acids) and an amino acid linker (32 amino acids) that joins the C-terminus of the Cas9 nickase domain to the N-terminus of the RT domain. The fusion protein can have the following structure: [NLS]-[Cas9(H840A)]-[linker]-[MMLV_RT(wt)]. The editor proteins can, in some instances, include a Cas9 variant comprising an H840A mutation (i.e., a Cas9 nickase) and an M-MLV RT comprising mutations D200N, T330P, L603W, T306K, and W313F, as well as an N-terminal NLS sequence (19 amino acids) and an amino acid linker (33 amino acids) that joins the C-terminus of the Cas9 nickase domain to the N-terminus of the RT domain. The fusion protein can have the following structure: [NLS]-[Cas9(H840A)]-[linker]-[MMLV_RT (D200N)(T330P)(L603W)(T306K)(W313F)].

In some embodiments, the editing system or composition further comprises a nick guide polynucleotide, such as a nick guide RNA (ngRNA). Without wishing to be bound by any particular theory, the non-edit strand of a double stranded target DNA in the target gene may be nicked by a CRISPR-Cas nickase directed by an ngRNA. In some embodiments, the nick on the non-edit strand directs endogenous DNA repair machinery to use the edit strand as a template for repair of the non-edit strand, which may increase efficiency of editing. Some editor systems have an editor plus a second-strand nicking guide RNA that complexes with the editor and introduces a nick in the non-edited DNA strand in order to induce preferential replacement of the edited strand. In some editors, the second-strand nicking guide RNA is designed for temporal control such that the second strand nick is not introduced until after the installation of the desired edit. This is achieved by designing a gRNA with a spacer sequence that matches only the edited strand, but not the original allele. Using this strategy, mismatches between the protospacer and the unedited allele should disfavor nicking by the sgRNA until after the editing event on the PAM strand takes place. Some additional editors comprise a fusion protein comprising Cas9(R221K N39K H840A) and a variant MMLV RT pentamutant (D200N T306K W313F T330P L603W) having the following structure: [bipartite NLS]-[Cas9(R221K)(N394K)(H840A)]-[linker]-[MMLV_RT(D200N)(T330P)(L603W)]-[bipartite NLS]-[NLS]+a desired gRNA.

Some of the methods and compositions related to the editing disclosed herein are also described in WO2023015309, WO2022150790, WO2022067130, WO2020191233, WO2020191234, WO2020191239, WO2020191241, WO2020191242, WO2020191243, WO2020191245, WO2020191246, WO2020191248, WO2020191249, WO2020191153, and WO2020191171, the contents of which are incorporated herein by reference in their entireties.

Methods of Editing ALAS1 Gene

Provided herein includes a method of using genome editing to edit ALAS1 thereby functionally reducing the expression of the ALAS1 gene. The method can be used to treat a subject, e.g., a patient with an ALAS1-associated diseases or condition.

Provided herein includes a method for treating an ALAS1-related disease or disorder in a subject (e.g., a mammalian subject) in need thereof. In some embodiments, the method comprises administering to the subject a plurality of nanoparticles complexed with (a) a guide RNA (gRNA) or a nucleic acid encoding a gRNA that targets ALAS1 gene, and (b) a nucleic acid encoding an RNA-guided endonuclease, thereby relieving the ALAS1-related disease or disorder in the subject. The subject can be administered with the plurality of nanoparticles one time. The subject can be administered with the plurality of nanoparticles two or more times, for example twice, for the treatment. Two administrations of the nanoparticles to the subject can be separated by a suitable time period. In some embodiments, the suitable time period is, or is about, one week, two weeks, three weeks, four weeks, five weeks, six weeks, seven weeks, eight weeks, three months, four months, five months, six months, a year, two years, three years, or more. In some embodiments, two of the two or more administrations are about two weeks to about two months apart, for example about three weeks. In some embodiments, each two of the two or more administrations are about two weeks to about two months apart, for example about three weeks. The suitable time period between two administrations can be the same as or different from the suitable time period between another two administrations. In some embodiments, the plurality of nanoparticles is administered to the subject at a dose of about 0.01-5 mg/kg, for example 0.05-2 mg/kg, 0.5-3 mg/kg or 0.1-1 mg/kg, per administration. In some embodiments, the ALAS1 gRNA or the nucleic acid encoding the ALAS1 gRNA is administered to the subject at a dose of, or a dose of about, 0.01-5 mg/kg, for example 0.1-1 mg/kg gRNA per administration. In some embodiments, the nucleic acid encoding the RNA-guided endonuclease is administered to the subject at a dose of, or a dose of about, 0.1-5 mg/kg, for example 0.5-3 mg/kg or 0.3-2 mg/kg per administration. The dose can be the same or different for each of the administration to the subject.

In some embodiments, the gRNA targets within or near a coding sequence in the ALAS1 gene. In some embodiments, the gRNA targets a sequence within one of the 12 exons of the ALAS1 gene. In some embodiments, the gRNA targets a sequence within exon 3, 4, 5, or 6 of the ALAS1 gene. In some embodiments, the gRNA targets a sequence within exon 3, 4, 5, or 6 of the ALAS1 gene. The gRNA can comprise a spacer sequence complementary to a target sequence within exon 3, 4, 5, or 6 of the ALAS1 gene. In some embodiments, the spacer(s) are complementary to a sequence within or near (for example, within any of 1, 2, 3, 4, 5, 6, 7, 8, 9, 10, 15, 20, 25, 30, 35, 40, 45, 50, 55, 60, 65, 70, 75, 80, 85, 90, 95, 100 or more bases from) exon 3, 4, 5, or 6 of the ALAS1 gene. The complementarity between the spacer of the gRNA and the target sequence in the ALAS1 gene can be perfect or imperfect. In some embodiments, the complementarity can be at least 70%, 80%, 90%, 100% or a number or a range between any two of these values. In some embodiments, the complementarity is perfect, i.e., 100%.

In some embodiments, the gRNA comprises a spacer sequence comprising any one of the sequences of SEQ ID NOs: 25-48 and 83-112. In some embodiments, the gRNA comprises a spacer sequence selected from SEQ ID NOs: 25-48 and 83-112 or variants thereof having about, at least, at least about 80%, 85%, 90%, 95%, 97%, 98%, 99%, or 100% homology to any spacer of SEQ ID NOs: 25-48 and 83-112. In some embodiments, the gRNA comprises a spacer sequence selected from SEQ ID NOs: 25-48 and 83-112 or a variant thereof having no more than 3 mismatches compared to any one of SEQ ID NOs: 25-48 and 83-112. In some embodiments, the gRNA comprises a spacer sequence selected from SEQ ID NOs: 25-48 and 83-112. In some embodiments, the gRNA comprises or consists of a spacer sequence of SEQ ID NO: 25, SEQ ID NO: 26, or SEQ ID NO: 27. In some embodiments, the gRNA comprises or consists of a spacer sequence comprising or consisting of the sequence of SEQ ID NO: 29 or SEQ ID NO: 30. In some embodiments, the gRNA comprises a spacer sequence comprising or consisting of the sequence of SEQ ID NO: 45, SEQ ID NO: 83, SEQ ID NO: 86, or SEQ ID NO: 87. In some embodiments, the gRNA comprises a spacer sequence comprising or consisting of the sequence of SEQ ID NO: 25, SEQ ID NO: 26, SEQ ID NO: 29, or SEQ ID NO: 30.

In some embodiments, the gRNAs used in the methods herein can comprise two or more gRNAs, each comprising a spacer complementary to a sequence at the ALAS1 gene locus (e.g., any one of SEQ ID NOs: 25-48 and 83-112 or variants thereof having at least 85% homology to any one of SEQ ID Nos: 25-48 and 83-112 or variants having no more than 3 mismatches compared to any one of SEQ ID NOs: 25-48 and 83-112).

In some embodiments, the gRNAs used in the methods herein can comprise two or more gRNAs, each comprising a spacer complementary to a sequence at the ALAS1 gene locus (e.g., any one of SEQ ID NOs: 25-48 and 83-112 or variants thereof having at least 85% homology to any one of SEQ ID NOs: 25-48 and 83-112 or variants having no more than 3 mismatches compared to any one of SEQ ID NOs: 25-48 and 83-112).

In some embodiments, the guide sequence comprises a spacer sequence of SEQ ID NO: 25, SEQ ID NO: 26, SEQ ID NO: 27, SEQ ID NO: 29, SEQ ID NO: 30 or variants thereof having about, at least, or at least about 80%, 85%, 90%, 95%, 97%, 98%, 99%, or 100% homology to the spacer of SEQ ID NO: 25, SEQ ID NO: 26, SEQ ID NO: 27, SEQ ID NO: 29, or SEQ ID NO: 30. In some embodiments, the guide sequence comprises a spacer sequence of SEQ ID NO: 45, SEQ ID NO: 83, SEQ ID NO: 86, SEQ ID NO: 87 or variants thereof having about, at least, or at least about 80%, 85%, 90%, 95%, 97%, 98%, 99%, or 100% homology to the spacer of SEQ ID NO: 45, SEQ ID NO: 83, SEQ ID NO: 86, or SEQ ID NO: 87. In some embodiments, the guide sequence comprises or consists of a spacer sequence of SEQ ID NO: 25, SEQ ID NO: 26, or SEQ ID NO: 27. In some embodiments, the gRNA comprises a spacer sequence comprising the sequence of SEQ ID NO: 29 or SEQ ID NO: 30, or variants thereof having about, at least, or at least about 80%, 85%, 90%, 95%, 97%, 98%, 99%, or 100% homology to the spacer of SEQ ID NO: 29 or SEQ ID NO: 30. In some embodiments, the guide sequence comprises or consists of a spacer sequence of SEQ ID NO: 29 or SEQ ID NO: 30.

The gRNAs used herein can enhance on-target activity while significantly reducing potential off-target effects (i.e., cleaving genomic DNA at undesired locations other than ALAS1 gene). In some embodiments, the off-target binding is reduced by about, at least or at least about 80%, 85%, 90%, 95%, 98%, 99% or 100%.

In some embodiments, the gRNA induces a cutting efficiency of at least 40%, at least 50%, at least 60%, at least 70%, at least 80%, at least 90%, or at least 95% (e.g., at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values).

In some embodiments, the gRNA induces a cutting efficiency of at least 60%, at least 70%, at least 80%, at least 90%, or at least 95% (e.g., at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values).

In some embodiments, the DNA endonuclease is a Cas endonuclease described herein or known in the art. The Cas endonuclease can be naturally-occurring or non-naturally-occurring (e.g., recombinant or with mutations). In some embodiments, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional derivative thereof. In some embodiments, the DNA endonuclease is a Cas9 endonuclease or a variant thereof. In some embodiments, the Cas9 endonuclease is from *Streptococcus pyogenes* (SpyCas9 or SpCas9). In some embodiments, the Cas9 endonuclease is from *Staphylococcus lugdunensis* (SluCas9).

Compositions and Therapeutic Applications

Provided herein also includes a pharmaceutical composition for carrying out the methods disclosed herein. A composition can include one or more gRNA(s), a RNA-guided endonuclease or a nucleotide sequence encoding the RNA-guided endonuclease described herein. In some embodiments, the composition can further comprise a polynucleotide to be inserted (e.g., a donor template) in the ALAS1 gene to affect the desired genetic modification of the methods disclosed herein.

Disclosed herein include compositions. In some embodiments, the composition comprises (a) any of the gRNAs disclosed herein or a polynucleotide encoding the gRNA and (b) a Cas9 endonuclease or a nucleic acid encoding a Cas9 endonuclease.

In some embodiments, the composition comprises: (a) a guide RNA (gRNA) that targets a 5'-Aminolevulinate Synthase 1 (ALAS1) genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease.

The compositions can comprise any of the spacers and/or gRNAs disclosed herein. In some embodiments, the spacer sequence comprises a sequence selected from the group consisting of SEQ ID NOs: 25-48 and 83-112. The gRNA can be a single-guide RNA (sgRNA). The gRNA can be a chemically-modified gRNA. The chemically-modified gRNA can comprise one or more phosphorothioate linkages. The chemically-modified gRNA can comprise one or more 2'-O-methyl nucleotides at the 3' end, the 5' end, or both. In some embodiments, 50% or less of the nucleotides of the gRNA comprise a 2'-O-methyl modification (e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or a number or a range between any two of these values). In some embodiments, about 48% of the nucleotides of the gRNA comprise a 2'-O-methyl modification (e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or a number or a range between any two of these values). In some embodiments, the 5' end of the gRNA comprises three phosphorothioate linkages and the 3' end of the gRNA comprises three phosphorothioate linkages. In some embodiments, the Cas9 endonuclease is selected from the group consisting of *S. pyogenes* Cas9, *S. aureus* Cas9, *N. meningitides* Cas9, *S. thermophilus* CRISPR1 Cas9, *S. thermophilus* CRISPR 3 Cas9, and *T. denticola* Cas9.

The composition can comprise (a) the ALAS1 gRNA and (b) the Cas9 endonuclease, and the ALAS1 gRNA and Cas 9 nuclease can be formulated as a ribonucleoprotein particle (RNP). The composition can comprise (a) a nucleic acid encoding an ALAS1 gRNA and (b) a nucleic acid encoding a Cas9 endonuclease. In some embodiments, (a) and/or (b) is present on a viral vector. The viral vector can be an adeno-associated viral vector.

The gRNA or the nucleic acid encoding a gRNA of (a), the Cas9 endonuclease or the nucleic acid encoding a Cas9 endonuclease of (b), or both can be complexed with a liposome or lipid nanoparticle (LNP). The lipid nanoparticle can comprise one or more neutral lipids, charged lipids, ionizable lipids, steroids, and polymers conjugated lipids. The lipid nanoparticle can comprise cholesterol, a polyethylene glycol (PEG) lipid, or both.

In some embodiments, the one or more gRNA(s) each comprises a spacer complementary to a genomic sequence within or near (for example, within any of 1, 2, 3, 4, 5, 6, 7, 8, 9, 10, 15, 20, 25, 30, 35, 40, 45, 50, 55, 60, 65, 70, 75, 80, 85, 90, 95, 100 or more bases from) any exon of the ALAS1 gene. In some embodiments, the gRNA targets a sequence within any one of exons 3-6 of the ALAS1 gene. The gRNA can comprise a spacer sequence complementary or identical to a target sequence within any one of exons 3-6 of the ALAS1 gene. In some embodiments, a gRNA comprises a spacer sequence of any one of SEQ ID NOs: 25-48 and 83-112 or a variant thereof having at least 85% homology to the spacer sequence of any one of SEQ ID NOs: 25-48 and 83-112. In some embodiments, a gRNA comprises a spacer of any one of SEQ ID NOs: 25-48 and 83-112 or a variant thereof having at least 85% homology to the spacer having a sequence of SEQ ID NOs: 25-48 and 83-112. In some embodiments, a gRNA comprises a spacer of SEQ ID NO: 45, SEQ ID NO: 83, SEQ ID NO: 86, SEQ ID NO: 87, or a variant thereof having at least 85% homology to the spacer having a sequence SEQ ID NO: 45, SEQ ID NO: 83, SEQ ID NO: 86, or SEQ ID NO: 87. In some embodiments, a gRNA comprises a spacer of SEQ ID NO: 25, SEQ ID NO: 26, SEQ ID NO: 27, or a variant thereof having at least 85% homology to the spacer having a sequence SEQ ID NO: 25, SEQ ID NO: 26, or SEQ ID NO: 27. In some embodiments, the gRNA comprises a spacer comprising or consisting of the sequence of SEQ ID NO: 45, SEQ ID NO: 83, SEQ ID NO: 86, or SEQ ID NO: 87. In some embodiments, the gRNA comprises a spacer comprising or consisting of the sequence of SEQ ID NO: 25, SEQ ID NO: 26, or SEQ ID NO: 27. In some embodiments, a gRNA comprises a spacer of SEQ ID NO: 29 or SEQ ID NO: 30, or a variant thereof having at least 85% homology to the spacer having a sequence SEQ ID NO: 29 or SEQ ID NO: 30. In some embodiments, the gRNA comprises a spacer comprising or consisting of the sequence of SEQ ID NO: 29 or SEQ ID NO: 30.

In some embodiments, the RNA-guided endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 endonuclease, or a functional derivative thereof. In some embodiments, the DNA endonuclease is Cas9. In some embodiments, the Cas9 endonuclease is from *Streptococcus pyogenes* (SpyCas9). In some embodiments, the Cas9 endonuclease is from *Staphylococcus lugdunensis* (SluCas9). In some embodiments, a DNA sequence that is transcribed to the nucleic acid encoding the DNA endonuclease is codon optimized. In some embodiments, the nucleic acid encoding the DNA endonuclease (e.g., an mRNA) comprises a 5' CAP structure and 3' polyA tail. In some embodiments, the nucleic acid encoding the DNA endonuclease is linked to the gRNA via a covalent bond.

In some embodiments, one or more of the nucleic acid sequences and/or polypeptides can be delivered to cells, either in vitro or in vivo, via viral based or non-viral based delivery systems, including adenovirus vectors, adeno-associated virus (AAV) vectors, retrovirus vectors, lentiviral vectors, herpes virus vectors, liposomes, lipid nanoparticles, poxviruses, naked DNA administration, plasmids, cosmids, phages, encapsulated cell technology, and the like.

In some embodiments, the compounds of the compositions disclosed herein (e.g., the ALAS1 gRNA or the nucleic acid encoding the ALAS1 gRNA, and the nucleic acid encoding a RNA-guided endonuclease) can be formulated in a liposome or lipid nanoparticle. In some embodiments, the compounds of the composition are formulated in a lipid nanoparticle (LNP). LNP is a non-viral delivery system that can safely and effectively deliver nucleic acids to target organs (e.g., liver). The term "lipid nanoparticle" refers to a nanoscopic particle composed of lipids having a size measured in nanometers (e.g., 1-5,000 nm). In some embodiments, the lipids comprised in the lipid nanoparticles comprise cationic lipids and/or ionizable lipids. Any suitable cationic lipids and/or ionizable lipids known in the art can be used to formulate LNPs for delivery of gRNA and Cas endonuclease to the cells. Exemplary cationic lipids include one or more amine group(s) bearing positive charge. In some embodiments, the cationic lipids are ionizable such that they can exist in a positively charged or neutral from depending on pH. In some embodiments, the cationic lipid of the lipid nanoparticle comprises a protonatable tertiary amine head group that shows positive charge at low pH. The lipid nanoparticles can further comprise one or more neutral lipids (e.g., Distearoylphosphatidylcholine (DSPC), 1,2-Dioleoyl-sn-glycero-3-phosphocholine (DOPC), 1,2-Dimyristoyl-sn-glycero-3-phosphoethanolamine (DMPE), 1,2-Dipalmitoyl-sn-glycero-3-phosphorylethanolamine (DPPE) etc. as a helper lipid), charged lipids, steroids, and polymers conjugated lipids. In some embodiments, the LNP can comprise cholesterol. In some embodiments, the LNP can comprise a polyethylene glycol (PEG) lipid.

The lipid nanoparticles can comprise varying concentration of constituent lipids. In some embodiments, the molar percent of an ionizable lipid in the total lipid of a lipid nanoparticle is about, at least, at least about, at most or at most about 30%, 35%, 40%, 45%, 50%, 55%, 60%, 65%, 70%, or a number or range between any two of these values. In some embodiments, the molar percent of an ionizable lipid in a lipid nanoparticle is in a range between about 40-70% (e.g., about 60%). In some embodiments, the lipid nanoparticle can further comprise a helper lipid (e.g., DSPC), a sterol lipid (e.g., cholesterol), and PEG lipid or a phospholipid PEG conjugate. In some embodiments, the molar percent of a helper lipid in a lipid nanoparticle is about 5%-20% (e.g., about 10.5%), the molar percent of a sterol lipid is about 10%-40% (e.g., about 21%), and the molar percent of a PEG lipid is about 0.5%-10% (e.g., about 8.5%).

The LNP uptake into hepatocytes can be mediated by the Apolipoprotein E-low density lipoprotein receptor (ApoE-LDLR) or the N-Acetyl-D-galactosamine/asialoglycoprotein receptor pathway (GalNAc-ASGPR) (Sato et al., 2020, Journal of Controlled Release, 322, 217-226). In some embodiments, the LNP herein described for delivery of gRNA and Cas endonuclease to the cells can be formulated to follow the ApoE-LDLR uptake pathway. In some embodiments, the LNP herein described for delivery of gRNA and Cas endonuclease to the cells can be formulated to follow the GalNAc-ASGPR uptake pathway. In some embodiments, the LNP formulations herein described can be used to treat a subject with a disease or disorder that presents as heterozygous (HeFH) or homozygous (HoFH) for the loss of low-density lipoprotein receptor (LDLR).

In some embodiments, the lipid nanoparticles comprise N-Acetylgalactosamine (GalNAc), an amino sugar derivative of galactose. In some embodiments, GalNAc is present in the LNP in a molar percentage of about, at least, at least about, at most, or at most about 1.0%, 1.5%, 2.0%, 2.5%, 3.0%, 3.5%, 4.0%, 4.5%, 5.0%, 5.5%, or 6.0%. In some embodiments, GalNAc is present in the LNP in a molar percentage of about 2.5%. The lipid nanoparticles disclosed herein, in some embodiments, do not comprise GalNAc. In some embodiments, the lipid nanoparticles comprise GalNAc in a molar percentage of no more than about 1%, 0.9%, 0.8%, 0.7%, 0.6%, 0.5%, 0.4%, 0.3%, 0.2%, 0.1%, 0.05%, 0.01%, 0.005%, 0.001%, or less.

In some embodiments, the concentration of the nanoparticles in the compositions disclosed herein is about 58.2 mg/mL (e.g., of total lipids), and the nanoparticles are complexed with a total of about 2 mg/mL of nucleic acid of (a) the ALAS1 gRNA and (b) the Cas9 mRNA. In some embodiments, the concentration of the plurality of nanoparticles is about 58.2 mg/mL, and the nanoparticles are complexed with (a) the ALAS1 gRNA at about 1.5 mg/mL, and (b) the Cas9 mRNA at about 0.5 mg/mL.

The relative amount of the total RNA ((a) the ALAS1 gRNA or a nucleic acid encoding a gRNA that targets ALAS1 gene, and (b) a nucleic acid encoding a RNA-guided endonuclease) and the total lipid in the nanoparticles can vary in different embodiments. For example, the nanoparticles can have the total lipid and the total RNA at a weight ratio of about 15:1, 16:1, 17:1, 18:1, 19:1, 20:1, 21:1, 22:1, 23:1, 24:1, 25:1, 26:1, 27:1, 28:1, 29:1, or 30:1. In some embodiments, the nanoparticles can have the total lipid and the total RNA at a weight ratio of about 30:1. In some embodiments, the nanoparticles can have the total lipid and the total RNA at a molar ratio of about 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1 or 50:1. In some embodiments, the nanoparticles can have the total lipid and the total RNA at a molar ratio of about 40:1.

In some embodiments, the concentration of the nanoparticles in the compositions disclosed herein (e.g., of total lipids) is about, at least, at least about, at most or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/mL, or a number or a range between any two of these values. In some embodiments, the RNA in the nanoparticles is formulated at a concentration of about, at least, at least about, at most, or at most about 50, 75, 100, 200, 400, 600, 800, 1000, 1100, 1200, 1300, 1400, 1500, 1600, 1700, 1800, 1900, 2000 µg/ml or a number or a range between any two of these values.

The amount (e.g., relative amount of (a) the ALAS1 gRNA or a nucleic acid encoding a gRNA that targets ALAS1 gene, and (b) a nucleic acid encoding a RNA-guided endonuclease (e.g., a mRNA encoding a Cas protein (e.g., a Cas9 mRNA)) in the nanoparticles can vary. For example, the nanoparticles can have the nucleic acid encoding the RNA-guided endonuclease (e.g., a SpCas9 mRNA) and the ALAS1 gRNA in a 1:5, 1:4, 1:3, 1:2, 1:1, 2:1, 3:1, 4:1, or 5:1 ratio (by weight). In some embodiments, the nanoparticles can have the nucleic acid encoding the RNA-guided endonuclease and the ALAS1 gRNA in a 3:1 ratio (by weight).

In some embodiments, the plurality of nanoparticles is administered to the subject at a dose of about 0.01-5 mg/kg (determined by the total nucleic acids (e.g., the total of ALAS1 gRNA and Cas9 mRNA)) per administration. For example, a single dose or each dose of the plurality of nanoparticles administrated to the subject can be nanoparticles complexed with 0.01 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.5 mg/kg, 4 mg/kg, 4.5 mg/kg, or 5 mg/kg, or a number or a range between any two of these values total RNA (e.g., the total of ALAS1 gRNA and Cas9 mRNA). In some embodiments, the plurality of nanoparticles is administered to the subject at a dose of, or a dose about, 0.1 mg/kg, 0.3 mg/kg, 0.5 mg/kg, 0.6 mg/kg, 1 mg/kg, 1.5 mg/kg, 2.0 mg/kg, 2.5 mg/kg or 3 mg/kg (determined by the total of ALAS1 gRNA and Cas9 mRNA).

In some embodiments, the lipid nanoparticles can have a mean diameter of about, at least, at least about, at most or at most about 30 nm, 40 nm, 50 nm, 60 nm, 70 nm, 80 nm, 90 nm, 100 nm, 110 nm, 120 nm, 130 nm, 140 nm, 150 nm, or a number or a range between any of these values. In some embodiments, the lipid nanoparticle particle size is about 50 to about 100 nm in diameter, or about 70 to about 90 nm in diameter, or about 55 to about 95 nm in diameter.

In some embodiments, the compounds of the composition described herein are encapsulated in the lipid portion of the lipid nanoparticle or an aqueous space enveloped by some or all of the lipid portion of the lipid nanoparticle. The encapsulation can be full encapsulation, partial encapsulation, or both. In some embodiments, the nucleic acid and/or polypeptides are fully or substantially encapsulated (e.g., greater than 90% of the RNA) in the lipid nanoparticle.

In some embodiments, one or more compounds herein described are associated with a liposome or lipid nanoparticle via a covalent bond or non-covalent bond. In some embodiments, any of the compounds in the composition can be separately or together contained in a liposome or lipid nanoparticle.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes described herein. Production of pseudotyped rAAV is disclosed in, for example, international patent application publication number WO 2001/83692.

AAV particles packaging polynucleotides encoding compositions of the disclosure, e.g., endonucleases, donor sequences, or RNA guide molecules, of the present disclosure may comprise or be derived from any natural or recombinant AAV serotype. According to the present disclosure, the AAV particles may utilize or be based on a serotype selected from any of the following serotypes, and variants thereof including but not limited to AAV1, AAV10, AAV106.1/hu.37, AAV11, AAV114.3/hu.40, AAV12, AAV127.2/hu.41, AAV127.5/hu.42, AAV128.1/hu.43, AAV128.3/hu.44, AAV130.4/hu.48, AAV145.1/hu.53, AAV145.5/hu.54, AAV145.6/hu.55, AAV16.12/hu.11, AAV16.3, AAV16.8/hu.10, AAV161.10/hu.60, AAV161.6/hu.61, AAV1-7/rh.48, AAV1-8/rh.49, AAV2, AAV2.5T, AAV2-15/rh.62, AAV223.1, AAV223.2, AAV223.4, AAV223.5, AAV223.6, AAV223.7, AAV2-3/rh.61, AAV24.1, AAV2-4/rh.50, AAV2-5/rh.51, AAV27.3, AAV29.3/bb.1, AAV29.5/bb.2, AAV2G9, AAV-2-pre-miRNA-101, AAV3, AAV3.1/hu.6, AAV3.1/hu.9, AAV3-11/rh.53, AAV3-3, AAV33.12/hu.17, AAV33.4/hu.15, AAV33.8/hu.16, AAV3-9/rh.52, AAV3a, AAV3b, AAV4, AAV4-19/rh.55, AAV42.12, AAV42-10, AAV42-11, AAV42-12, AAV42-13, AAV42-15, AAV42-1b, AAV42-2, AAV42-3a, AAV42-3b, AAV42-4, AAV42-5a, AAV42-5b, AAV42-6b, AAV42-8, AAV42-aa, AAV43-1, AAV43-12, AAV43-20, AAV43-21, AAV43-23, AAV43-25, AAV43-5, AAV4-4, AAV44.1, AAV44.2, AAV44.5, AAV46.2/hu.28, AAV46.6/hu.29, AAV4-8/r11.64, AAV4-8/rh.64, AAV4-9/rh.54, AAV5, AAV52.1/hu.20, AAV52/hu.19, AAV5-22/rh.58, AAV5-3/rh.57, AAV54.1/hu.21, AAV54.2/hu.22, AAV54.4R/hu.27, AAV54.5/hu.23, AAV54.7/hu.24, AAV58.2/hu.25, AAV6, AAV6.1, AAV6.1.2, AAV6.2, AAV7, AAV7.2, AAV7.3/hu.7, AAV8, AAV-8b, AAV-8h, AAV9, AAV9.11, AAV9.13, AAV9.16, AAV9.24, AAV9.45, AAV9.47, AAV9.61, AAV9.68, AAV9.84, AAV9.9, AAVA3.3, AAVA3.4, AAVA3.5, AAVA3.7, AAV-b, AAVC1, AAVC2, AAVC5, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAV-DJ, AAV-DJ8, AAVF3, AAVF5, AAV-h, AAVH-1/hu.1, AAVH2, AAVH-5/hu.3, AAVH6, AAVhE1.1, AAVhER1.14, AAVhEr1.16, AAVhEr1.18, AAVhEr1.23, AAVhEr1.35, AAVhEr1.36, AAVhEr1.5, AAVhEr1.7, AAVhEr1.8, AAVhEr2.16, AAVhEr2.29, AAVhEr2.30, AAVhEr2.31, AAVhEr2.36, AAVhEr2.4, AAVhEr3.1, AAVhu.1, AAVhu.10, AAVhu.11, AAVhu.12, AAVhu.13, AAVhu.14/9, AAVhu.15, AAVhu.16, AAVhu.17, AAVhu.18, AAVhu.19, AAVhu.2, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.3, AAVhu.31, AAVhu.32, AAVhu.34, AAVhu.35, AAVhu.37, AAVhu.39, AAVhu.4, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.5, AAVhu.51, AAVhu.52, AAVhu.53, AAVhu.54, AAVhu.55, AAVhu.56, AAVhu.57, AAVhu.58, AAVhu.6, AAVhu.60, AAVhu.61, AAVhu.63, AAVhu.64, AAVhu.66, AAVhu.67, AAVhu.7, AAVhu.8, AAVhu.9, AAVhu.t 19, AAVLG-10/rh.40, AAVLG-4/rh.38, AAVLG-9/hu.39, AAVLG-9/hu.39, AAV-LK01, AAV-LK02, AAVLK03, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK17, AAV-LK18, AAV-LK19, AAVN721-8/rh.43, AAV-PAEC, AAV-PAEC11, AAV-PAEC12, AAV-PAEC2, AAV-PAEC4, AAV-PAEC6, AAV-PAEC7, AAV-PAEC8, AAVpi.1, AAVpi.2, AAVpi.3, AAVrh.10, AAVrh.12, AAVrh.13, AAVrh.13R, AAVrh.14, AAVrh.17, AAVrh.18, AAVrh.19, AAVrh.2, AAVrh.20, AAVrh.21, AAVrh.22, AAVrh.23, AAVrh.24, AAVrh.25, AAVrh.2R, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.43, AAVrh.44, AAVrh.45, AAVrh.46, AAVrh.47, AAVrh.48, AAVrh.48, AAVrh.48.1, AAVrh.48.1.2, AAVrh.48.2, AAVrh.49, AAVrh.50, AAVrh.51, AAVrh.52, AAVrh.53, AAVrh.54, AAVrh.55, AAVrh.56, AAVrh.57, AAVrh.58, AAVrh.59, AAVrh.60, AAVrh.61, AAVrh.62, AAVrh.64, AAVrh.64R1, AAVrh.64R2, AAVrh.65, AAVrh.67, AAVrh.68, AAVrh.69, AAVrh.70, AAVrh.72, AAVrh.73, AAVrh.74, AAVrh.8, AAVrh.8R, AAVrh8R, AAVrh8R A586R mutant, AAVrh8R R533A mutant, BAAV, BNP61 AAV, BNP62 AAV, BNP63 AAV, bovine AAV, caprine AAV, Japanese AAV10, true type AAV (ttAAV), UPENN AAV10, AAV-LK16, AAAV, AAV Shuffle 100-1, AAV Shuffle 100-2, AAV Shuffle 100-3, AAV Shuffle 100-7, AAV Shuffle 10-2, AAV Shuffle 10-6, AAV Shuffle 10-8, AAV SM 100-10, AAV SM 100-3, AAV SM 10-1, AAV SM 10-2, and/or AAV SM 10-8.

In some embodiments, the AAV serotype is, or has, a mutation in the AAV9 sequence as described by N Pulicherla et al. (Molecular Therapy 19(6): 1070-1078 (2011)), such as but not limited to, AAV9.9, AAV9.11, AAV9.13, AAV9.16, AAV9.24, AAV9.45, AAV9.47, AAV9.61, AAV9.68, AAV9.84.

In some embodiments, the AAV serotype is, or has, a sequence as described in U.S. Pat. No. 6,156,303, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S.

Pat. No. 6,156,303), AAV3A (SEQ ID NO: 4 and 9 of U.S. Pat. No. 6,156,303), or derivatives thereof.

In some embodiments, the serotype may be AAVDJ or a variant thereof, such as AAVDJ8 (or AAV-DJ8), as described by Grimm et al. (Journal of Virology 82(12): 5887-5911 (2008). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772 may comprise two mutations: (1) R587Q where arginine (R; Arg) at amino acid 587 is changed to glutamine (Q; Gin) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gin) and (3) R590T where arginine (R; Arg) at amino acid 590 is changed to threonine (T; Thr).

In some embodiments, the AAV serotype is, or has, a sequence as described in International Publication No. WO2015121501, such as, but not limited to, true type AAV (ttAAV) (SEQ ID NO: 2 of WO2015121501), "UPenn AAV10" (SEQ ID NO: 8 of WO2015/121501), "Japanese AAV10" (SEQ ID NO: 9 of WO2015/121501), or variants thereof.

According to the present disclosure, AAV capsid serotype selection or use may be from a variety of species. In some embodiments, the AAV is an avian AAV (AAAV). The AAAV serotype can be, or have, a sequence as described in U.S. Pat. No. 9,238,800, such as, but not limited to, AAAV (SEQ ID NO: 1, 2, 4, 6, 8, 10, 12, and 14 of U.S. Pat. No. 9,238,800), or variants thereof.

In some embodiments, the AAV is a bovine AAV (BAAV). The BAAV serotype can be, or have, a sequence as described in U.S. Pat. No. 9,193,769, such as, but not limited to, BAAV (SEQ ID NO: 1 and 6 of U.S. Pat. No. 9,193,769), or variants thereof. The BAAV serotype can be or have a sequence as described in U.S. Pat. No. 7,427,396, such as, but not limited to, BAAV (SEQ ID NO: 5 and 6 of U.S. Pat. No. 7,427,396), or variants thereof.

In some embodiments, the AAV is a caprine AAV. The caprine AAV serotype can be, or have, a sequence as described in U.S. Pat. No. 7,427,396, such as, but not limited to, caprine AAV (SEQ ID NO: 3 of U.S. Pat. No. 7,427,396), or variants thereof.

In some embodiments, the AAV is engineered as a hybrid AAV from two or more parental serotypes. In some embodiments, the AAV is AAV2G9 which comprises sequences from AAV2 and AAV9. The AAV2G9 AAV serotype can be, or have, a sequence as described in US2016/0017005.

In some embodiments, the AAV is a serotype generated by the AAV9 capsid library with mutations in amino acids 390-627 (VP1 numbering) as described by Pulicherla et al. (Molecular Therapy 19(6): 1070-1078 (2011). The serotype and corresponding nucleotide and amino acid substitutions can be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In some embodiments, the AAV is a serotype comprising at least one AAV capsid CD8+ T-cell epitope. As a non-limiting example, the serotype can be AAV1, AAV2 or AAV8. In some embodiments the AAV may be a variant, such as PHP.A or PHP.B as described in Deverman et al. 2016, Nature Biotechnology. 34(2): 204-209.

General principles of rAAV production are reviewed in, for example, Carter, 1992, Current Opinions in Biotechnology, 1533-539; and Muzyczka, 1992, Curr. Topics in Microbial, and Immunol., 158:97-129). Various approaches are described in Ratschin et al, Mol. Cell. Biol. 4:2072 (1984); Hermonat et al, Proc. Natl. Acad. Sci. USA, 81:6466 (1984); Tratschin et al, Mol. Cell. Biol. 5:3251 (1985); McLaughlin et al, J. Virol., 62: 1963 (1988); and Lebkowski et al, 1988 Mol. Cell. Biol., 7:349 (1988). Samulski et al (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO97/09441 (PCT/US96/14423); WO 97/08298 (PCT/US96/13872); WO 97/21825 (PCT/US96/20777); WO 97/06243 (PCT/FR96/01064); WO 99/11764; Perrin et al (1995) Vaccine 13: 1244-1250; Paul et al (1993) Human Gene Therapy 4:609-615; Clark et al (1996) Gene Therapy 3: 1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others.

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirus, poxvirus, vaccinia virus, and herpes simplex virus.

In some embodiments, Cas9 mRNA, sgRNA targeting one or two loci in ALAS1 gene, and donor DNA can each be separately formulated into lipid nanoparticles or are all co-formulated into one lipid nanoparticle.

In some embodiments, Cas9 mRNA can be formulated in a lipid nanoparticle, while sgRNA and donor DNA can be delivered in an AAV vector.

Options are available to deliver the Cas9 nuclease as a DNA plasmid, as mRNA or as a protein. The guide RNA can be expressed from the same DNA, or can also be delivered as an RNA. The RNA can be chemically modified to alter or improve its half-life, or decrease the likelihood or degree of immune response. The endonuclease protein can be complexed with the gRNA prior to delivery. Viral vectors allow efficient delivery; split versions of Cas9 and smaller orthologs of Cas9 can be packaged in AAV, as can donors for HDR. A range of non-viral delivery methods also exist that can deliver each of these components, or non-viral and viral methods can be employed in tandem. For example, nanoparticles can be used to deliver the protein and guide RNA, while AAV can be used to deliver a donor DNA.

A composition described above can further have one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. In some embodiments, a composition can also include one or more components that can be used to facilitate or enhance the on-target binding or the cleavage of DNA by the endonuclease, or improve the specificity of targeting.

One or more components of a composition can be formulated with pharmaceutically acceptable excipients such as carriers, solvents, stabilizers, adjuvants, diluents, etc., depending upon the particular mode of administration and dosage form. In some embodiments, guide RNA compositions are generally formulated to achieve a physiologically compatible pH, and range from a pH of about 3 to a pH of about 11, about pH 3 to about pH 7, depending on the formulation and route of administration. In some embodiments, the pH is adjusted to a range from about pH 5 to about pH 8.

Suitable excipients can include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition will depend on the nature of the disorder or condition, and can be determined by standard clinical techniques.

The terms "stable" or "stability" as used herein can refer to the ability of the compounds herein described (e.g., an RNA-guided endonuclease or a nucleic acid encoding the RNA-guided endonuclease and/or gRNA) to maintain therapeutic efficacy (e.g., all or the majority of its intended biological activity and/or physiochemical integrity) over extended periods of time. The stability of one or more of the compounds described herein (e.g., an RNA-guided endonuclease or a nucleic acid encoding the RNA-guided endonuclease and/or a gRNA, and a nanoparticle) can be 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, or more than 3 years. The temperature of storage can vary. For example, the storage temperature can be, can be about, can be at least, or can be at least about −80° C., −65° C., −20° C., 5° C., or a number or range between any two of these values. In some embodiments, the storage temperature is less than or equal to −65° C.

In some embodiments, the compounds herein described (e.g., an RNA-guided endonuclease or a nucleic acid encoding the RNA-guided endonuclease and/or gRNA) of a composition can be delivered via transfection such as calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof. In some embodiments, the composition is introduced to the cells via lipid-mediated transfection using a lipid nanoparticle.

The compositions herein described can be administered to a subject in need thereof to treat an ALAS1-associated condition. Accordingly, the present disclosure also provides a gene therapy approach for treating an ALAS1-associated condition in a subject by editing the ALAS1 gene of the subject. In some embodiments, the ALAS1 gene of relevant cells in the subject (e.g., hepatocytes) is edited using the materials and methods described herein which uses RNA-guided endonuclease, such as Cas9, to edit a target sequence from a genome thereby resulting in reduced expression of ALAS1 in the liver, thereby providing a long-term or permanent cure for the ALAS1-associated condition by permanently reducing the levels of ALAS1 protein and/or preventing up-regulation of ALAS1 and prevent attacks of, e.g., acute porphyria. The term "associated" as used herein with reference to two items (e.g., ALAS1 and diseases/conditions) indicates a relation between the two items such that the occurrence of an item (e.g., ALAS1 protein level) is accompanied by the occurrence of the other item (e.g., a disease or condition), which includes but is not limited to a cause-effect relation and sign/symptom-disease relation.

As described herein, in some embodiments, the nanoparticles (e.g., LNPs comprising ionizable lipids) complexed with (a) a guide RNA (gRNA) or a nucleic acid encoding a gRNA that targets ALAS1 gene, and (b) a nucleic acid encoding a RNA-guided endonuclease (e.g., Cas9 mRNA) is administered to a subject in need via IV infusion. The administration can be, for example, a single dose, or two or more doses. The nanoparticles can be, for example, rapidly distributed to, e.g., liver of the subject, and the nanoparticles can enter hepatocytes of the subject (e.g., via endocytosis). In some embodiments, ionizable lipid disruption of endosome can break the nanoparticles, thereby releasing the nucleic acid encoding the RNA-guided endonuclease (e.g., Cas9 mRNA) from the nanoparticles. The RNA-guided endonuclease (e.g., Cas9) can be synthesized and form endonuclease-gRNA RNP complex to achieve gene-editing. In some embodiments, endogenous DNA repair through non-homologous end joining (NHEJ) results in introduction of indels into ALAS1 gene, leading to frameshift mutations that prevent production of functional ALAS1 protein. In some embodiments, the methods disclosed herein result in modulation (e.g., reduction) in ALAS1 expression. As demonstrated herein, using the methods, compositions, systems and kits described herein, robust on-target editing of ALAS1 gene can be achieved with no off-target editing.

Disclosed herein include methods for treating a disease or disorder caused by 5'-Aminolevulinate Synthase 1 (ALAS1) over-expression in a subject in need thereof. In some embodiments, the method comprises administering to the subject any one of the compositions disclosed herein, thereby treating the disease or disorder caused by ALAS1 over-expression in the subject. Disclosed herein include methods for treating a subject that has or is suspected of having porphyria. In some embodiments, the method comprises administering to the subject any one of the compositions disclosed herein, thereby treating the porphyria.

Disclosed herein include methods for treating a disease or disorder caused by ALAS1 over-expression in a subject in need thereof. In some embodiments, the method comprises administering to the subject a composition comprising a plurality of nanoparticles complexed with: (a) a guide RNA (gRNA) that targets an ALAS1 genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease, thereby treating the disease or disorder caused by ALAS1 over-expression in the subject.

Disclosed herein include methods for treating a subject that has or is suspected of having porphyria. In some embodiments, the method comprises administering to the subject a composition comprising a plurality of nanoparticles complexed with: (a) a gRNA that targets an ALAS1 genomic locus, comprising a spacer sequence comprising any one of the sequences of SEQ ID NOs: 25-48 and 83-112, or a nucleic acid encoding the gRNA; and (b) a Cas9 endonuclease or a nucleic acid encoding a Cas9 endonuclease, thereby treating the porphyria.

The Cas9 endonuclease can be, for example, *S. pyogenes* Cas9, *S. aureus* Cas9, *N. meningitides* Cas9, *S. thermophilus* CRISPR1 Cas9, *S. thermophilus* CRISPR 3 Cas9, or *T. denticola* Cas9. The plurality of nanoparticles can be lipid nanoparticles. The lipid nanoparticles can comprise one or more neutral lipids, charged lipids, ionizable lipids, steroids, and polymers conjugated lipids. The lipid nanoparticles can comprise cholesterol, a polyethylene glycol (PEG) lipid, or both.

The method can comprise administering to the subject the composition at a single dose of about 0.1 mg/kg, 0.3 mg/kg, 0.6 mg/kg, 1.0 mg/kg, or 2.0 mg/kg or more of total nucleic acids of (a) and (b). For example, a single dose or each dose of the plurality of nanoparticles administrated to the subject can be nanoparticles complexed with 0.01 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.5 mg/kg, 4 mg/kg, 4.5 mg/kg, or 5 mg/kg, or a number or a range between any two of these values total RNA (e.g., the total of ALAS1 gRNA and Cas9 mRNA). In some embodiments, the plurality of nanoparticles is administered to the subject at a dose of, or a dose about, 0.1 mg/kg, 0.3 mg/kg, 0.5 mg/kg, 0.6 mg/kg, 1 mg/kg, 1.5 mg/kg, 2.0 mg/kg, 2.5 mg/kg, 2 mg/kg or 3 mg/kg (determined by the total of ALAS1 gRNA and SpCas9 mRNA).

The method can comprise a single administration of the composition to the subject. The composition described herein (e.g., LNPs comprising ALAS1 gRNA) or a nucleic acid encoding an ALAS1 gRNA; and a nucleic acid encoding an RNA-guided endonuclease) can be administered to the subject in need thereof one or more times, for example once, twice, three times, four times, five times, or six times. It can be advantageous, in some embodiments, to provide a single administration of the composition to the subject. In some embodiments, it can be advantageous to provide up to three administrations (e.g., one, two or three administrations) of the composition to the subject. Any of the two administrations can be, for example, one day to one year part. For example, the first administration can be, or be about, 1 to 21 days apart (e.g., one day, two days, three days, four days, five days, six days, seven days, ten days, two weeks, three weeks, or a value or a range between any two of these values) apart from the second administration. As another example, the second administration can be, or be about, 1 day to one year (e.g., one day, two days, three days, four days, five days, six days, seven days, two weeks, three weeks, four weeks, five weeks, six weeks, two months, three months, six months, a year, or a value or a range between any two of these values) apart from the third administration. When there are three or more administrations, the interval between any of the two adjacent administrations can be the same or different in length. For example, in some embodiments, the first administration is about a week (e.g., 7 days) apart from the second administration, and the second administration is about five weeks (e.g., 35 days) apart from the third administration. The method described herein, in some embodiments, does not comprise regular on-schedule administration of the composition, e.g., every two days, every three days, every five days, weekly, biweekly, monthly, bimonthly, quarterly, biquarterly, yearly, or biyearly administration. In some embodiments, the method described herein does not comprise any administration of the composition three months, six months, nine months, a year, two years, or longer, after the first, second, or third administration of the composition. In some embodiments, the method described herein does not comprise any administration of the composition after the second or third administration of the composition. For example, the method described herein can be effective, in some embodiments, that the subject does not need to receive any additional treatment for conditions related to ALAS1 (e.g., porphyria) in the lifetime after the one-time treatment using the composition described herein.

The expression of ALAS1 in the subject can be reduced in the subject (e.g., following the administration). The expression of ALAS1 can be reduced in the liver of the subject. The reduction can be relative to (a) the ALAS1 expression of the subject prior to being administered the composition; (b) the ALAS1 expression in one or more untreated subjects; and/or (c) a reference level of ALAS1 expression of healthy subjects. The expression of ALAS1 in the subject can be reduced by at least 20% after the administration. The expression of ALAS1 mRNA can be reduced by at least 90% following the administration. The expression of ALAS1 protein can be reduced by at least 75% following the administration. In some embodiments, the expression of ALAS1 (e.g., ALAS 1 mRNA and/or ALAS1 protein) is reduced in the subject by about, by at least, or by at least about 20% in the subject after administration (e.g., 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values). In some embodiments, the genetic modification of the ALAS1 gene results in a significantly reduced ALAS1 protein or mRNA in liver. In some embodiments, the ALAS1 protein or mRNA level is reduced by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values. In some embodiments, the methods described herein can decrease the ALAS1 protein or mRNA level in the liver by about, at least or at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values.

In some embodiments, the levels of ALAS1 mRNA in the urine of the subject are reduced following administration of the composition; and wherein the reduction is relative to (a) the ALAS1 mRNA levels of the subject prior to being administered the composition; (b) the ALAS1 mRNA levels in one or more untreated subjects; and/or (c) a reference level of ALAS1 mRNA of healthy subjects. In some embodiments, the methods described herein can decrease the ALAS1 mRNA levels in urine by about, at least or at least about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values.

In some embodiments, the genetic modification of the ALAS1 gene results in significantly reduced levels of plasma porphyrins, urine porphyrins, fecal porphyrins or any combination thereof. In some embodiments, the plasma porphyrin, urine porphyrin, and/or fecal porphyrin levels are reduced by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values. In some embodiments, the methods described herein can decrease the plasma porphyrin, urine porphyrin, and/or fecal porphyrin levels by about, at least or at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values.

In some embodiments, the genetic modification of the ALAS1 gene results in significantly reduced of 5-aminolevulinic acid (e.g., 6-aminolevulinic acid, e.g., ALA) levels in the plasma and/or urine of the subject (e.g., mammal, NHP, a human subject). In some embodiments, the genetic modification of the ALAS1 gene results in a significantly reduced plasma and/or urine porphobilinogen (PBG) levels in the subject (e.g., mammal, NHP, a human subject).

In some embodiments, the ALAS1 protein and/or ALAS1 mRNA levels in a genetically modified subject (e.g., mammal, NHP, a human subject) are about, less than or less than about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to a corresponding unmodified mammal.

In some embodiments, the frequency of attacks of acute porphyria is reduced in the subject as compared to the subject prior to administration of any of the compositions disclosed herein. In some embodiments, the frequency of attacks of acute porphyria is reduced by, by about, by at least, or by at least about 5% or more (e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values) relative to the subject prior to administration of any of the compositions disclosed herein. In some embodiments, the subject does not experience an attack of acute porphyria following the administration.

The reduction can be for at least two weeks, at least three weeks, at least four weeks, or at least a month.

The method can comprise administering to the subject a therapeutically effective amount of at least one additional therapeutic agent to the subject. The additional therapeutic agent can be, or comprise, hematin (e.g., hemin), heme arginite, an ALAS1-specific siRNA, or a combination thereof. In some embodiments, the additional treatment is administered to the subject 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, or more prior to the administration of the plurality of nanoparticles to the subject. In some embodiments, the additional treatment is administered to the subject at most 2 hours prior to administration of the plurality of nanoparticles. In some embodiments, the additional treatment and the plurality of nanoparticles are administered simultaneously.

In some embodiments, the method can comprise administering to the subject a therapeutically effective amount of at least one additional therapeutic agent to treat one or more symptoms of porphyria (e.g., acute porphyria). In some embodiments, the additional treatment is an analgesic (e.g., acetaminophen, opioids, or a non-steroidal anti-inflammatory drug (NSAID) or a combination thereof). In some embodiments, the additional therapeutic agent can be a phenothiazine (e.g., Chlorpromazine) for alleviating, e.g., nausea. In some embodiments, insomnia can be treated by non-barbiturate sleep aides such as chloral hydrate or benzodiazepine. In some embodiments, seizures can be treated using, e.g., Levetiracetam. In some embodiments, the additional treatment is an siRNA therapy.

In some embodiments, the subject has, or is suspected of having, cutaneous porphyria. The cutaneous porphyria can be congenital erythropoietic porphyria (CEP), hepatoerythropoietic porphyria (HEP), Porphyria Cutanea Tarda (PCT), or erythropoietic protoporphyria and X-linked porphyria (EP/XLP). In some embodiments, the subject has, is suspected of having, or has had acute porphyria. The acute porphyria can be acute intermittent porphyria (AIP), hereditary coproporphyria (HCP), variegate porphyria (VP), or delta-aminolevulinic acid dehydratase deficiency porphyria (ADP).

As is understood by one skilled in the art, several tests can be used to diagnose a disease or disorder related to ALAS1 overexpression in a subject and/or evaluate state of the disease or disorder in the subject. The subject can have elevated urine porphobilinogen (PBG), elevated urine aminolevulinic acid (ALA), elevated urine porphyrins, elevated fecal porphyrins, elevated plasma porphyrins, or any combination thereof. In some embodiments, as compared to a reference value.

The levels of urine porphobilinogen (PBG), urine aminolevulinic acid (ALA), urine porphyrins, fecal porphyrins, plasma porphyrins, or any combination thereof can be reduced in the subject following administration of the composition.

In some embodiments, the subject has, or is suspected of having, a mutation in at least one gene selected from the group consisting of: ALAS2, ALAD, HMBS, UROD, UROS, CPOX, PPOX, and FECH. The mutation can result in a reduction in the expression, stability, and/or activity of the RNA and/or protein products of the at least one gene. The mutations can be dominant or recessive. In some embodiments, the subject has a mutation in one copy of the gene (e.g., is heterozygous for a mutation). In some embodiments, the subject as a mutation in both copies of the gene (e.g., is homozygous for a mutation). In some embodiments, the mutation is a dominant mutation, e.g., one copy of the mutation is sufficient to produce a mutant phenotype. In some embodiments, the mutation is a recessive mutation, e.g., both copies of the gene are mutated to produce a phenotype.

In some embodiments, the target tissue for the compositions and methods described herein is liver tissue. In some embodiments, the target cells for the compositions and methods described herein is hepatocyte.

In some embodiments, the pharmaceutical composition thereof can be administered by aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof. The administration can be local or systemic. The systemic administration includes enteral and parenteral administration. In some embodiments, more than one administration can be employed to achieve the desired level of gene expression over a period of various intervals, e.g., daily, weekly, monthly, or yearly.

The pharmaceutical composition thereof can be administered to a subject in need thereof at a pharmaceutically effective amount. The term "pharmaceutically effective amount" as used herein means that the amount of the pharmaceutical composition that will elicit a desired therapeutic effect and/or biological or medical responses of a tissue, system, animal or human. The administration can result in a desired reduction in the expression of the ALAS1 gene such as a desired reduction in the levels of the ALAS1 protein and one or more porphyrins.

EXAMPLES

Some aspects of the embodiments discussed above are disclosed in further detail in the following examples, which are not in any way intended to limit the scope of the present disclosure.

Example 1

Methods of Editing ALAS1 Gene

Provided in this Example are methods and compositions for editing ALAS1 gene in, e.g., mouse, monkey, and human cells.

Editing efficiency was tested in mouse, monkey, and human cell lines. Cell lines were plated in 100 µL of media/well in tissue culture treated 96-well flat bottom plates prior to transfection. MK2 (rhesus monkey kidney cell line) was plated the day before transfection and Huh-7-Cas9 (human liver cancer cell line with constitutive SpCas9 expression) and AML12 (mouse hepatocyte cell line with constitutive SpCas9 expression) were plated the day of transfection. Cells were plated at the following concentrations: Huh-7-Cas9: 15,000 cells/well, MK2: 20,000 cells/well, and AML12-Cas9: 30,000 cells/well. For transfection, 150 ng/well of guide was used for Huh-7-Cas9 and AML12-Cas9 and 200 ng/well of guide and 200 ng/well of Cas9 for MK2 using MessengerMAX Lipofectamine (Thermo Scientific, Waltham, MA). Plates were then incubated at 37° C. After 24 hours, the transfection mixture was removed and replaced with 100 µL of fresh media. The cells were incubated for another 48 hours and then DNA was isolated from the cells using a Quick-DNA 96 kit (Zymo Research, Irvine, CA). PCR was run to amplify regions of interest, for each unique guide, and TIDE analysis was performed to determine guide specific levels of editing.

Figure 2:
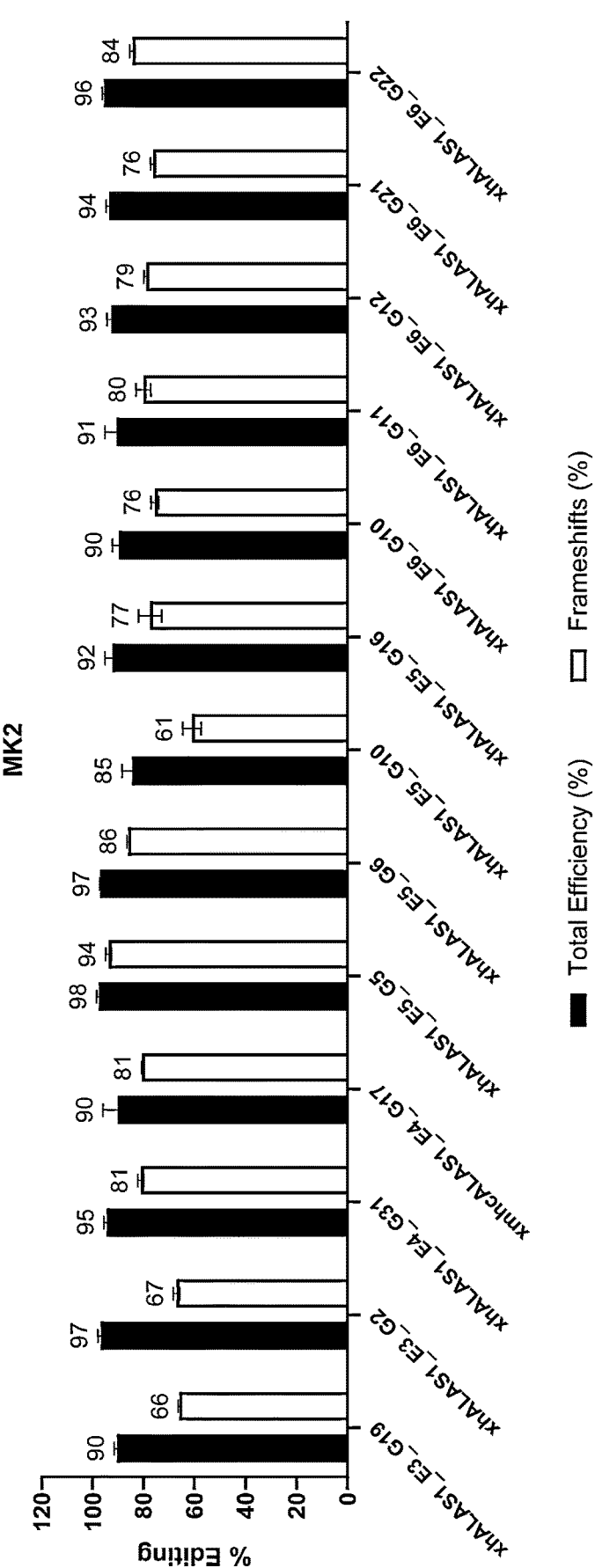
FIG. 2 displays non-limiting exemplary data depicting editing efficiencies of gRNAs comprising the indicated spacer sequences in LLC-MK2 rhesus monkey kidney cells.
Figure 3:
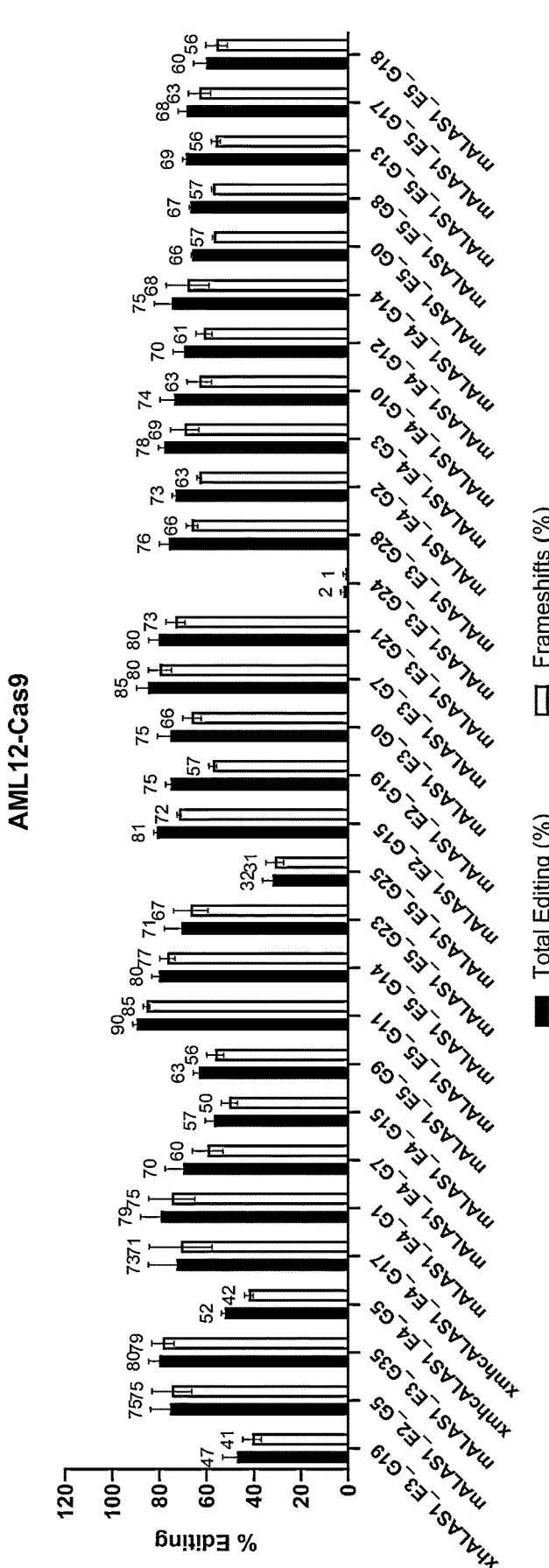
FIG. 3 displays non-limiting exemplary data depicting editing efficiencies of gRNAs comprising the indicated spacer sequences in AML12-Cas9 mouse hepatocyte cells.
Figure 3:

Exemplary editing efficiencies of the gRNAs disclosed herein are shown in FIG. 1-FIG. 3 and Table 3.

For experiments in Primary human hepatocytes (PHH, See, e.g., Table 4), PHH were thawed in 25 mL of Hepatocyte Thawing Media (Lonza, Basel, Switzerland). Cells were spun at 100×g for 8 minutes, resuspended in 4 mL of Hepatocyte Plating Media with Plating Media Supplement (Lonza, Basel, Switzerland), and counted. Cells were brought up to a concentration of $0.65 \times 10^6$ cells/mL, 500 µL of cells/well were plated into CellAdhere™ Collagen I-Coated 24-well plates (STEMCELL, Vancouver, BC). Every 10 minutes for one-hour post-seeding, the plate(s)

were shaken in a side-to-side and back-and-forth motion to evenly disperse cells, and placed into a 37° C., 5% $CO_2$ incubator. After 24 hours, the media was removed and replaced with 500 μL of prewarmed Hepatocyte Culture Media (Lonza, Basel, Switzerland). In some experiments, INVITROGRO CP Medium+TORPEDO Antibiotic Mix (BioIVT, Westbury, NY) was used for thawing, plating, and culturing of cells.

Figure 4:
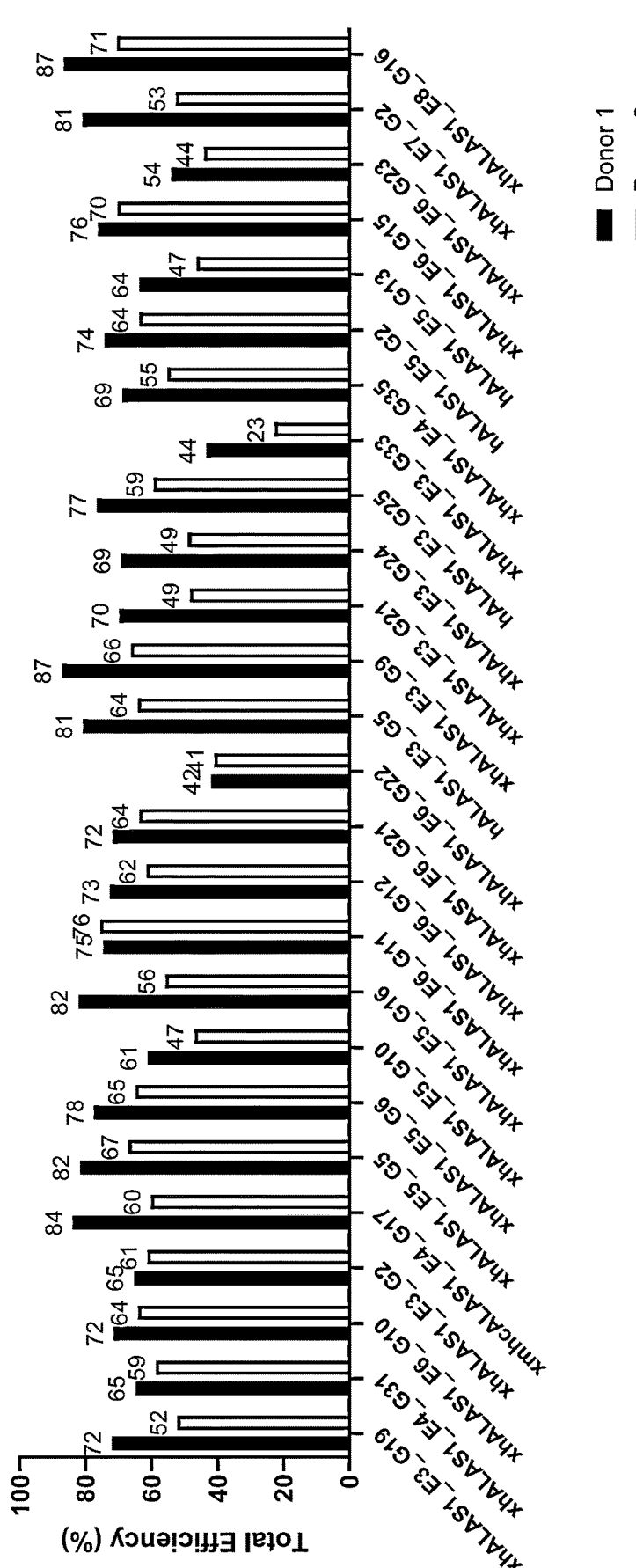
FIG. 4 displays non-limiting exemplary data depicting editing efficiencies of gRNAs comprising the indicated spacer sequences in human hepatocytes from two donors.

PHH cells were transfected with a 1:3 ratio of gRNA and Cas9 mRNA using MessengerMAX Lipofectamine (Thermo Scientific, Waltham, MA). Culture media was replaced 3 days post-transfection. Cells were incubated at 37° C., 5% $CO_2$ for a total of 6 days. DNA was isolated from cells using a QIAamp 96 DNA QIAcube HT kit (QIAGEN, Hilden, Germany). PCR was run to amplify regions of interest and TIDE analysis or amplicon sequencing was performed to determine guide specific levels of editing. Exemplary editing efficiencies of the gRNAs disclosed herein are shown in FIG. 4 and Table 4.

Shown below in Table 1 and Table 2 are the gRNA spacer sequences (and the corresponding PAM-strand protospacer (e.g., target) sequence and the PAM).

TABLE 1

HUMAN/MONKEY TARGET AND GRNA SEQUENCES

| Name | Target* SEQ ID NO: | Sequence | PAM | Spacer SEQ ID NO: |
|---|---|---|---|---|
| xhALAS1_E3_G19† | 1 | GCCCCAACTTCCATCATCTT | GGG | 25 |
| xhALAS1_E4_G31 | 2 | GATGGCACACAGCTTCCGTC | TGG | 26 |
| xhALAS1_E6_G10 | 3 | TAACTGCCCCACACACCCGT | GGG | 27 |
| xhALAS1_E3_G2 | 4 | ATTCTTATCCCGAGTCCCCC | AGG | 28 |
| xmhcALAS1_E4_G17† | 5 | AGAAGATGAGACACTCTTTC | TGG | 29 |
| xhALAS1_E5_G5 | 6 | TTTTCACACTAACCACACTG | GGG | 30 |
| xhALAS1_E5_G6 | 7 | GTTTTCACACTAACCACACT | GGG | 31 |
| xhALAS1_E5_G10 | 8 | GCTGAGGTTTCAGCAACCTC | TGG | 32 |
| xhALAS1_E5_G16 | 9 | TTTGCTTTTGCATGATGTCC | TGG | 33 |
| xhALAS1_E6_G11 | 10 | AGGAATGAGTCGCCACCCAC | GGG | 34 |
| xhALAS1_E6_G12 | 11 | GTCGCCACCCACGGGTGTGT | GGG | 35 |
| xhALAS1_E6_G21 | 12 | ATAACTGCCCCACACACCCG | TGG | 36 |
| xhALAS1_E6_G22 | 13 | AGTCGCCACCCACGGGTGTG | TGG | 37 |
| hALAS1_E3_G5 | 70 | CACTTACTCTCACTGGCCGG | AGG | 100 |
| xhALAS1_E3_G9 | 71 | TGACACTTACTCTCACTGGC | CGG | 101 |
| xhALAS1_E3_G21 | 72 | TGCAGTGGACAATGCCCGAG | GGG | 102 |
| xhALAS1_E3_G24 | 73 | CTTACTCTCACTGGCCGGAG | GGG | 103 |
| hALAS1_E3_G25 | 74 | ACTTACTCTCACTGGCCGGA | GGG | 104 |
| xhALAS1_E3_G33 | 75 | GTGGACAATGCCCGAGGGGC | TGG | 105 |
| xhALAS1_E4_G35 | 76 | ATCCTCCTGAAGCTCAAGAC | TGG | 106 |
| hALAS1_E5_G2 | 77 | GTTAGTGTGAAAACCGATGG | AGG | 107 |

TABLE 1-continued

HUMAN/MONKEY TARGET AND GRNA SEQUENCES

| Name | Target* SEQ ID NO: | Sequence | PAM | Spacer SEQ ID NO: |
|---|---|---|---|---|
| hALAS1_E5_G13 | 78 | GTGGTTAGTGTGAAAACCGA | TGG | 108 |
| xhALAS1_E6_G15 | 79 | TTTTAAAAACTCGATAGGTG | TGG | 109 |
| xhALAS1_E6_G23 | 80 | GCAGTTATGTAAGTAGCCCT | TGG | 110 |
| xhALAS1_E7_G2 | 81 | GTCATTGGCCACAAAGCACG | AGG | 111 |
| xhALAS1_E8_G16 | 82 | CTCGGCTGTTTCGAATCCCT | TGG | 112 |

†May also be used for editing mouse sequences.

*In some embodiments, the target sequence is the corresponding DNA version of the spacer sequence. In the genomic context, the strand comprising the target sequence can be adjacent to or nearby a PAM.

TABLE 2

MOUSE TARGET AND GRNA SEQUENCES

| Name | Target* SEQ ID NO: | Sequence | PAM | Spacer SEQ ID NO: |
|---|---|---|---|---|
| mALAS1_E2_G5 | 14 | GCTGATGTGGACAGGGTTCG | AGG | 38 |
| mALAS1_E3_G35 | 15 | CGTCTTCCGCAAGGCCAGTC | TTG | 39 |
| xmhcALAS1_E4_G5 | 16 | AAGAGTGTCTCATCTTCTTC | AGG | 40 |
| mALAS1_E4_G1 | 17 | CATCGGTTTTCACATTAACC | AGG | 41 |
| mALAS1_E4_G7 | 18 | TCGGCTTGGATCCTCTCCAT | CGG | 42 |
| mALAS1_E4_G15 | 19 | AAGTTCTTCAGCAGTCGGCT | TGG | 43 |
| mALAS1_E5_G9 | 20 | TCCGTGTAGTCATCCGCCAT | CGG | 44 |
| mALAS1_E5_G11 | 21 | CCCGATGGCGGATGACTACA | CGG | 45 |
| mALAS1_E5_G14 | 22 | CCGTGTAGTCATCCGCCATC | GGG | 46 |
| mALAS1_E5_G23 | 23 | CCAAAAAGCAGGTGTCGGTC | TGG | 47 |
| mALAS1_E5_G25 | 24 | AGTCGACACCCACGGGTGTG | TGG | 48 |
| mALAS1_E2_G15 | 53 | GCCCCAAGATGATGGAAGTT | GGG | 83 |
| mALAS1_E2_G19 | 54 | GGCCCCAACTTCCATCATCT | TGG | 84 |
| mALAS1_E3_G0 | 55 | TGCCAAGGCCGCAGTCCAGC | AGG | 85 |
| mALAS1_E3_G7 | 56 | AGGCAGCAGCGTCTTCCGCA | AGG | 86 |
| mALAS1_E3_G21 | 57 | CCGTCCCCTGCTACAAGCCA | GGG | 87 |
| mALAS1_E3_G24 | 58 | AGCCTGCTGGACTGCGGCCT | TGG | 88 |
| mALAS1_E3_G28 | 59 | GACGGAAGCTGTGTGCCGTC | TGG | 89 |
| mALAS1_E4_G2 | 60 | TAATGTGAAAACCGATGGAG | AGG | 90 |
| mALAS1_E4_G3 | 61 | CCGACTGCTGAAGAACTTCC | AGG | 91 |
| mALAS1_E4_G10 | 62 | GTTTTCACATTAACCAGGCT | GGG | 92 |
| mALAS1_E4_G12 | 63 | GGTTTTCACATTAACCAGGC | TGG | 93 |

TABLE 2-continued

MOUSE TARGET AND GRNA SEQUENCES

| Name | Tar-get* SEQ ID NO: | Sequence | PAM | Spac-er SEQ ID NO: |
|---|---|---|---|---|
| mALASI_E4_G14 | 64 | CTGGTTAATGTGAAAACCGA | TGG | 94 |
| mALAS1_E5_G0 | 65 | CACCGTTTTAAAAACTCGGT | AGG | 95 |
| mALAS1_E5_G8 | 66 | GAGTTTTTAAAACGGTGAAC | CGG | 96 |
| mALAS1_E5_G13 | 67 | TAGGCATGAGTCGACACCCA | CGG | 97 |

TABLE 2-continued

MOUSE TARGET AND GRNA SEQUENCES

| Name | Tar-get* SEQ ID NO: | Sequence | PAM | Spac-er SEQ ID NO: |
|---|---|---|---|---|
| mALAS1_E5_G17 | 68 | AGGCATGAGTCGACACCCAC | GGG | 98 |
| mALASI_E5_G18 | 69 | GTCGACACCCACGGGTGTGT | GGG | 99 |

*In some cases, the target sequence is the DNA version of the spacer sequence. In the genomic context, the strand comprising the target sequence is adjacent to or nearby a PAM.

TABLE 3

EDITING EFFICIENCIES OF DISCLOSED ALAS1 GRNAS

| Cell Line | Guide Name | †SEQ ID NO: | Total Efficiency (%) | Frameshifts (%) |
|---|---|---|---|---|
| Huh7-Cas9 | xhALAS1_E3_G19 | 25 | 83.83 | 70.13 |
| Huh7-Cas9 | xhALAS1_E3_G2 | 28 | 97.50 | 82.25 |
| Huh7-Cas9 | xhALAS1_E4_G31 | 26 | 95.88 | 88.15 |
| Huh7-Cas9 | xmhcALAS1_E4_G17 | 29 | 84.33 | 77.65 |
| Huh7-Cas9 | xhALAS1_E5_G5 | 30 | 98.08 | 96.70 |
| Huh7-Cas9 | xhALAS1_E5_G6 | 31 | 93.40 | 85.65 |
| Huh7-Cas9 | xhALAS1_E5_G10 | 32 | 86.83 | 68.58 |
| Huh7-Cas9 | xhALAS1_E5_G16 | 33 | 27.73 | 21.93 |
| Huh7-Cas9 | xhALAS1_E6_G10 | 27 | 95.43 | 89.33 |
| Huh7-Cas9 | xhALAS1_E6_G11 | 34 | 96.88 | 94.08 |
| Huh7-Cas9 | xhALAS1_E6_G12 | 35 | 94.45 | 85.23 |
| Huh7-Cas9 | xhALAS1_E6_G21 | 36 | 93.65 | 82.33 |
| Huh7-Cas9 | xhALAS1_E6_G22 | 37 | 97.95 | 91.65 |
| MK2 | xhALAS1_E3_G19 | 25 | 90.40 | 65.95 |
| MK2 | xhALAS1_E3_G2 | 28 | 96.85 | 67.00 |
| MK2 | xhALAS1_E4_G31 | 26 | 94.60 | 81.08 |
| MK2 | xmhcALAS1_E4_G17 | 29 | 90.15 | 80.67 |
| MK2 | xhALAS1_E5_G5 | 30 | 97.63 | 93.70 |
| MK2 | xhALAS1_E5_G6 | 31 | 97.10 | 86.10 |
| MK2 | xhALAS1_E5_G10 | 32 | 84.53 | 60.98 |
| MK2 | xhALAS1_E5_G16 | 33 | 92.30 | 77.40 |
| MK2 | xhALAS1_E6_G10 | 27 | 89.80 | 75.50 |
| MK2 | xhALAS1_E6_G11 | 34 | 90.68 | 80.03 |
| MK2 | xhALAS1_E6_G12 | 35 | 92.78 | 78.93 |
| MK2 | xhALAS1_E6_G21 | 36 | 93.53 | 76.28 |
| MK2 | xhALAS1_E6_G22 | 37 | 95.58 | 84.35 |
| AML12-Cas9 | xhALAS1_E3_G19 | 25 | 47.00 | 40.75 |
| AML12-Cas9 | mALAS1_E2_G5 | 38 | 75.45 | 74.68 |
| AML12-Cas9 | mALAS1_E3_G35 | 39 | 80.10 | 78.53 |
| AML12-Cas9 | xmhcALAS1_E4_G5 | 40 | 52.23 | 42.20 |
| AML12-Cas9 | xmhcALAS1_E4_G17 | 29 | 72.65 | 70.90 |
| AML12-Cas9 | mALAS1_E4_G1 | 41 | 79.43 | 74.70 |
| AML12-Cas9 | mALAS1_E4_G7 | 42 | 69.85 | 59.53 |
| AML12-Cas9 | mALAS1_E4_G15 | 43 | 56.73 | 50.33 |
| AML12-Cas9 | mALAS1_E5_G9 | 44 | 63.23 | 56.28 |
| AML12-Cas9 | mALAS1_E5_G11 | 45 | 89.65 | 85.43 |
| AML12-Cas9 | mALAS1_E5_G14 | 46 | 80.20 | 76.60 |
| AML12-Cas9 | mALAS1_E5_G23 | 47 | 70.53 | 66.70 |
| AML12-Cas9 | mALAS1_E5_G25 | 48 | 32.10 | 31.23 |
| AML12-Cas9 | mALAS1_E2_G15 | 83 | 81.13 | 71.70 |
| AML12-Cas9 | mALAS1_E2_G19 | 84 | 75.20 | 57.30 |
| AML12-Cas9 | mALAS1_E3_G0 | 85 | 75.28 | 66.15 |
| AML12-Cas9 | mALAS1_E3_G7 | 86 | 84.90 | 79.80 |
| AML12-Cas9 | mALAS1_E3_G21 | 87 | 80.30 | 73.15 |
| AML12-Cas9 | mALAS1_E3_G24 | 88 | 2.03 | 1.19 |
| AML12-Cas9 | mALAS1_E3_G28 | 89 | 75.98 | 66.20 |
| AML12-Cas9 | mALAS1_E4_G2 | 90 | 73.05 | 63.03 |
| AML12-Cas9 | mALAS1_E4_G3 | 91 | 77.93 | 69.23 |
| AML12-Cas9 | mALAS1_E4_G10 | 92 | 73.65 | 62.95 |
| AML12-Cas9 | mALAS1_E4_G12 | 93 | 69.50 | 61.08 |
| AML12-Cas9 | mALAS1_E4_G14 | 94 | 74.75 | 67.93 |
| AML12-Cas9 | mALAS1_E5_G0 | 95 | 65.95 | 56.83 |
| AML12-Cas9 | mALAS1_E5_G8 | 96 | 66.83 | 57.18 |

TABLE 3-continued

EDITING EFFICIENCIES OF DISCLOSED ALAS1 GRNAS

| Cell Line | Guide Name | †SEQ ID NO: | Total Efficiency (%) | Frameshifts (%) |
|---|---|---|---|---|
| AML12-Cas9 | mALAS1_E5_G13 | 97 | 68.68 | 56.00 |
| AML12-Cas9 | mALAS1_E5_G17 | 98 | 68.43 | 62.98 |
| AML12-Cas9 | mALAS1_E5_G18 | 99 | 60.10 | 55.68 |

†RNA spacer sequence

TABLE 4

EDITING EFFICIENCIES OF DISCLOSED ALAS1
GRNAS IN PRIMARY HUMAN HEPATOCYTES

| | Total Editing % | | |
|---|---|---|---|
| Name | Donor 1 | Donor 2 | *SEQ ID NO: |
| xhALAS1_E3_G19† | 72.10 | 52.20 | 25 |
| xhALAS1_E4_G31 | 64.90 | 58.70 | 26 |
| xhALAS1_E6_G10 | 71.50 | 64.10 | 27 |
| xhALAS1_E3_G2 | 65.40 | 61.30 | 28 |
| xmhcALAS1_E4_G17† | 84.00 | 60.20 | 29 |
| xhALAS1_E5_G5 | 81.77 | 67.00 | 30 |
| xhALAS1_E5_G6 | 77.50 | 64.90 | 31 |
| xhALAS1_E5_G10 | 61.20 | 47.10 | 32 |
| xhALAS1_E5_G16 | 82.20 | 55.80 | 33 |
| xhALAS1_E6_G11 | 74.70 | 75.60 | 34 |
| xhALAS1_E6_G12 | 72.80 | 61.50 | 35 |
| xhALAS1_E6_G21 | 71.90 | 63.80 | 36 |
| xhALAS1_E6_G22 | 42.10 | 41.10 | 37 |
| hALAS1_E3_G5 | 80.90 | 64.20 | 100 |
| xhALAS1_E3_G9 | 87.30 | 66.30 | 101 |
| xhALAS1_E3_G21 | 69.90 | 48.50 | 102 |
| xhALAS1_E3_G24 | 69.30 | 49.05 | 103 |
| hALAS1_E3_G25 | 76.70 | 59.40 | 104 |
| xhALAS1_E3_G33 | 43.50 | 22.75 | 105 |
| xhALAS1_E4_G35 | 68.95 | 55.20 | 106 |
| hALAS1_E5_G2 | 74.35 | 63.80 | 107 |
| hALAS1_E5_G13 | 63.75 | 46.55 | 108 |
| xhALAS1_E6_G15 | 76.25 | 70.35 | 109 |
| xhALAS1_E6_G23 | 54.05 | 44.25 | 110 |
| xhALAS1_E7_G2 | 81.05 | 52.60 | 111 |
| xhALAS1_E8_G16 | 86.70 | 70.55 | 112 |

†May also be used for editing mouse sequences
*RNA spacer sequence

Example 2

Methods of Editing ALAS1 Gene in Mouse Liver

Provided in this Example are exemplary methods for editing ALAS1 in mouse liver.

Article Administration Protocol

Animals were warmed for approximately 5 minutes using a heat lamp. A mouse was placed in the restraint device and the tail cleansed with an isopropanol wipe. Lipid nanoparticles (LNPs) formulated with Cas9 mRNA and mALAS1_E2_G5(SEQ ID NO: 38), xmhcALAS1_E4_G17 (SEQ ID NO: 29), or mALAS1_E5_G11 (SEQ ID NO: 45) gRNA were administered by bolus injection into one of the lateral tail veins using a 1 mL syringe equipped with a 26-gauge needle at 1.0 mg/kg and 2.0 mg/kg. Following administration, the needle was withdrawn and direct pressure applied using a gauze square until hemostasis was achieved, after which the animal was returned to its cage.

Tissue Collection for Molecular Analysis

The liver was removed and placed on a cutting board. A piece of tissue approximately 5 mm$^3$ was removed and placed in a vial containing grinding beads. The vial was placed under dry ice and the tissue allowed to rapidly freeze.

Molecular Analysis

Figure 5:
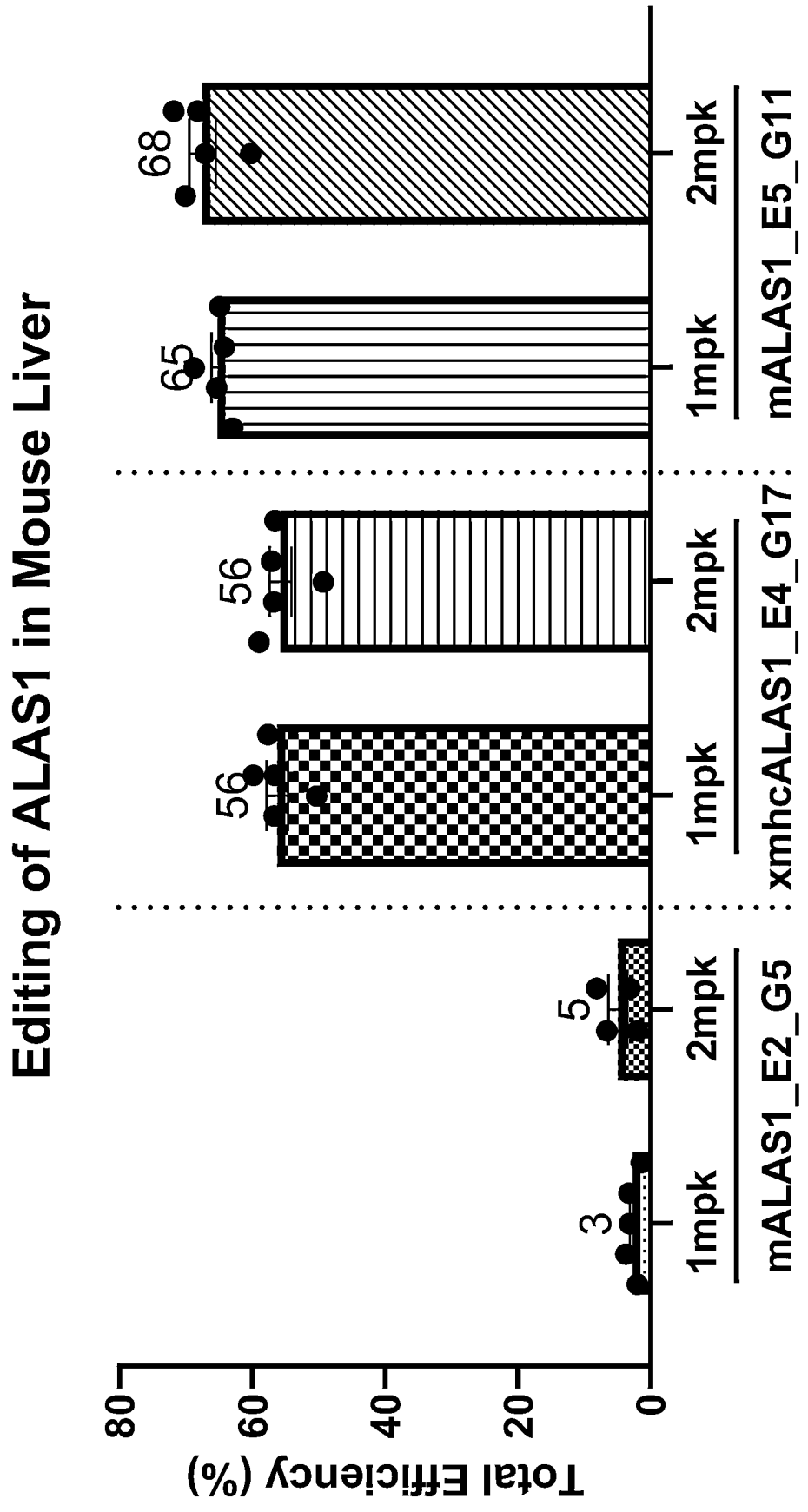
FIG. 5 displays non-limiting exemplary data depicting editing efficiencies of gRNAs comprising the indicated spacer sequences in mouse liver. As used herein, "mpk" stands for milligram per kilogram (mg/kg) of LNP/mouse weight.

DNA was isolated from snap frozen murine livers using a DNeasy Blood & Tissue Kit (QIAGEN, Hilden, Germany) according to manufacturer's protocol. PCR was then run to amplify regions of interest and TIDE analysis was performed to determine total editing levels. Exemplary results are shown in FIG. 5.

Example 3

Methods of Editing ALAS1 Gene in Hepatocytes

Provided in this Example are exemplary methods for editing ALAS1 in human cells, e.g., primary human hepatocytes.

Figure 6:
FIG. 6 displays non-limiting exemplary data depicting editing efficiencies of gRNAs comprising the xhALAS1_E5_G5 (SEQ ID NO: 30) spacer sequence in primary human hepatocytes.

Primary human hepatocytes (PHH) from 6 donors were thawed in 15 mL of INVITROGRO CP Medium+ TORPEDO Antibiotic Mix (BioIVT, Westbury, NY). Cells were spun at 100×g for 8 minutes, resuspended in 4 mL of INVITROGRO CP Medium+ TORPEDO Antibiotic Mix (BioIVT, Westbury, NY), and counted. Cells were brought up to a concentration of 0.65×10$^6$ cells/mL. 500 µL of cells/well were plated into CellAdhere™ Collagen I-Coated 24-well plates (STEMCELL, Vancouver, BC). Every 10 minutes for one-hour post-seeding, the plate(s) were shaken in a side-to-side and back-and-forth motion to evenly disperse cells, and placed into a 37° C., 5% CO$_2$ incubator. The following day, media was removed and replaced with 500 µL of prewarmed INVITROGRO CP Medium+ TORPEDO Antibiotic Mix (BioIVT, Westbury, NY) containing corresponding amounts of lipid nanoparticles (LNP) formulated with Cas9 mRNA and xhALAS1_E5_G5 (SEQ ID NO: 30). Three days post LNP treatment, DNA was isolated from the cells using a QIAamp 96 DNA QIAcube HT kit (QIAGEN, Hilden, Germany). PCR was run to amplify regions of interest and amplicon sequencing was performed to determine total editing levels. Exemplary results are displayed in FIG. 6.

The aim of the editing in ALAS1 gene is to knockdown ALAS1 protein expression. To assess the protein knockdown efficacy versus editing, one donor each of primary human hepatocytes and primary NHP hepatocytes were thawed in 15 mL of INVITROGRO CP Medium+ TORPEDO Antibiotic Mix (BioIVT, Westbury, NY). Cells were spun at 100×g for 8 minutes, resuspended in 4 mL of INVITROGRO CP Medium+ TORPEDO Antibiotic Mix (BioIVT, Westbury, NY), and counted. Cells were brought up to a concentration of 0.65×10$^6$ cells/mL. 500 µL of cells/well were plated into CellAdhere™ Collagen I-Coated 24-well plates (STEMCELL, Vancouver, BC). Every 10 minutes for one-hour post-seeding, the plate(s) were shaken in a side-to-side and back-and-forth motion to evenly disperse cells, and placed into a 37° C., 5% CO$_2$ incubator. The following day, media was removed and replaced with 500 µL of prewarmed INVITROGRO CP Medium+ TORPEDO

59

Figure 9A:
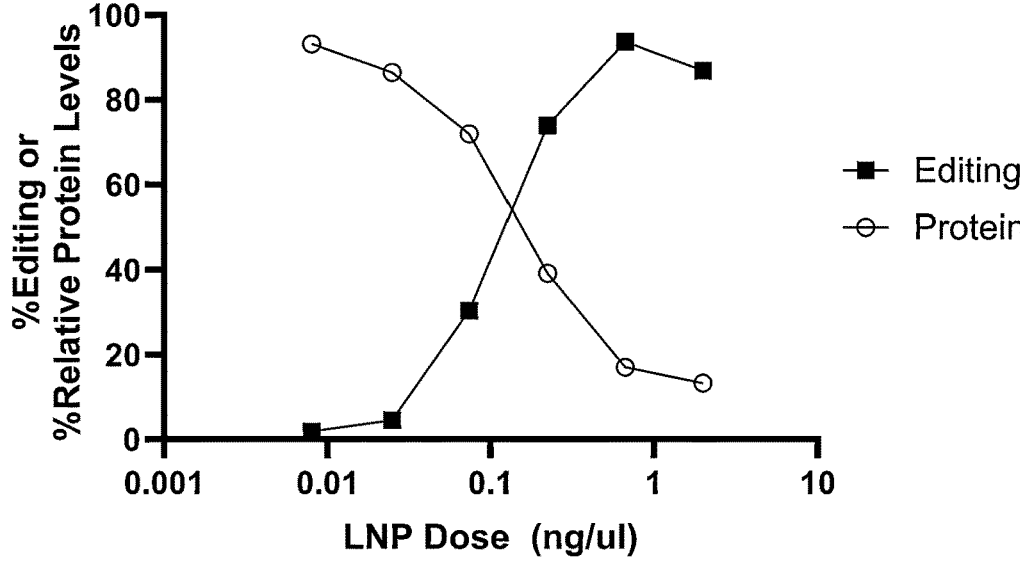
FIG. 9A-FIG. 9B display non-limiting exemplary data related to ALAS1 editing and protein dose curve in human and NHP hepatocytes treated with LNP formulated with Cas9 mRNA and xhALAS1_E5_G5 (SEQ ID NO: 30).
Figure 9B:
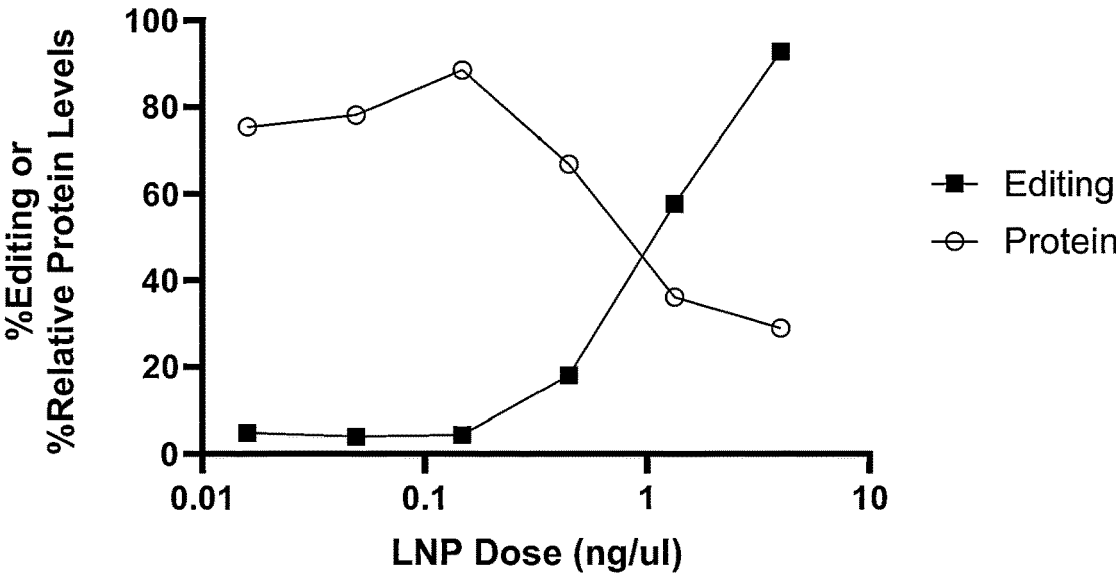

Antibiotic Mix (BioIVT, Westbury, NY) containing corresponding amounts of lipid nanoparticles (LNP) formulated with Cas9 mRNA and xhALAS1_E5_G5 (SEQ ID NO: 30). Media was replaced with fresh prewarmed medium three days post LNP treatment. On Day 5 post LNP treatment, DNA was isolated from the cells using a QIAamp 96 DNA QIAcube HT kit (QIAGEN, Hilden, Germany) and protein lysate was extracted. PCR was run to amplify regions of interest on the DNA and amplicon sequencing was performed to determine total editing levels. ALAS1 protein expression level was determined via capillary-based immunoassay and is presented as the relative expression of treated samples compared to untreated samples. Exemplary results are displayed in FIG. 9A-FIG. 9B.

Example 4

Figure 8:
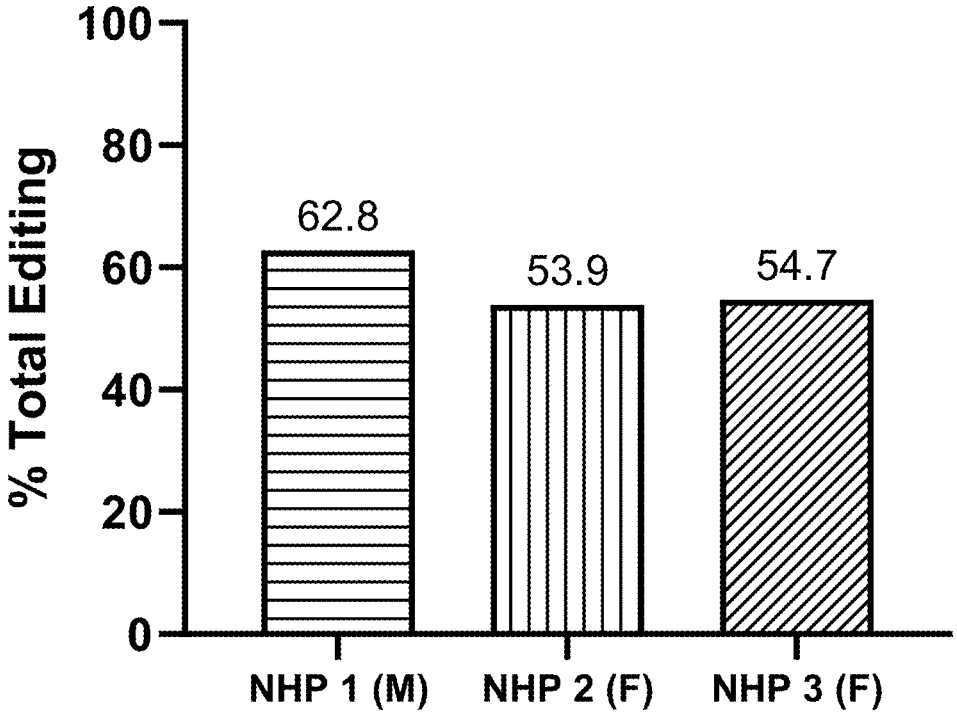
FIG. 8 displays non-limiting exemplary data related to activity of gRNAs of the disclosure. Percent editing of ALAS1 in liver of individual NHP administered the indicated gRNA is shown.

Methods of Editing ALAS1 Gene In Vivo
Provided in this Example are methods and data related to editing of ALAS1 in vivo.
NHP Data Method
Lipid nanoparticles (LNPs) formulated with Cas9 mRNA and xhALAS1_E5_G5 gRNA (SEQ ID NO: 30) were administered intravenously to cynomolgus macaque (NHP) at 2.0 mg/kg. ALAS1 editing in the liver was evaluated by amplicon sequencing from DNA isolated using a DNeasy Blood & Tissue Kit (QIAGEN, Hilden, Germany) according to manufacturer's protocol (FIG. 8).

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A guide RNA (gRNA) for targeting a 5'-Aminolevulinate Synthase 1 (ALAS1) genomic locus, comprising a spacer sequence having at least 80% sequence identity to any one of the sequences of SEQ ID NOs: 25-47, 83-87, and 89-112, and wherein the gRNA is capable of inducing a cutting efficiency of at least 40% for targeting the ALAS1 genomic locus.

2. The gRNA of claim 1, comprising a spacer sequence comprising any one of the sequences of SEQ ID NOs: 25-47, 83-87, and 89-112.

3. The gRNA of claim 1, wherein the gRNA comprises a spacer sequence comprising any one of the sequences of SEQ ID NOs: 25-37 and 100-112.

4. The gRNA of claim 1, wherein the gRNA is capable of inducing a cutting efficiency of at least 50% for targeting the ALAS1 genomic locus.

5. The gRNA of claim 1, wherein the gRNA is a chemically-modified gRNA.

6. A composition, comprising:
(a) a guide RNA (gRNA) that targets a 5'-Aminolevulinate Synthase 1 (ALAS1) genomic locus, or a nucleic acid encoding the gRNA, wherein the gRNA comprises a spacer sequence having at least 80% sequence identity to any one of the sequences of SEQ ID NOs: 25-47, 83-87, and 89-112, and is capable of inducing a cutting efficiency of at least 40% for targeting the ALAS1 genomic locus; and
(b) an endonuclease or a nucleic acid encoding an endonuclease.

7. The composition of claim 6, wherein the gRNA is a chemically-modified gRNA comprising one or more phosphorothioate linkages and/or one or more 2'-O-methyl nucleotides at the 3' end, the 5' end, or both.

8. The composition of claim 6, wherein the composition comprises (a) the ALAS1 gRNA and (b) the Cas9 endonuclease, and the ALAS1 gRNA and Cas9 endonuclease are formulated as a ribonucleoprotein particle (RNP).

* * * * *